US010526339B2

(12) United States Patent
Spiegel et al.

(10) Patent No.: US 10,526,339 B2
(45) Date of Patent: Jan. 7, 2020

(54) SUBSTITUTED GLUCOSEPANES AND COMPOSITIONS THEREOF

(71) Applicant: YALE UNIVERSITY, New Haven, CT (US)

(72) Inventors: David Spiegel, Hamden, CT (US); Cristian Draghici, Boston, MA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/762,816

(22) PCT Filed: Sep. 23, 2016

(86) PCT No.: PCT/US2016/053407
§ 371 (c)(1),
(2) Date: Mar. 23, 2018

(87) PCT Pub. No.: WO2017/053776
PCT Pub. Date: Mar. 30, 2017

(65) Prior Publication Data
US 2018/0291031 A1    Oct. 11, 2018

Related U.S. Application Data

(60) Provisional application No. 62/232,626, filed on Sep. 25, 2015.

(51) Int. Cl.
*A61K 31/55* (2006.01)
*C07D 487/04* (2006.01)
*C07D 491/048* (2006.01)
*C07C 281/16* (2006.01)
*A61K 45/06* (2006.01)

(52) U.S. Cl.
CPC ......... *C07D 491/048* (2013.01); *A61K 31/55* (2013.01); *A61K 45/06* (2013.01); *C07C 281/16* (2013.01); *C07D 487/04* (2013.01)

(58) Field of Classification Search
CPC ............................. A61K 31/55; C07D 487/04
USPC .......................................... 514/215; 540/593
See application file for complete search history.

(56) References Cited

U.S. PATENT DOCUMENTS

| 4,044,118 | A | 8/1977 | McCoy et al. |
| 4,348,331 | A | 9/1982 | Dickore et al. |
| 4,522,811 | A | 6/1985 | Eppstein et al. |
| 5,994,577 | A | 11/1999 | Larsen et al. |

FOREIGN PATENT DOCUMENTS

| CN | 101016270 A | 8/2007 |
| DE | 2029707 A | 6/1970 |
| DE | 2222925 | 2/1973 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Walsh CT, et al., Protein posttranslational modifications: the chemistry of proteome diversifications. Angew. Chem. Int Ed. Engf. 2005;44:7342-7372.
Singh R, et al. Advanced glycation end-products: a review. Diabetologia, 2001;44:129-146.
Monnier VM, et al. Glucosepane: a poorly understood advanced glycation end product of growing importance for diabetes and its complications. Clin Chem Lab Med, 2014;52:21-32.
Hellwig M, Henle T. Baking, ageing, diabetes: a short history of the Maillard reaction. Angew Chem Int Ed Engl, 2014;53:10316-10329.
Biemel KM, et al. Identification and quantification of major maillard cross-links in human serum albumin and lens protein. Evidence for glucosepane as the dominant compound. J Biol Chem, 2002;277:24907-24915.
Biemel K, et al. Identification and quantitative evaluation of the lysine arginine crosslinks GODIC, MODIC, DODIC, and glucosepan in foods. Nahrung/Food, 2001;45:210-214.
Monnier VM, et al. The association between skin collagen glucosepane and past progression of microvascular and neuropathic complications in type 1 diabetes. J Diabetes Complicat, 2013;27:141-149.
Sjoberg JS, Bulterijs S. Characteristics formation, and pathophysiology of glucosepane: a major protein cross-link. Rejuvenation Res, 2009;12:137-148.
Fan X, et al. Anaerobic vs aerobic pathways of carbonyl and oxidant stress in human lens and skin during aging and in diabetes: A comparative analysis. Free Radic Biol Med, 2010;49:847-856.
Sell D, et al. Glucosepane is a major protein cross-link of the senescent human extracellular matrix—Relationship with diabetes. J Biol Chem, 2005;280:12310-12315.
Schnider SL, Kohn RR. Effects of age and diabetes mellitus on the solubility and nonenzymatic glucosylation of human skin collagen. J Clin Invest, 1981:67:1630-1635.
Schnider SL, Kohn RR. Effects of ge and diabetes mellitus on the solubility of collagen from human skin, tracheal cartilage and dura mater. Exp Gerontol, 1982;17:185-194.

(Continued)

*Primary Examiner* — Douglas M Willis
(74) *Attorney, Agent, or Firm* — Henry D. Coleman; R. Neil Sudol

(57) ABSTRACT

Glucosepane is a structurally complex protein post-translational modification (PTM) believed to exist in all living organisms. Glucosepane possesses a unique chemical structure that incorporates a surprising, never-before-prepared non-aromatic tautomer of imidazole, rendering it a challenging target for chemical synthesis. In this application, the inventors report the first total synthesis of glucosepane and related compounds according to the chemical structure:

Methods of synthesis, compounds obtained therefrom, pharmaceutical compositions and methods of treatment provide embodiments of the present invention.

11 Claims, 8 Drawing Sheets

(56) References Cited

OTHER PUBLICATIONS

Vater CA, et al. Native cross-links in collagen fibrils induce resistance to human synovial collagenase. Biochem J, 1979;181:639-645.

Genuth S, et al. Skin Advanced Glycation End Products Glucosepane and Methylglyoxal Hydroimidazolone Are Independently Associated With Long-term Microvascular Implication Progression of Type 1 Diabetes. Diabetes, 2014;64:266-278.

Manigrasso MB, et al. Unlocking the biology of RAGE in diabetic microvascular complications. Trends Endocrin Met, 2014;25:15022.

Henle T. AGEs in foods: Do they play a role in uremia? Kidney Int, 2003;63:S145-S147.

Biemel KM, et al. Unexpected carbonyl mobility in aminoketoses: the key to major Maillard crosslinks. Angew Chem Int Ed Engl, 2002;41:801-804.

Chermahini AN, et al. Relation between the substituent effect and aromaticity in imidazole derivatives: A comparative study. Comput Theor Chem, 2012;994:97-104.

Rauter AP, et al. Efficient synthesis of alpha,beta-unsaturated gamma-lactones linked to sugars. Tetrahedron Asymmetry, 2001;12:1131-1146.

Hodge JE, Rist CE. The Amadori Rearrangement under New Conditions and its Significance for Non-enzymatic Browning Reactions2. J Am Chem Soc, 1953;75:316-322.

Sanchez-Fernandez EM, et al. Synthesis of Multibranched Australine Derivatives from Reducing Castanospermine Analogues through the Amadori Rearrangement of gem-Diamine Intermediates: Selective Inhibitors of beta-Glucosidase. J Org Chem, 2014;79:11722-11728.

Dai Z, et al. Identification of glucose-derived cross-linking sites in ribonuclease A. J Proteome Res, 2008;7:2756-2768.

Martin MJ, et al. Novel pyridodiindoles, azadiindoles, and indolopyridoimidazoles via the Fischer-indole cyclization. Heterocycles, 1993;36:157-189.

Rappaport Z, Liebman JF. The chemistry of hydroxylamines, oximes and hydroxamic acids. John Wiley & Sons, 2008, vol. 175.

Lawson AJ. Hetero-cope rearrangement via an isolable intermediate. J Chem Soc Chem Comm, 1979:456.

Overman LE. Mercury (II) and Palladium (II) Catalyzed [3,3] Sigmatropic Rearrangements [New Synthetic Methods (46)]. Angew Chem Int Ed Engl, 1984;23:579-586.

Perrin CL, Dwyer TJ. Application of 2-Dimensional Nmr to Kinetics of Chemical-Exchange. Chem Rev, 1990;90:935-967.

Lederer MO, et al. Cross-linking of proteins by maillard processes—Model reactions of d-glucose or methylglyoxal with butylamine and guanidine derivatives. Bioorg Med Chem, 1998;6:993-1002.

Mereyala HB, et al. Synthesis of (2S,4S)-4-Hydroxyproline from D-Glucose. Synthetic Commun, 2012;42:1278.

Kurhade SE, et al. A Phosphine-Mediated Synthesis of 1,4-Oxazepine- and 1,5 Oxazocine-Based Sugar Hybrids from Deoxysugar Azides. Synthesis-Struttgart, 2011;3523.

Draghici C, et al. Concise total synthesis of glucosepane. Science, 2015;350(6258):294-298.

Vincent M. Monnier et al.; Glucosepane: a poorly understood advanced glycation end product of growing importance for diabetes and its complications. Clinical Chemistry and Laboratory Medicine, 2014, 52(1): 21-32.

Oliver Reihl et al.; Pyridinium-carbaldehyde: active Maillard reaction product from the reaction of hexoses with lysine residues. Carbohydrate Research, 2004, 339:705-714.

Johan Svantesson Sjoberg et al.; Characteristics, formation and pathophysiology of glucosepane: A Major protein cross-link. Rejuvination Research, 2009, 12, 2, 137-149.

Markus O. Lederer et al.; Cross-linking of proteins by Maillard processes—characterization and detection of a lysine-arginine cross-link derived from D-glucose. Bioorganic & Medicinal Chemistry, 1999, 1081-1088.

Markus O. Lederer et al.; Cross-linking of proteins by Maillard processes—model reactions of D-glucose or methylglyoxal with butylamine and Guanidine Derivatives. Bioorganic & Medicinal Chemistry, 1998, 993-1002.

Rasoul Nasiri et al.; Theoretical studies on models of lysine-arginine cross-links derived from alpha-oxoaldehydes: new mechanism for glucosepane formation. J. Mol. Moded, 2012, 18:1645-1659.

Oliver Reihl et al.; Spiro cross-links: representatives of a new class of glycoxidation products. Journal of Agricultural and Food Chemistry, 2003,4810-4818.

\* cited by examiner

Scheme 1

Scheme 2

Scheme 3

Scheme 3A

SUBSTITUTED GLUCOSEPANES AND COMPOSITIONS THEREOF

RELATED APPLICATIONS

This application is a United States national phase patent application based upon International patent application number PCT/US2016/053407 of International filing date Sep. 23, 2016 entitled "The Total Synthesis of Glucosepane and Compounds Obtained Therefrom" which claims the benefit of support of U.S. provisional application No. U.S. 62/232,626, entitled "The total Synthesis of Glucosepane and Related Chemical Reactions", filed Sep. 25, 2015, the entire contents of which two said applications are incorporated by reference herein.

FIELD OF THE INVENTION

The present invention is directed to a novel, highly efficient total synthesis of glucosepane and related derivatives and chemical reactions which make this synthesis possible. In particular, methods of introducing an iso-imidazole moiety onto a substituted oxo-azepine precursor to provide glucosepane and derivatives thereof are disclosed. Additional embodiments of the present invention include compounds (for their biological activity and/or their use as synthetic intermediates, pharmaceutical compositions and methods of treatment as otherwise described herein.

BACKGROUND OF THE INVENTION

Post-translation modifications (PTMs) of proteins are responsible for a host of critical functions, ranging from accelerating protein folding to mediating protein-protein interactions.[1] Protein "glycation" is a non-enzymatic process for PTM formation wherein protein side-chains react spontaneously with open chain tautomers of carbohydrates. Mounting evidence suggests that protein glycation adducts, also called "advanced glycation end-products" or "AGEs", are critically involved in both healthy and disease processes, including inflammation, diabetes, cancer, and normal human aging.[2, 3] Notably, AGEs often possess highly complex chemical structures, impeding their detailed chemical and biological characterization.[4]

Glucosepane (1) is an important member of the AGE family that is both biologically and chemically significant (See FIG. 1). The molecule is formed as a "crosslink" from reaction sequences between arginine and lysine side-chains and one equivalent of hexose carbohydrate (most commonly glucose). Glucosepane is present on long-lived plasma proteins in the human body, such as collagen and lens crystallin,[3, 5] and is also found in high levels in various dietary sources, especially alkali-treated baked goods.[6] Researchers have speculated that glucosepane is directly involved in the pathophysiology of various conditions (e.g., diabetes, diabetes-related complications, and aging) due to patterns of glucosepane formation on disease-associated proteins. For example, analysis of skin biopsies obtained through the Diabetes Control and Complications Trial (DCCT) has determined that increases in skin glucosepane levels represent a significant, independent risk factor for the onset of diabetic nephropathy, retinopathy, and neuropathy.[3, 7] Additional studies have demonstrated that non-enzymatic glucosepane crosslinks outnumber enzyme-catalyzed crosslinks in human collagen in people over 65 years of age.[8] By age 100, glucosepane levels reach 2 nmol/mg collagen, which is almost ten times normal levels, whereas levels in diabetic patients can achieve up to twenty times those in healthy controls.[9, 10]

Several mechanisms have been proposed for glucosepane's involvement in disease complications. For example, researchers have hypothesized that glucosepane modification can decrease protein turnover rate and impair the renewal of damaged proteins. Glucosepane crosslinks may also be responsible for reported age- and diabetes-related decreases in collagen digestibility.[3],[11, 12],[13] Others have speculated that glucosepane-induced Arg modification can decrease the number of integrin binding sites in collagen, causing endothelial cell apoptosis, extracellular matrix deposition, and basement membrane thickening.[14] Glucosepane may also serve as ligand for pattern recognition receptors such as RAGE.[15] leading to chronic inflammation, or as a neoepitope that drives the breaking of self-tolerance against modified extracellular matrix proteins, serving as a trigger for the induction of autoimmune processes. Finally, due to high levels of glucosepane and other AGEs in the human diet, it has been suggested that these materials may function as uremic toxins, leading to complications in the setting of renal failure.(16)

Despite glucosepane's health implications, biological investigations have been hampered by a scarcity of chemically homogeneous material available for study. Its complex non-enzymatic biosynthesis involves serial tautomerizations of Amadori adduct 4 to provide glucosone 3 (a process termed "carbonyl mobility", FIG. 1B). During this process, each stereocenter undergoes epimerization, and therefore the glucosepane core exists in nature as a mixture of all eight possible diastereomers.[3],[17] These stereoisomers can only be chromatographically resolved into four binary mixtures, each containing two spectroscopically indistinguishable diastereomers with the same relative configuration at the 6, 7, and 8a positions, but opposite absolute configurations with respect to the enantiomerically pure backbone amino acids.[17] Despite significant effort, purification of stereochemically homogeneous glucosepane from biological samples has proven impossible. It is therefore unknown which of the eight stereoisomers is the most prevalent in vivo. Furthermore, these binary diastereomeric mixtures can only be isolated in low yields (0.2-1.4%) following model reactions between lysine, arginine and glucose, and extensive chromatographic purification.[17, 18] Importantly, because of these difficulties in purification, antibody reagents to enable biological detection of glucosepane in unprocessed tissue preparations are unavailable. To our knowledge, therefore, all published investigations into glucosepane biology have relied upon time-consuming extraction protocols, involving exhaustive enzymatic hydrolysis followed by HPLC purification. The development of synthetic routes toward chemically-defined glucosepane constructs represents an essential next step toward understanding the roles that this compound plays in human health and disease, and also toward the identification of novel therapeutic and/or diagnostic agents.

Glucosepane presents a deceptively challenging synthetic target due to its high density of heteroatoms, the presence of a stereogenic polyol motif incorporated within a fused hetero-bicyclic topology, an epimerizable stereocenter at C-8a, and perhaps most notably, the presence of an arginine-derived iso-imidazole at its core. Indeed, at first glance, one would expect glucosepane to tautomerize spontaneously to the corresponding aromatic imidazole (FIG. 1A); however, reported structural assignments of the iso-imidazole in glucosepane are consistent with one- and two-dimensional NMR data reported by Lederer and colleagues.[17] Furthermore, because glucosepane forms naturally as a protein adduct (not as the free bis-amino acid crosslink), any useful synthesis needs to be compatible with glucosepane incorporation into peptides. Also, because glucosepane is formed naturally as a mixture of all eight possible diastereomers, synthetic efforts targeting both enantio- and diastereomerically pure material are essential for detailed biochemical study.

BRIEF DESCRIPTION OF THE INVENTION

In one embodiment, the invention provides novel processes for making substantially pure glucosepane and substantially pure glucosepane derivatives in relatively large yields through syntheses that employ significantly fewer steps than known techniques.

In another embodiment, the invention provides novel processes for making various intermediates useful in the manufacture of pharmaceutically-active ingredients, including substantially pure glucosepane and substantially pure glucosepane derivatives.

In still another embodiment, the invention provides various novel compounds and intermediates useful in the manufacture of pharmaceutically-active ingredients, including substantially pure glucosepane and substantially pure glucosepane derivatives.

In still another embodiment, the invention provides methods of treating, inhibiting or reducing the likelihood of diabetes or a diabetes related disorder/secondary condition or inhibiting aging processes of the body administering either substantially pure glucosepane or a glucosepane derivative to a subject who suffers from, or who is at risk of developing, a disease state, disorder or aging processes as set forth above.

The present invention is directed to a method of synthesizing isoimidazoles, especially glucosepane according to the method which is set forth in scheme 3 herein (FIG. 5). The method comprises reacting an azepin-one compound with a semicarbazone to provide an intermediate compound (where R and X are as described generically below):

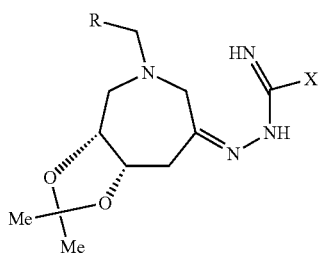

24A which can be reacted with a cyclizing agent (preferably trimethylsilyl chloride in solvent) to provide the compound:

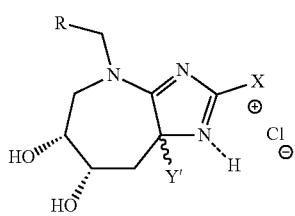

28A

Where Y' is H,
or a non-salt (free form), an alternative salt form or stereoisomer thereof.

Compound 28A can be further manipulated to provide compounds according to the present invention including the preferred glucosepane or an analog (in preferred embodiments, R is obtained from a lysine or ornithine amine acid, X is obtained from an ornithine or lysine amino acid and Y' is H.

Thus, in one embodiment, in the present method an azepin-one compound according the chemical structure (14)

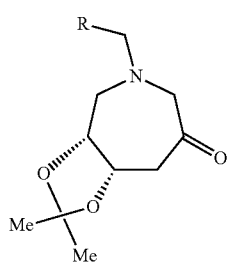

14 where R is a $C_1$-$C_{12}$ optionally substituted hydrocarbon group (preferably an optionally substituted alkyl or aryl group) or a heterocyclic group, preferably a heteroaryl group (in preferred aspects N—$CH_2$—R of the azepine ring is a lysine or ornithine moiety with the amine group formed from the distal amino groups of the side chain of the amino acid) is reacted according to scheme 3, FIG. 5 with a semicarbazone compound (which may be a salt form, depending on the conditions used) according to the chemical structure:

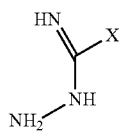

Where X is an optionally substituted S-alkyl (preferably, $C_3$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, O-heteroaryl), a $NR^1R^2$ group where $R^1$ and $R^2$ are each independently H (often, $R^2$ is H), an optionally substituted alkyl group (preferably, an optionally substituted $C_1$-$C_{12}$, preferably $C_1$-$C_7$ alkyl group including a $C_3$ or $C_4$ alkylene amino acid group obtained from lysine or ornithine, wherein the amino group and/or the carboxylic acid group is preferably protected), an optionally substituted aryl group or an optionally substituted heterocyclyl (preferably an optionally substituted heteroaryl), or (X is) an amino acid group preferably obtained from a D- or L-amino acid according to the chemical structure:

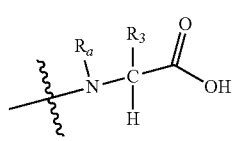

where the amine group of the amino acid is linked to the semicarbazone and the amine group and/or the carboxylic group is optionally protected and $R_a$ is H, $C_1$-$C_6$ alkyl or alkanol or $R_a$ forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), ornithine (propyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl), where the $R^3$ side chain is optionally protected. Preferably X is an optionally substituted S—($C_1$-$C_{12}$) alkyl (more preferably, S-Me), O—($C_1$-$C_{12}$) alkyl or a NH—$R^1$ group where $R^1$ is an optionally substituted $C_1$-$C_{12}$, preferably a $C_1$-$C_{10}$ alkyl group (preferably, NH$R^1$ is an ornithine or lysine moiety, which contains protecting groups) to provide compound 24A:

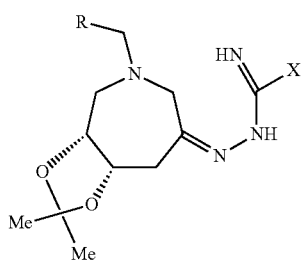

24A where R and X are the same as above;
Compound 24A is further reacted with trimethylsilyl chloride (TMSCl) in the presence of solvent (preferably chloroform, methylene chloride) at elevated temperature (generally, above room temperature and often at the reflux temperature of the solvent used) to provide compound 28A

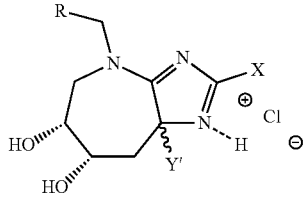

28A or an alternative pharmaceutical salt or neutral i.e. non-salt compound or stereoisomer thereof;
Where Y' is H and R and X are the same as above, preferably in one pot (compound 14 can be converted to compound 28A in a single pot and compound 24A can be converted to compound 28A in a single pot); and optionally, deprotecting the protected compound, which can be performed in the same pot or separated prior to deprotection. In this method, preferably N—CH$_2$—R of the azepine ring is a lysine or ornithine moiety with protecting groups on the amine and optionally the carboxylic acid moieties of R and X is NH$R^1$ as an ornithine or lysine moiety, also with optional protecting groups on the amine and optionally the carboxylic acid moieties on the ornithine and lysine moieties.

In certain embodiments of the present invention, in compound 28A, including where X is S-alkyl, even more preferably S-Me, Y' can be converted to a hydroxyl group using SiO$_2$ (FIG. 5, Scheme 3, compound 26 is converted to compound 27 using SiO$_2$) or triethylamine in acetonitrile/water (FIG. 6 Scheme 3A) and the intermediate compound (Y' is OH, X is as described above, preferably S-Me of FIG. 5, Scheme 3) can be deprotected or further reacted with an amine (including an amino acid derivative), preferably a protected ornithine or lysine amino acid (the amine on the side chain is unprotected, with the amine group and optionally the carboxylic acid of the amino acid group being protected, preferably with a Cbz or other protecting group) to introduce the amine into the compound as a substituent on the isoimidazole moiety (see compound 28A above or compound 28 of FIG. 5, Scheme 3), followed by reduction, preferably with a borohydride (e.g. Na(OAc)$_3$BH) or other reducing agent (to convert Y' as OH to H) to produce a compound where X is as described above, preferably an amine, more preferably a protected orninthine or lysine group (protecting group at least on the amine) which compound may be subsequently deprotected to provide compound 28A, Y' is H, NCH$_2$R is a lysine or ornithine (preferably lysine) moiety and X is a lysine or ornithine (preferably ornithine) moiety. The protecting groups may be removed pursuant to the selectivity of the protecting group to removal as described herein, consistent with otherwise maintaining the integrity of the chemistry of the compound.

In preferred aspects, the formation of compound 28A from compound 14 occurs in a single pot reaction in high yield (often greater than 50%, 55%, 60%, 65%, 70%, 75%, 80%, 85%, 90%, 95% and higher).

In certain preferred aspects of the present invention, compound 14 (where N—CH$_2$—R of the azepine ring is a lysine or ornithine moiety, preferably a lysine moiety, with the amine group formed from the distal amino groups of the side chain of the amino acid) is reacted with a semicarbazone of the chemical structure:

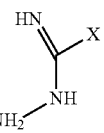

Where X is an optionally substituted S-alkyl (preferably, $C_1$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, S-heteroaryl), a N$R^1R^2$ group where $R^1$ and $R^2$ are each independently H (often. $R^2$ is H), an optionally substituted alkyl group (preferably, a $C_1$-$C_7$ alkyl group or an amino acid group obtained from lysine or ornithine), an optionally substituted aryl group or an optionally substituted heterocyclyl (preferably an optionally substituted heteroaryl), or (X is) an amino acid group preferably obtained from a D- or L-amino acid according to the chemical structure:

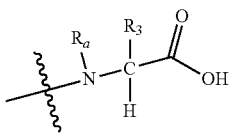

where the amine group of the amino acid is linked to the semicarbazone and the amine group and/or the carboxylic group is optionally protected and $R_a$ is H, $C_1$-$C_6$ alkyl or alkanol or $R_a$ forms a cyclic ring with $R^3$ (proline or hydroxyl proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl) (where the $R^3$ side chain is optionally protected). Preferably X is an optionally substituted S-alkyl (preferably, S-Me) or a NH—$R^1$ group where $R^1$ is an ornithine or lysine moiety, which contains protecting groups on the amine and carboxylic acid groups) react to form the compound 24A

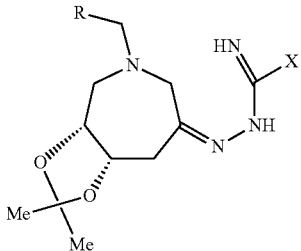

where R and X are the same as above;
Compound 24A is further reacted with trimethylsilyl chloride (TMSCl) in the presence of solvent (preferably chloroform) at elevated temperature (generally, above room temperature and often at the reflux temperature of the solvent used) to provide compound 28A:

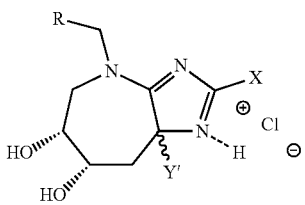

Or an non-salt form, alternative salt form or stereoisomer thereof,
Where Y' is H and R and X are the same as above (preferably N—CH$_2$—R of the azepine ring is a lysine or ornithine moiety and X is NHR$^1$ as an ornithine or lysine moiety as described herein); and optionally, deprotecting the protected compound. In preferred aspects, the formation of compound 28A from compound 14 occurs in a single pot reaction in high yield (often greater than 50%, 55%, 60%, 70%, 80% and higher). Note that compound 28A may also be in a non-salt or alternative salt form or as one of a number of stereoisomers, including a diastereomer or enantiomer).

Compound 28A may be converted such that Y' is OH by reacting compound 28A with SiO2 or triethylamine in aqueous solvent (aqueous acetonitrile) to convert Y' as H to OH. When Y' is OH, the hydroxyl group may be converted back to a hydrogen group by reducing the hydroxyl to hydrogen using a reducing agent, preferably a borohydride reducing agent (e.g. Na(OAc)$_3$BH). In certain embodiments (preferably where X is S-alkyl, especially SMe), X may also be substituted by an amine, preferably an amino acid, including an ornithing or lysine group (attachment is on the distal amine of the side chain) as otherwise described herein.

In another embodiment (see FIG. 3, Scheme 1 and FIG. 5, Scheme 3), the present invention relates to a total synthesis of glucosepane from the readily available epoxide starting material 8

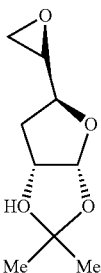

Comprising exposing compound 8 to a protected amine, preferably a protected amino acid (preferably a lysine or ornithine derivative) according to the chemical structure:

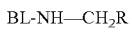

where R is an optionally substituted $C_1$-$C_{12}$ hydrocarbon group (preferably an optionally substituted alkyl or aryl group, preferably phenyl) or an optionally substituted heterocycle group (preferably, a heteroaryl group), preferably R is an alkylene amino acid group (preferably from lysine or ornithine which is protected on the amine and carboxylic acid groups of the amino acid)
and BL is a protecting group (preferably, a Dod blocking/ protecting group or other protecting group which does not impair or prevent the amine group reacting with the epoxide of compound 8) in the presence of solvent (preferably ethanol, isopropanol) at elevated temperature in a first step followed by strong acid, preferably a trifluoroacetic acid solution (e.g. 5%) in solvent (preferably, methylene chloride, chloroform) in the presence of anisole and a hydrosilane (preferably iPr$_3$SiH or other trialkylhydrosilane) to provide compound 10:

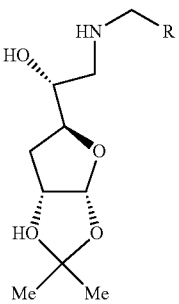

Where R is the same as described above;
Compound 10 is thereafter exposed to aqueous acid (preferably 70% aqueous acetic acid or other organic acid at elevated temperature) to provide compound 11 (FIG. 3, scheme1), which spontaneously undergoes amadori rearrangement and intramolecular trapping to provide compound 13:

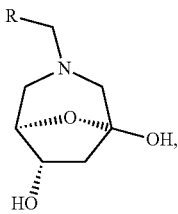

which is reacted with 2,2-dimethoxypropane (DMP) in the presence of pyridinium p-toluenesulfonate (PPTS) in solvent (toluene) to provide dihydroxy protected compound 14, which can then be reacted with the semicarbazone as described above (especially compound 22 or 23 of FIG. 5, Scheme 3 A, followed by reaction with trimethylsilylchloride (TMSCl) at elevated temperature and deprotection of any protecting groups to provide compound 28A

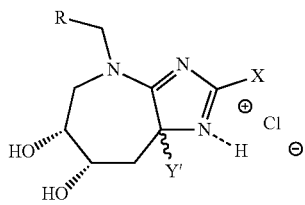

Where X and R are the same as above and Y' is H (or the non-salt or alternative salt thereof or a stereoisomer thereof).

In preferred aspects, where the semicarbazone is compound 22 or 23 (FIG. 5, Scheme 3A.), X is SMe, HN-Orn or HN-Lys (the lysine is protected in an analogous manner to HN-Orn, depicted) and Y' is H (or the free amine or alternative salt thereof) (see compounds 26 or 28 of FIG. 5, scheme 3), which compounds can then be deprotected to provide the final deprotected compounds.

In certain preferred aspects, compound 26

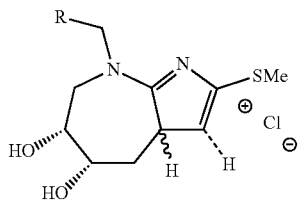

is reacted with SiO2 or triethylamine in aqueous solvent (e.g. acetonitrile/water) to provide a hydroxyl substituted compound 27 (FIG. 5, Scheme 3, and FIG. 6, scheme 3A, the bridge hydrogen is replaced with a hydroxyl group) which may be further reacted with a protected ornithine (or analogous lysine derivative) or other amine (which is optionally protected) optionally in a weak base (e.g. triethylamine) followed by borohydride reduction (preferably Na(OAc₃)BH) to produce an ornithine (or lysine/amine) compound 28 which is subsequently optionally deprotected, for example using reduction or other conditions to remove any protecting groups to provide a final deprotected compound.

As discussed above, compound 26

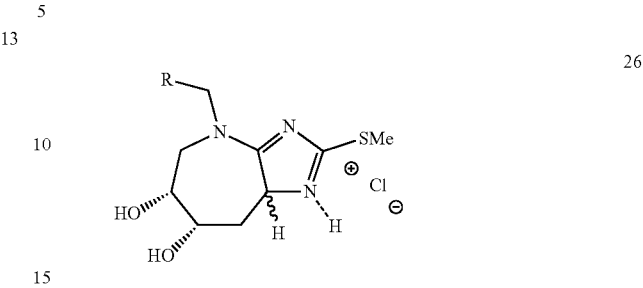

is alternatively reacted with SiO$_2$ or in weak base (e.g. triethyl amine) in aqueous solvent (e.g. acetonile or other polar solvent) to provide compound 27 (the bridge hydrogen is converted to hydroxyl). Compound 27 can be converted to compound 28 by reacting compound 27 with a protected ornithine, lysine or other amine followed by borohydride reduction of the bridge hydroxyl to hydrogen and subsequently deprotecting any protecting group(s) to provide the final deprotected compound (or its non-salt, alternative salt or a stereoisomer thereof).

A large number of glucosepane derivatives may be made by the same method. Note that compound 28A is in equilibrium with its free amine (i.e. non-salt form) and can be found in its free amine or as an alternative salt form, as well as in a number of stereoisomeric forms.

In still another embodiment, the present invention is directed to a method for synthesizing an optionally substituted imidazole from an aldehyde or ketone of the general formula 1k:

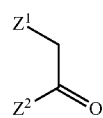

Where $Z^1$ is H, an optionally substituted $C_1$-$C_{12}$ hydrocarbon group (preferably an alkyl, alkenyl or aryl group), a 3-20 membered (preferably, a 5- to 20-membered) heterocyclic group (preferably, a heteroaryl group), a $NR^1R^2$ group, a $SR^1$ or $OR^1$ group or together $Z^1$ and $Z^2$ link to form an optionally substituted 5- to 8-membered ring (with the carbonyl and methylene group) which ring is carbocyclic or heterocyclic, including one or more unsaturated bonds, aryl or heteroaryl;

$Z^2$ is H, an optionally substituted $C_1$-$C_{12}$ hydrocarbon group (preferably an alkyl, alkenyl or aryl group), a 3-20 membered (preferably, a 5- to 20-membered) heterocyclic group (preferably, a heteroaryl group) or together $Z^1$ and $Z^2$ are linked to form an optionally substituted 5- to 8-membered ring (preferably, a 6- or 7-membered ring) which is carbocyclic or heterocyclic, including aryl or heteroaryl;

$R^1$ and $R^2$ are each independently absent (only one of $R^1$ and $R^2$ may be absent), H, an optionally substituted $C_1$-$C_6$ alkyl, alkene or alkyne group, an optionally substituted aryl or heterocyclic group (preferably, including a heteroaryl group) or $NR^1R^2$ is an optionally protected amino acid group where $R^1$ is H or a $C_1$-$C_3$ alkyl group and $R^2$ is a group preferably obtained from a D- or L-amino acid according to the chemical structure:

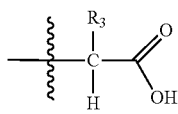

where $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), ornithine (propyleneamine), methionine (ethylmethylthioether), phenylalanine (benzyl), proline ($R^3$ forms a cyclic ring with the adjacent nitrogen group when $R^1$ is H to form a pyrrolidine group), hydroxyproline, serine (methanol), threonine (ethanol, 1-hydroxyethane), tryptophan (methyleneindole), tyrosine (methylene phenol) or valine (isopropyl), The method comprising reacting a compound of formula 1i with a semicarbazone compound of formula S1:

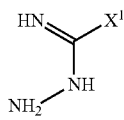

Where $X^1$ is an optionally substituted S-alkyl (preferably, $C_1$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, S-heteroaryl), a $NR^1R^2$ group where $R^1$ and $R^2$ are each independently H (often, $R^2$ is H), an optionally substituted $C_1$-$C_{12}$ alkyl group (preferably, a $C_1$-$C_7$ alkyl group or an amino acid group obtained from lysine or ornithine), an optionally substituted aryl group or an optionally substituted heterocyclyl (preferably an optionally substituted heteroaryl), or (X is) an amino acid group preferably obtained from a D- or L-amino acid

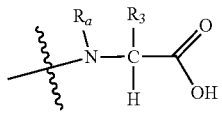

where the amine group of the amino acid is linked to the semicarbazone and the amine group and/or the carboxylic group is optionally protected and $R_a$ is H, $C_1$-$C_6$ alkyl or alkanol or $R_a$ forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl) (where the $R^3$ side chain and/or the carboxylic acid group is optionally protected) to obtain a compound of the formula 1ia:

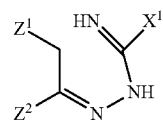

or its salt (preferably a pharmaceutically acceptable salt) where $Z^1$, $Z^2$ and $X^1$ are the same as above, which is thereafter reacted with trimethylsilyl chloride in solvent (e.g. chloroform) at elevated temperature to obtain the compound 1i

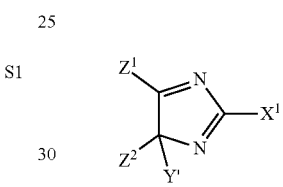

(as a hydrochloride salt, non-salt or alternative salt form), Where Y' is H, and
Wherein said compound is optionally and preferably deprotected.

In further embodiments, Y' in the above imidazole may be converted to a hydroxyl group in $SiO_2$ or weak base (triethylene amine) in aqueous solvent (preferably acetonitrile). In addition, the $X^1$ substituent (e.g. S-alkyl) may be converted to another substituent (for example, especially with an amine).

The present invention is also directed to compounds according to the chemical structure (or a salt form):

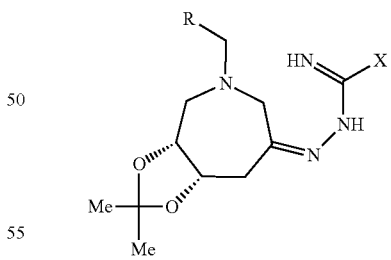

where R is a $C_1$-$C_{12}$ optionally substituted hydrocarbon group (preferably an optionally substituted alkyl or aryl group) or a heterocyclic group, preferably a heteroaryl group (in preferred aspects N—$CH_2$—R of the azepine ring is a lysine or ornithine moiety with the amine group formed from the distal amino groups of the side chain of the amino acid); and X is optionally substituted S-alkyl (preferably, $C_1$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, S-heteroaryl), a $NR^1R^2$ group where $R^1$ and $R^2$ are each independently H (often, $R^2$ is H), an optionally substituted alkyl group (preferably, a $C_1$-$C_7$ alkyl group or an amino acid group obtained from lysine or ornithine), an optionally substituted aryl group or an optionally substituted heterocyclyl (preferably an optionally substituted heteroaryl), or (X is) an amino acid group preferably obtained from a D- or L-amino acid according to the chemical structure:

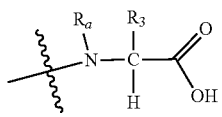

where the amine group of the amino acid is linked to the semicarbazone and the amine group and/or the carboxylic group is optionally protected and $R_a$ is H, $C_1$-$C_6$ alkyl or alkanol or $R_a$ forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl) (where the $R^3$ side chain is optionally protected). Preferably X is an optionally substituted S—($C_1$-$C_{12}$) alkyl (preferably, S-Me), O—($C_1$-$C_{12}$) alkyl or a NH—$R^1$ group where $R^1$ is an optionally substituted $C_1$-$C_{12}$, preferably a $C_1$-$C_{10}$ alkyl group (preferably, NHR$^1$ is an ornithine or lysine moiety,
or a salt form) especially including a pharmaceutically acceptable salt form), stereoisomer (including a diastereomer or enantiomer), solvate or polymorph thereof.

In another embodiment, the present invention is directed to compounds according to the chemical structure:

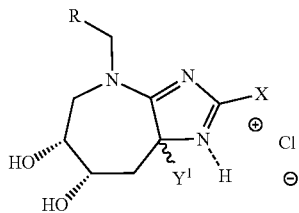

Or a non-salt, alternative salt form or stereoisomer thereof, Where R is a $C_1$-$C_{12}$ optionally substituted hydrocarbon group (preferably an optionally substituted alkyl or aryl group) or a heterocyclic group, preferably a heteroaryl group (in preferred aspects N—CH$_2$—R of the azepine ring is a lysine or ornithine moiety with the amine group formed from the distal amino groups of the side chain of the amino acid); X is optionally substituted S-alkyl (preferably, $C_1$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, S-heteroaryl), a $NR^1R^2$ group where $R^1$ and $R^2$ are each independently H (often, $R^2$ is H), an optionally substituted alkyl group (preferably, a $C_1$-$C_7$ alkyl group or an amino acid group obtained from lysine or ornithine), an optionally substituted aryl group or an optionally substituted heterocyclyl (preferably an optionally substituted heteroaryl), or (X is) an amino acid group preferably obtained from a D- or L-amino acid according to the chemical structure:

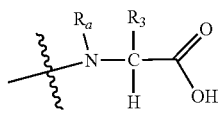

where the amine group of the amino acid is linked to the semicarbazone and the amine group and/or the carboxylic group is optionally protected and $R_a$ is H, $C_1$-$C_6$ alkyl or alkanol or $R_a$ forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl) (where the $R^3$ side chain is optionally protected). Preferably X is an optionally substituted S—($C_1$-$C_{12}$) alkyl (preferably, S-Me), O—($C_1$-$C_{12}$) alkyl or a NH—$R^1$ group where $R^1$ is an optionally substituted $C_1$-$C_{12}$, preferably a $C_1$-$C_{10}$ alkyl group; and
Y is H or OH;
with the proviso that X, R and Y' do not form glucosepane
or
a non-salt or alternative salt form, stereoisomer, solvate or polymorph thereof.

In yet another embodiment, the present invention is directed to compounds according to the chemical structure:

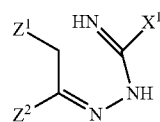

Where $Z^1$ is H, an optionally substituted $C_1$-$C_{12}$ hydrocarbon group (preferably an alkyl, alkenyl or aryl group), a 3-20 membered (preferably, a 5- to 20-membered) heterocyclic group (preferably, a heteroaryl group), a $NR^1R^2$ group, a $SR^1$ or $OR^1$ group or together $Z^1$ and $Z^2$ link to form an optionally substituted 5- to 8-membered ring (with the carbonyl and methylene group) which ring is carbocyclic or heterocyclic, including one or more unsaturated bonds, aryl or heteroaryl;

$Z^2$ is H, an optionally substituted $C_1$-$C_{12}$ hydrocarbon group (preferably an alkyl, alkenyl or aryl group), a 3-20 membered (preferably, a 5- to 20-membered) heterocyclic group (preferably, a heteroaryl group) or together $Z^1$ and $Z^2$ are linked to form an optionally substituted 5- to 8-membered ring (preferably, a 6- or 7-membered ring) which is carbocyclic or heterocyclic, including aryl or heteroaryl;

$R^1$ and $R^2$ are each independently absent, H, an optionally substituted $C_1$-$C_6$ alkyl, alkene or alkyne group, an optionally substituted aryl or heterocyclic group (preferably, including a heteroaryl group) or $NR^1R^2$ is an optionally protected amino acid group where $R^1$ is H or a $C_1$-$C_3$ alkyl group and $R^2$ is a group preferably obtained from a D- or L-amino acid according to the chemical structure:

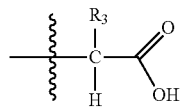

where $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methylencimidazole), isoleucine (1-methylpropane), leucine (2-methylpropane), lysine (butyleneamine), ornithine (propyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl); and $X^1$ is an optionally substituted S-alkyl (preferably, $C_1$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, S-heteroaryl) or a $NR^1R^2$ group where $R^1$ and $R^2$ are each independently H (often, $R^2$ is H), an optionally substituted alkyl group (preferably, a $C_1$-$C_7$ alkyl group or an amino acid group obtained from lysine or ornithine), an optionally substituted aryl group or an optionally substituted heterocyclyl (preferably an optionally substituted heteroaryl), or (X is) an amino acid group preferably obtained from a D- or L-amino acid according to the chemical structure:

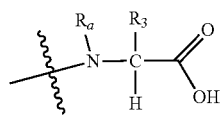

where the amine group of the amino acid is linked to the semicarbazone and the amine group and/or the carboxylic group is optionally protected and $R_a$ is H, $C_1$-$C_6$ alkyl or alkanol or R forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl) (where the $R^3$ side chain is optionally protected). Preferably X is an optionally substituted S—($C_1$-$C_{12}$) alkyl (preferably, S-Me), O—($C_1$-$C_2$) alkyl or a NH—$R^1$ group where $R^1$ is an optionally substituted $C_1$-$C_{12}$, preferably a $C_1$-$C_{10}$ alkyl group (preferably, $NHR^1$ is an ornithine or lysine moiety, or a salt form) especially including a pharmaceutically acceptable salt form), stereoisomer (including a diastereomer or enantiomer), solvate or polymorph thereof.

In still further embodiments, the present invention is directed to compounds according to the chemical structure:

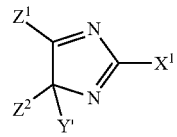

Where $Z^1$ is H, an optionally substituted $C_1$-$C_2$ hydrocarbon group (preferably an alkyl, alkenyl or aryl group), a 3-20 membered (preferably, a 5- to 20-membered) heterocyclic group (preferably, a heteroaryl group), a $NR^1R^2$ group, a $SR^1$ or $OR^1$ group or together $Z^1$ and $Z^2$ link to form an optionally substituted 5- to 8-membered ring which ring is carbocyclic or heterocyclic, including one or more unsaturated bonds, aryl or heteroaryl;

$Z^2$ is H, an optionally substituted $C_1$-$C_{12}$ hydrocarbon group (preferably an alkyl, alkenyl or aryl group), a 3-20 membered (preferably, a 5- to 20-membered) heterocyclic group (preferably, a heteroaryl group) or together $Z^1$ and $Z^2$ are linked to form an optionally substituted 5- to 8-membered ring (preferably, a 6- or 7-membered ring) which is carbocyclic or heterocyclic, including aryl or heteroaryl;

$R^1$ and $R^2$ are each independently absent, H, an optionally substituted $C_1$-$C_6$ alkyl, alkene or alkyne group, an optionally substituted aryl or heterocyclic group (preferably, including a heteroaryl group) or $NR^1R^2$ is an optionally protected amino acid group where $R^1$ is H or a $C_1$-$C_3$ alkyl group and $R^1$ is a group preferably obtained from a D- or L-amino acid according to the chemical structure:

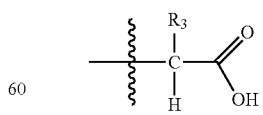

where $R^3$ is a side chain derived from an amino acid preferably selected from the group consisting of alanine (methyl), arginine (propyleneguanidine), asparaginc (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), ornithine (propyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

$X^1$ is an optionally substituted S-alkyl (preferably, $C_1$-$C_7$ alkyl, preferably, S-Me or an amino acid group obtained from cysteine), an optionally substituted S-aryl or an optionally substituted S-heterocyclyl (preferably, S-heteroaryl), an optionally substituted O-alkyl (preferably, $C_1$-$C_7$ alkyl, preferably, O-Me or an amino acid group obtained from serine), an optionally substituted O-aryl (or an optionally substituted O-heterocyclyl (preferably, S-heteroaryl), a $NR^1R^2$ group where $R^1$ and $R^2$ are each independently H (often, $R^2$ is H), an optionally substituted alkyl group (preferably, a $C_1$-$C_7$ alkyl group or an amino acid group obtained from lysine or ornithine), an optionally substituted aryl group or an optionally substituted heterocyclyl (preferably an optionally substituted heteroaryl), or (X is) an amino acid group preferably obtained from a D- or L-amino acid according to the chemical structure:

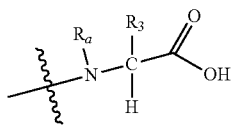

where the amine group of the amino acid is linked to the semicarbazone and the amine group and/or the carboxylic group is optionally protected and $R_a$ is H, $C_1$-$C_6$ alkyl or alkanol or $R_a$ forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl) (where the $R^3$ side chain is optionally protected). Preferably X is an optionally substituted S—($C_1$-$C_{12}$) alkyl (preferably, S-Me), O—($C_1$-$C_{12}$) alkyl or a NH—$R^L$ group where $R^1$ is an optionally substituted $C_1$-$C_{12}$, preferably a $C_1$-$C_{10}$ alkyl group (preferably, $NHR^1$ is an ornithine or lysine moiety; and Y' is H or OH (preferably OH), or a salt form (especially including a pharmaceutically acceptable salt form), stereoisomer (including a diastereomer or enantiomer), solvate or polymorph thereof.

In additional embodiments, the present invention is directed to a pharmaceutical composition comprising an effective amount of a compound as set forth above in combination with a pharmaceutically acceptable carrier, additive and/or excipient, including an additional bioactive agent, especially a bioactive agent useful in the treatment of a diabetic disorder or to inhibit or treat disorders related to the aging process as otherwise described herein.

In still further embodiments, the present invention is directed to a method for treating a diabetic disorder or treating aging and/or disorders related to the aging process in a patient in need comprising administering a pharmaceutical composition in an effective amount to said patient. Diabetic disorders which may be treated using pharmaceutical compositions according to the present invention include type I and type II diabetes, insulin resistance, glucose intolerance, insulin resistance syndrome, metabolic syndrome and related disease states and conditions including cardiovascular diseases associated with same, hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia, as well as disorders such as infections, varicose veins, acanthosis nigricans, eczema, exercise intolerance, hypercholesterolemia, cholelithiasis, orthopedic injury and thromboembolic disease.

Additional embodiments of the present invention may be readily gleaned from a review of the detailed description of the present invention, set forth herein below.

DETAILED DESCRIPTION OF THE INVENTION

Figure 1:
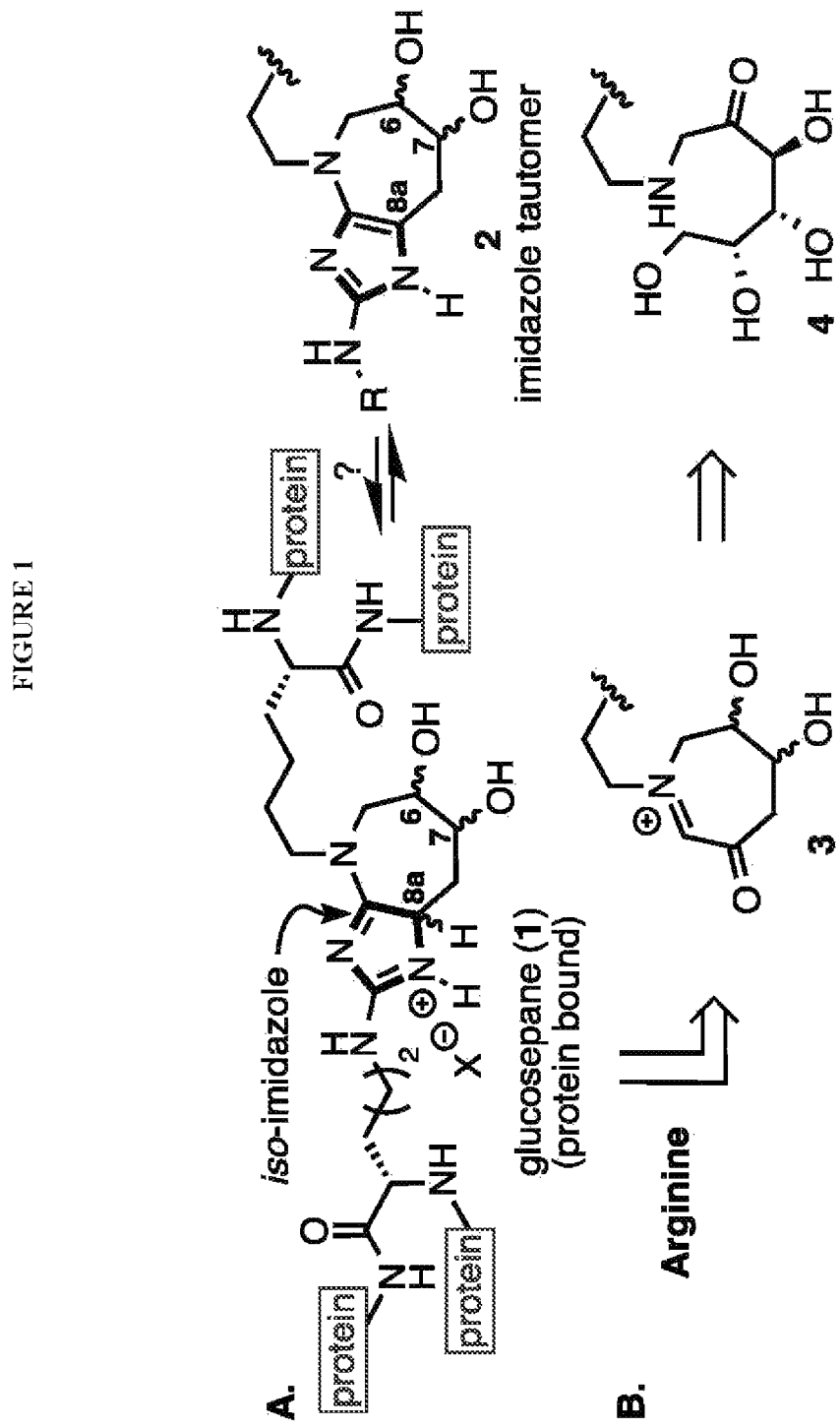
FIG. 1 shows glucosepane and the iso-imidazole. (A) Chemical structure of the protein-bound glucosepane crosslink, depicting both non-aromatic iso-imdazole (1) and aromatic imidazole (2) tautomers. (B) Proposed biosynthetic pathway for glucosepane crosslinks.

In accordance with the present invention there may be employed conventional chemical synthetic and pharmaceutical formulation methods, as well as pharmacology, molecular biology, microbiology, and recombinant DNA techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "an", "and" and "the" include plural references unless the context clearly dictates otherwise.

The following terms, among others, are used to describe the present invention. It is to be understood that a term which is not specifically defined is to be given a meaning consistent with the use of that term within the context of the present invention as understood by those of ordinary skill.

The term "compound", as used herein, unless otherwise indicated, refers to any specific chemical compound disclosed herein and includes tautomers, regioisomers, geometric isomers, and where applicable, optical isomers (e.g. enantiomers), stereoisomers (e.g., diastereomers, such term also subsuming enantiomers and other diastereomers) thereof, as well as pharmaceutically acceptable salts and alternative salt forms as well as non-salt forms (depending upon the environment and/or pH in which the compound is found) and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

As used herein, the term "glucosepane" means a composition comprising about at least about 50%, at least about 55%, at least about 60%, preferably at least about 75%, at least about 80%, 85%, 90%, 95%, 98%, 99% and 99+% pure glucosepane (see compound 1 of FIG. 1). Note that a glucosepane mixture may contain up to 8 enantiomeric and diastereomeric forms of glucosepane. A glucosepane derivative is defined similarly with respect to the relative amounts of its isomers (enantiomers and/or diastereomers) in the final mixture of the composition. The term "stereoisomer" is used to refer to each of the up to 8 enantiomers and diastereomeric forms of glucosepane, as well as other stereisomers of glucosepane.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal.

The symbol ═ is used in chemical compounds according to the present invention to signify that a bond between atoms is a single bond or double bond according to the context of the bond's use in the compound, which depends on the atoms (and substituents) used in defining the present compounds. Thus, where a carbon (or other) atom is used and the context of the use of the atom calls for a double bond or single bond to link that atom with an adjacent atom in order to maintain the appropriate valence of the atoms used, then that bond is considered a double bond or a single bond.

A diabetic disorder includes type I and type II diabetes, insulin resistance, glucose intolerance, insulin resistance syndrome, metabolic syndrome and related disease states and conditions including cardiovascular diseases associated with same, hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia, as well as disorders such as infections, varicose veins, acanthosis *nigricans*, eczema, exercise intolerance, hypercholesterolemia, cholelithiasis, orthopedic injury and thromboembolic disease.

The term "effective" is used herein, unless otherwise indicated, to describe an amount of a compound or composition which, in context, is used to produce or effect an intended result, whether that result relates to the inhibition of the effects of diabetes or a diabetic condition or disorder, to inhibit or reverse the effects of aging, or to potentiate the effects of a supplementary treatment used in treating diabetes or a diabetic condition or disorder or the effects of aging. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for or afflicted by a diabetic disorder or condition, including lessening or suppression of at least one symptom of diabetes or a diabetic disorder, delay in progression of diabetes, a diabetic disorder or the effects of aging. Treatment, as used herein within context, may encompass both prophylactic and therapeutic treatment depending on the context of the use of the term. Treatment is established through the use of the term "treating" or "inhibiting" whereas prophylaxis is usually established through the use of the term "reducing the likelihood of".

The term "pharmaceutically acceptable salt" or "salt" is used throughout the specification to describe a salt form of one or more of the compositions herein which are presented preferably to increase the solubility of the compound in a solvent, for example, in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, the term "salt" shall mean a pharmaceutically acceptable salt, consistent with the use of the compounds as pharmaceutical agents.

The term "co-administration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, or at slightly different intervals, the term embraces both administration of two or more agents at the same time or at different times, including sequential administration. Preferably, effective concentrations of all co-administered compounds or compositions are found in the subject at a given time.

For example, compounds according to the present invention may be administered with one or more agents that are useful in treating diabetes or a diabetic disorder or have an effect on the process of aging in a patient. The type of co-administered agent can vary widely depending on the particular clinical context. For example, co-administered agents can include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, phosphodiesterase inhibitors, cholesterol/lipid lowering agents and lipid profile therapies, traditional anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, anti-fungal agents and mixtures thereof.

In the case of Type II diabetes, useful additional agents include but are not limited to biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2), glucagon-like peptide-1 (GLP-1), and dipeptidyl peptidase IV (DP4) inhibitors and mixtures thereof.

The term "acyl" is art-recognized and refers to a group represented by the general formula hydrocarbylC(O)—, preferably alkylC(O)—.

The term "acylamino" is art-recognized and refers to a moiety having an amino group and an acyl group and may include substituents on same as otherwise disclosed herein. The term "alkylamino" refers to an amino group and an optionally substituted alkyl group on same as otherwise described herein. "Dialkyl amino refers to an amino group and two optionally substituted alkyl groups.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group. The term "alkenyl", as used herein, refers to an optionally substituted aliphatic group containing at least one double bond, the substituted alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed herein, except where stability of the moiety is prohibitive. For example, substitution of alkenyl groups by one or more alkyl, carbocyclyl, aryl, heterocyclyl, or heteroaryl groups, among others is contemplated.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$-substituent, where m is 0 to 10, preferably 1 to 6, and the substituent is an aryl or substituted aryl group, a cycloalkyl group, a cycloalkenyl, a heterocycle or a polycycle (two or three ringed), each of which may be optionally substituted.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 10 or fewer carbon atoms in its backbone (e.g., $C_1$-$C_{12}$ for straight chains, $C_1$-$C_{12}$ for branched chains), and more preferably 8-10 or fewer ($C_1$-$C_{10}$), and most preferably 6 or fewer ($C_1$-$C_6$). Likewise, preferred cycloalkyls have from 3-10 carbon atoms in their ring structure, and more preferably have 5, 6, 7 or 8 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, alkoxy ($C_1$-$C_8$, preferably $C_1$-$C_6$) a carbonyl $C_1$-$C_8$ (such as a carboxyl, an alkoxycarbonyl ester, an oxycarbonyl ester, a formyl, or an acyl), a thiocarbonyl (such as a thioester, a thioacetate, or a thioformate), a phosphoryl, a phosphate, a phosphonate, a phosphinate, an amino, including an amino in combination with a carboxylic acid (e.g., forming an amino acid sidechain such as an ornithine or lysine sidechain), an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety or as otherwise described herein. It will be understood by those skilled in the art that the individual substituent chemical moieties can themselves be substituted. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN, nitro and the like. Exemplary, non-limiting substituted alkyls are described herein. Cycloalkyls can be further substituted with alkyls, alkenyls, alkynyls, alkoxys, alkylthios, aminoalkyls, carbonyl-substituted alkyls, —$CF_3$, —CN, nitro, alkoxy and the like.

Analogous substitutions can be made to alkenyl and alkynyl groups to produce, for example, without limitation, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to eight carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$-substituent, wherein m is 0 or an integer from 1 to 12, preferably 1 to 8 and substituent is the same as defined herein and as otherwise below ($R_9$ and $R_{10}$ for amine/amino). Representative alkylthio groups include methylthio, ethylthio, and the like.

The terms "amine" and "amino" are art-recognized and refer to both unsubstituted and substituted amines, e.g., a moiety that can be represented, without limitation, by the general formula:

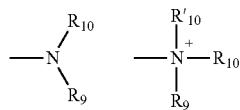

wherein $R_9$, $R_{10}$ and $R'_{10}$ each independently represent a hydrogen, an optionally substituted alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle, including a heteroaryl or a polycycle, and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally, $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group. Each of the groups which is bonded to the amine group, where applicable, may be optionally substituted. In certain preferred aspects the amine together with its substituent forms a lysine or ornithine radical.

The term "amido" is art-recognized as an amino-substituted carbonyl and includes a moiety that can be represented by the general formula:

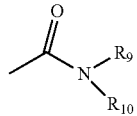

wherein $R_9$, $R_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein inn context includes 5-, 6-, and 7-membered single-ring or aromatic groups which contain from zero to four heteroatoms depending on the context of the term use, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl groups". The aromatic ring can be substituted at one or more ring positions with such substituents as otherwise described herein, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

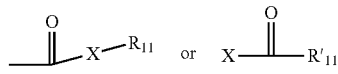

wherein X is a bond or represents an oxygen or a sulfur, and $R_{11}$ represents, for example without limitation, a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m (0-8) and $R_8$ are as otherwise described herein without limitation. Where X is oxygen and $R_{11}$ or $R'_{11}$ is not hydrogen, the formula represents an "ester". Where X is oxygen, and $R_{11}$ is as defined above, the moiety is referred to herein as a carboxyl group, and particularly when $R_{11}$ is hydrogen, the formula represents a "carboxylic acid". Where X is oxygen, and $R'_{11}$ is hydrogen, the formula represents a "formate". In general, where the oxygen atom of the above formula is replaced by sulfur, the formula represents a "thiocarbonyl" group. Where X is sulfur and $R_{11}$ or $R'_{11}$ is not hydrogen, the formula represents a "thioester." Where X is sulfur and $R_{11}$ is hydrogen, the formula represents a "thiocarboxylic acid." Where X is sulfur and $R'_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "electron withdrawing group" refers to chemical groups which withdraw electron density from the atom or group of atoms to which electron withdrawing group is attached. The withdrawal of electron density includes withdrawal both by inductive and by delocalization/resonance effects. Examples of electron withdrawing groups attached to aromatic rings include perhaloalkyl groups, such as trifluoromethyl, halogens, azides, carbonyl containing groups such as acyl groups, cyano groups, and imine containing groups. The term "electron contributing group" refers to chemical groups which donate electron density to the atom or group of atoms to which the electronic donating group is attached. Examples of such groups include the alkoxy and amine groups, among others.

The term "ester", as used herein, refers to a group —C(O)O-substituent wherein the substituent represents, for example, a hydrocarbyl or other substitutent as is otherwise described herein.

The terms "halo" and "halogen" as used herein means halogen and includes chloro, fluoro, bromo, and iodo.

The terms "hetaroalkyl" and "heteroaralkyl", as used herein, refers to an alkyl group substituted with a hetaryl group.

The terms "heterocycle" or "heterocyclic group" refer to 3- to 10-membered ring structures, more preferably 3- to 7-membered rings, whose ring structures include one to four heteroatoms. Heterocycles can also be polycycles and can include up to 20 member polycyclic ring systems. Heterocyclyl groups include, for example, without limitation, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above without limitation, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like, and as otherwise described herein.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also may include up to 20-membered polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

Thus, the terms "heterocyclyl", "heterocycle", and "heterocyclic" refer to substituted or unsubstituted aromatic or non-aromatic ring structures (which can be cyclic, bicyclic or a fused ring system), preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "5- to 20-membered heterocyclic group" or "5- to 14-membered heterocyclic group" as used throughout the present specification refers to an aromatic or non-aromatic cyclic group having 5 to 20 atoms, preferably 5 to 14 atoms forming the cyclic ring(s) and including at least one hetero atom such as nitrogen, sulfur or oxygen among the atoms forming the cyclic ring, which is a "5 to 20-membered, preferably 5- to 14-membered aromatic heterocyclic group" (also, "heteroaryl" or "heteroaromatic") in the former case and a "5 to 20-membered", preferably a "5- to 14-membered non-aromatic heterocyclic group" in the latter case.

Among the heterocyclic groups which may be mentioned include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole.

As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 20-membered heterocyclic groups, preferably 3 to 14-membered heterocyclic groups and all subsets of heterocyclic groups (including non-heteroaromatic or heteroaromatic) subsumed under the definition of heterocyclic group are 3 to 20-membered heterocyclic groups, preferably 3 to 14-membered heterocyclic groups.

The term "8 to 20-membered heterocyclic group", or "8 to 14-membered heterocyclic group" refers to an aromatic or non-aromatic fused bicyclic or tricyclic group having 8 to 20, preferably 8 to 14 atoms forming the cyclic rings (two or three rings) and include at least one hetero atom such as nitrogen, sulfur or oxygen among the atoms forming the cyclic rings, which is a "8 to 20-membered", preferably a "8- to 14-membered aromatic heterocyclic group" (also, "heteroaryl" or "heteroaromatic") in the former case and a "8 to 20-membered", preferably a "8- to 14-membered non-aromatic heterocyclic group" in the latter case. "8 to 20-membered heterocyclic groups" and "8 to 14 membered heterocyclic groups" are represented by fused bicyclic, tricyclic and tetracyclic ring structures containing nitrogen atoms such as indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "5- to 14-membered non-aromatic heterocyclic group" as used throughout the present specification refers to non-aromatic cyclic group having 5 to 14 atoms forming the cyclic ring and including at least one hetero atom such as nitrogen, sulfur or oxygen among the atoms forming the cyclic ring. As specific examples there may be mentioned non-aromatic heterocycles such as pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimideandsuccinimide. As examples of the "5- to 14-membered non-aromatic heterocyclic group" there may be mentioned preferably, pyrrolidinyl, piperidinyl and morpholinyl, and more preferably pyrrolidinyl, piperidinyl, morpholinyl and pyrrole.

The term "8- to 14-membered non-aromatic heterocyclic group" as used throughout the present specification refers to a non-aromatic fused cyclic ring system (generally with two or three rings) having 8 to 14 atoms forming the cyclic rings (bicyclic or tricyclic) and including at least one hetero atom such as nitrogen, sulfur or oxygen among the atoms forming the cyclic rings.

The term "5- to 14-membered heterocyclic group" as used throughout the present specification refers to an aromatic or non-aromatic cyclic group having 5 to 14 atoms forming the cyclic ring and including at least one hetero atom such as nitrogen, sulfur or oxygen among the atoms forming the cyclic ring, which is a "5- to 14-membered aromatic heterocyclic group" in the former case and a "5- to 4-membered non-aromatic heterocyclic group" in the latter case. Specific examples of the "5- to 14-membered heterocyclic group" therefore include specific examples of the "5- to 14-membered aromatic heterocyclic group" and specific examples of the "5- to 14-membered non-aromatic heterocyclic group".

As the "5- to 14-membered heterocyclic group" there may be mentioned preferably pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline and carbostyryl, among others.

The term "6- to 14-membered aromatic heterocyclic group" as used throughout the present specification refers to those substituents defined by "5- to 14-membered aromatic heterocyclic group" which have 6 to 14 atoms forming the cyclic ring. As specific examples there may be mentioned pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole and phenothiazine*. "8 to 14-membered aromatic heterocyclic groups" refer to those substituents or radicals having 8 to 14 atoms forming fused two or three cyclic ring systems. Specific examples include indole, quinoline, isoquinoline, quinolizine, phthalazine, naphthyridine, quinazoline, cinnoline, acridine, benzothiophene, benzofuran, benzothiazole, pyrrolopyrimidine, pyrrolopyrazine, furopyrimidine and phenothiazine, among numerous others.

The term "6- to 14-membered heterocyclic group" as used throughout the present specification refers to those substituents defined by "5- to 14-membered heterocyclic group" which have 6 to 14 atoms forming the cyclic ring(s). As specific examples there may be mentioned piperidinyl, piperazinyl, N-methylpiperazinyl, morpholinyl, tetrahydropyranyl, 1,4-dioxane and phthalimide.

The term "3 to 7-membered heterocyclic group" as used throughout the present specification refers to those heterocyclic substituents which have 3 to 7 atoms forming the cyclic ring, preferably 5 to 6 atoms forming the cyclic ring.

The term "8 to 14-membered heterocyclic group" as used throughout the present specification refers to those substituents defined "8- to 14-membered heterocyclic groups which have 8 to 14 atoms forming the fused cyclic ring system.

The term "heterocyclylalkyl", as used herein, refers to an alkyl group substituted with a heterocycle group.

The term "hydrocarbyl", as used herein, refers to an optionally substituted group that is bonded through a carbon atom and typically has at least one carbon-hydrogen bond and a primarily carbon backbone, but may optionally include heteroatoms. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer atoms in the substituent, preferably eight or fewer, more preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and % or heterocyclyls) in which two or more atoms are common to two adjoining rings, e.g., the rings are "fused rings". Rings that are joined through non-adjacent atoms are termed "bridged" rings. Each of the rings of the polycycle can be substituted with, without limitation, such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" or "blocking group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W., Wuts, P. G. M. Protective Groups in Organic Synthesis, $2^{nd}$ ed.; Wiley: New York, 1991). Typical blocking groups are used on alcohol groups, amine groups, carbonyl groups, carboxylic acid groups, phosphate groups and alkyne groups among others.

Exemplary alcohol-hydroxyl protecting groups include acetyl (removed by acid or base), benzoyl (removed by acid or base), benzyl (removed by hydrogenolysis, 5-methoxyethoxymethyl ether (MEM, removed by acid), dimethoxytrityl [bis-(4-methoxyphenyl)phenylmethyl] (DMT, removed by weak acid), methoxymethyl ether (MOM, removed by acid), methoxytrityl [(4-methoxyphenyl)diphenylmethyl], (MMT, Removed by acid and hydrogenolysis), p-methoxylbenzyl ether (PMB, removed by acid, hydrogenolysis, or oxidation), methylthiomethyl ether (removed by acid), pivaloyl (Piv, removed by acid, base or reductant agents. More stable than other acyl protecting groups, tetrahydropyranyl (THP, removed by acid), tetrahydrofuran (THF, removed by acid), trityl (triphenyl methyl, (Tr, removed by acid), silyl ether (e.g. trimethylsilyl or TMS, tert-butyldimethylsilyl or TBDMS, tri-iso-propylsilyloxymethyl or TOM, and triisopropylsilyl or TIPS, all removed by acid or fluoride ion such as such as NaF, TBAF (tetra-n-butylammonium fluoride, HF-Py, or HF-$NEt_3$); methyl ethers (removed by TMSI in DCM, McCN or chloroform or by $BBr_3$ in DCM) or ethoxyethlyl ethers (removed by strong acid).

Exemplary amine-protecting groups include carbobenzyloxy (Cbz group, removed by hydrogenolysis), p-Methoxylbenzyl carbon (Moz or MeOZ group, removed by hydrogenolysis), tert-butyloxycarbonyl (BOC group, removed by concentrated strong acid or by heating at elevated temperatures), 9-Fluorenylmethyloxycarbonyl (FMOC group, removed by weak base, such as piperidine or pyridine), acyl group (acetyl, benzoyl, pivaloyl, by treatment with base), benzyl (Bn groups, removed by hydrogenolysis), carbamate, removed by acid and mild heating, p-methoxybenzyl (PMB, removed by hydrogenolysis), 3,4-dimethoxybenzyl (DMPM, removed by hydrogenolysis), p-methoxyphenyl (PMP group, removed by ammonium cerium IV nitrate or CAN); tosyl (Ts group removed by concentrated acid and reducing agents, other sulfonamides, Mesyl, Nosyl & Nps groups, removed by samarium iodide, tributyl tin hydride.

Exemplary carbonyl protecting groups include acyclical and cyclical acetals and ketals (removed by acid), acylals (removed by Lewis acids) and dithianes (removed by metal salts or oxidizing agents).

Exemplary carboxylic acid protecting groups include methyl esters (removed by acid or base), benzyl esters (removed by hydrogenolysis), tert-butyl esters (removed by acid, base and reductants), esters of 2,6-disubstituted phenols (e.g. 2,6-dimethylphenol, 2,6-diisopropylphenol, 2,6-di-tert-butylphenol, removed at room temperature by DBU-catalyzed methanolysis under high-pressure conditions, silyl esters (removed by acid, base and organometallic reagents), orthoesters (removed by mild aqueous acid), oxazoline (removed by strong hot acid (pH<1, T>100° C.) or strong hot alkali (pH>12, T>100° C.)).

Exemplary phosphate group protecting groups including cyanoethyl (removed by weak base) and methyl (removed by strong nucleophiles, e.g. thiophenol/TEA).

Exemplary terminal alkyne protecting groups include propargyl alcohols and silyl groups.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic, non-aromatic and inorganic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents (groups) as otherwise described herein, for example, a halogen, a hydroxyl, a carbonyl (such as a carboxyl, an alkoxycarbonyl, a formyl, or an acyl), an ether, a thioether, a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on a moiety or chemical group can themselves be substituted.

It will be understood that "substitution" or "substituted with" includes the implicit proviso that such substitution is in accordance with permitted valence of the substituted atom and the substituent, and that the substitution results in a stable compound. e.g., which does not spontaneously undergo transformation such as by rearrangement, cyclization, elimination, etc. It is acknowledged that the term "unsubstituted" simply refers to a hydrogen substituent or no substituent within the context of the use of the term.

Preferred substituents for use in the present invention include, for example, within context, hydroxyl, carboxyl, cyano (CEN), nitro ($NO_2$), halogen (preferably, 1, 2 or 3 halogens, especially on an alkyl, especially a methyl group such as a trifluoromethyl), thiol, alkyl group (preferably. $C_1$-$C_6$, more preferably, $C_1$-$C_3$), alkoxy group (preferably, $C_1$-$C_6$ alkyl or aryl, including phenyl), ether (preferably, $C_1$-$C_6$ alkyl or aryl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl) (preferably, $C_1$-$C_6$ alkyl or aryl), thioester (preferably, $C_1$-$C_6$ alkyl or aryl), halogen (F, Cl, Br, I), nitro or amine (including a five- or six-membered cyclic alkylene amine, including a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). More preferably, the term "substituted" shall mean within its context of use alkyl, alkoxy, halogen, hydroxyl, carboxylic acid, nitro and amine (including mono- or di-alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms.

As used herein, the definition of each expression of alkyl, m, n, etc. when it occurs more than once in any structure, is intended to reflect the independence of the definition of the same expression in the structure.

By way of example, certain preferred aromatic and aliphatic rings and their derivatives and substituents which may be used as pharmacophores or substituents in compounds according to the present invention include, but are not limited to, phenyl, benzyl, pyridine, cyclohexadiene, dihydropyridine, tetrahydropyridine, piperidine, pyrazine, tetrahydro-pyrazine, dihydro-pyrazine, piperazine, pyrimidine, dihydro-pyrimidine tetrahydro-pyrimidine, hexahydro-pyrimidine, pyrimidinone, triazine, dihydro-triazine, tetrahydro-triazine, triazinane, tetrazine, dihydro-tetrazine, tetrahydro-tetrazine, tetrazinane, pyrrol, dihydro-pyrrole, pyrrolidine, imidazolidine, dihydro-imidazolidine, imidazole, dihydro-imidazole, azetidine, triazole, dihydro-triazole, triazolidine, tetrazole, dihydro-tetrazole, tetrazolidine, diazepane, tetrahydro-diazepine, dihydro-diazepine, diazepine, oxazole, dihydrooxazole, oxazolidine, isoxazole, dihydroisoxazole, isoxazolidine, thiazole, dihydrothiazole, thiazolidine, isothiazole, dihydroisothiazole, isothiazolidine, oxadiazole, dihydro-oxadiazole, oxadiazolidine, thiadiazole, dihydro-thidiazole, thidiazolidine, oxazinane, dihydro-oxazinane, dihydro-oxazine, oxazine (including morpholine), thiazinane, dihydro-thiazinane, dihydro-thiazine, thiazine (including thiomorpholine), thiazine, furan, dihydrofuran, tetrahydrofuran, thiophene, pyridazine-3,6-dione, tetrahydrothiophene, dihydrothiophene, tetrahydrothiophene, dithiolane, dithiole, dithiolone, dioxolane, dioxole, oxathiole, oxathiolane, pyridinone, dioxane, dioxanedione, benzoquinone, dihydro-dioxine, dioxine, pyran, 3,4-dihydro-2H-pyran, pyranone, 2H-pyran-2,3(4H)-dione, oxathiane, dihydro-oxathiine, oxathiine, oxetane, thietane, thiazeto, cyclohexadienone, lactam, lactone, piperazinone, pyrroledione, cyclopentenone, oxazete, oxazinanone, dioxolane, 3,4-dihydro-2H-thiopyran 1,1-dioxide, dioxolanone, oxazolidinone, oxazolone, thiane 1-oxide, thiazinane 1-oxide, tetrahydro-thiopyran, thiane 1,1-dioxide, dioxazinane, pyrazolone, 1,3-thiazete, thiazinane 1,1-dioxide, 6,7-dihydro-5H-1,4-dioxepine, 1,2-dihydropyridazin-3(4H)-one, pyridine-2,6(1H,3H)-dione, and sugar (glucose, mannose, galactose, fucose, fructose, ribose).

Bicyclic and fused rings include, for example, naphthyl, quinone, quinolinone, dihydroquinoline, tetrahydroquinoline, naphthyridine, quinazoline, dihydroquinazoline, tetrahydroquinazoline, quinoxaline, dihydroquinazoline, tetrahydroquinazoline, pyrazine, quinazoline-2,4(1H,3H)-dione, isoindoline-1,3-dione, octahydro-pyrrolo-pyridine, indoline, isoindoline, hexahydro-indolone, tetrahydropyrrolo oxazolone, hexahydro-2H-pyrrolo[3,4-d]isoxazole, tetrahydro-1,6-naphthyridine, 2,3,4,5,6,7-hexahydro-1H-pyrrolo[3,4-c]pyridine, 1H-benzo[d]imidazole, octahydropyrrolo[3,4-c]pyrrole, 3-azabicyclo[3.1.0]hexane, 7-azabicyclo[2.2.1]hept-2-ene, diazabicyclo-heptane, benzoxazole, indole, 1,4-diazabicyclo[3.3.1]nonane, azabicyclo-octane, naphthalene-1,4-dione, indene, dihydroindene, 2,3,3a,7a-tetrahydro-1H-isoindole, 2,3,3a,4,7,7a-hexahydro-1H-isoindole, 1,3-dihydroisobenzofuran, 1-methyl-3a,4,5,6,7,7a-hexahydro-1H-indole, 3-azabicyclo[4.2.0]octane, 5,6-dihydrobenzo[b]thiophene, 5,6-dihydro-4H-thieno[2,3-b]thiopyran, 3,4-dihydropyrazin-2(1H)-one, 2H-benzo[b][1,4]thiazine, naphthyridin-4(1H)-one, octahydropyrrolo[1,2-a]pyrazine, imidazo-pyridazine, tetrahydroimidazo-pyridazine, tetrahydropyridazine, thiazinone, 5-thia-1-azabicyclo[4.2.0]oct-2-en-8-one, 4-thia-1-azabicyclo[3.2.0]heptan-7-one, 1,6,7,8-tetrahydroimidazo[4,5-d][1,3]diazepine, 8H-thiazolo[4,3-c][1,4]oxazin-4-ium, 8H-thiazolo[4,3-c][1,4]thiazin-4-ium, pteridine, thiazolo[3,4-a]pyrazin-4-ium, 7-(methylimino)-7H-pyrrolo[1,2-c]thiazol-4-ium, thiazolo-pyrazine, 3,7-dioxabicyclo[4.1.0]hept-4-ene, 6,7-dihydro-5H-pyrrolo[1,2-a]imidazole, 3,3a-dihydrofuro[3,2-b]furan-2(6aH)-one, tetrahydro-3aH-[1,3]dioxolo[4,5-c]pyrrole, 7-ethylidene-7H-pyrrolo[1,2-c]thiazol-4-ium, hexahydro-1H-pyrrolo[2,1-c][1,4]oxazine, 6,7,8,8a-tetrahydro-1H-pyrrolo[2,1-c][1,4]oxazine, 2-azabicyclo[2.2.2]oct-2-ene, 6,6a-dihydrothieno[3,2-b]furan-5(3aH)-one, 4,5-dihydropyridin-3(2H)-one, 4,7a-dihydro-3aH-[1,3]dioxolo[4,5-c]pyran, 6,7-dihydro-1H-furo[3,4-c]pyran-1,3(4H)-dione, 3.3a,4,7a-tetrahydro-2H-furo[2,3-b]pyran, 2,4a,7,7a-tetrahydro-1H-cyclopenta[c]pyridine, 4H-pyrano[3,2-b]pyridine-4,8(5H)-dione, 1,2,3,3a,4,7a-hexahydropyrano[4,3-b]pyrrole, 2,3,8,8a-tetrahydroindolizin-7(1H)-one, octahydro-1H-pyrido[1,2-a]pyrazin-1-one, 2,6,7,8,9,9a-hexahydro-1H-pyrido[1,2-a]pyrazin-1-one, 6,7,8,8a-tetrahydropyrrolo[1,2-a]pyrazin-1(2H)-one, hexahydropyyrrolo[1,2-a]pyrazin-1(2H)-one, bicyclo[2.2.1]hepta-2,5-diene.

Spiro moieties: 1,5-dioxaspiro[5.5]undecane, 1,4-dioxaspiro[4.5]decane, 1,4-diazabicyclo[3.2.1]octane, 5-azaspiro[2.5]octane, 5-azaspiro[2.4]heptane, 3,9-diaza-6-azoniaspiro[5.5]undecane, 3,4-dihydrospiro[benzo[b][1,4]oxazine-2,1'-cyclohexane], 7-oxa-4-azaspiro[2.5]oct-5-ene.

Pharmaceutical compositions comprising combinations of an effective amount of at least one glucosepane or glucosepane derivative compound or an imidazole compound according to the present invention otherwise described herein, all in effective amounts, in combination with a pharmaceutically effective amount of a carrier, additive or excipient, represents a further aspect of the present invention. Optionally, at least one additional bioactive agent may be included in pharmaceutical compositions according to the present invention.

The compositions used in methods of treatment of the present invention, and pharmaceutical compositions of the invention, may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in methods of treatment of the present invention, and pharmaceutical compositions of the invention, may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions used in methods of treatment of the present invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more (up to several grams), more preferably about 1 milligram to about 600 milligrams, and even more preferably about 10 milligrams to about 500 milligrams of active ingredient, alone or in combination with at least one additional non-antibody attracting compound which may be used to treat diabetes or a diabetes related disorder or to impact the effects of aging as otherwise set forth herein.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from or at risk of developing diabetes and/or a diabetes related disorder or who wishes to effect aging processes can be treated by administering to the patient (subject) an effective amount of glucosepane and related aspects and embodiments according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating diabetes or a diabetes related disorder to ameliorate the secondary effects and conditions associated with diabetes. This treatment can also be administered in conjunction with other conventional therapies.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient as described herein is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent, as are topically administered compositions.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, phosphodiesterase inhibitors, cholesterol/lipid lowering agents and lipid profile therapies, traditional anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), antiinflammatory agents, anticancer agents and anti-infective agents such as antibiotics, antifungals or antiviral compounds, among others.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Processes and Compounds of the Invention-Establishing a Route to an Efficient Chemical Synthesis of Glucosepane In analyzing the glucosepane core, the inventors were first intrigued by its reported tendency to adopt an iso-imidazole topology, rather than that of the corresponding aromatic imidazole. The inventors therefore set out to investigate this tautomeric preference through Gaussian calculations performed on model compounds (Table 1).

TABLE 1

Results from density functional theory (DFT) calculations comparing energies of various imidazole tautomerization states.

imidazole ⇌ iso-imidazole   ΔG (kcal/mol)

| Entry | X | Y | ΔG (kcal/mol)$^a$ |
|---|---|---|---|
| 1 | H | H | 26.7 |
| 2 | H | NHMe | 10.5 |
| 3 | NMe$_2$ | H | −1.5 |
| 4 | NMe$_2$ | NHMe | −14.8 |

$^a$All calculations were performed using the Gaussian 09 program suite using the CBS-QB3 method. All calculations implemented a continuum model to account for the effects of water solvent.

While unsubstituted imidazole (Entry 1) greatly prefers the aromatic arrangement (ΔG=26.7 kcal/mol), addition of methylamino substituents to the 2 and 4-position decreases this preference substantially (Entries 2-3; ΔG=10.5 and −1.5 kcal/mol, respectively). Interestingly, 2,4-diamino-substituted derivative (entry 4), which contains the same substitution pattern as glucosepane, exhibits a strong preference for the non-aromatic tautomer (ΔG=−14.8 kcal/mol). This trend may be partly explained by the decreasing aromatic stabilization of imidazole upon addition of electron-donating substituents to the 2- and 4-positions, as indicated in prior work and additional calculations provided herein in the Supporting Information.[19],[20] Furthermore, the inability of electron-donating substituents at the 2- and 4-positions to delocalize into the imidazole ring may drive a decrease in stabilization energy, as well as a tendency to tautomerize into the iso-imidazole, which permits such delocalization. This model is further supported by geometry minimization experiments, which demonstrate for the 2,4-diamino imidazole system that the 4-substituent is rotated such that N-lone pairs are partially non-overlapping with the heterocycle's pi-system. Taken together, the inventors hypothesized that in the setting of 4- and 2,4-diamino imidazoles, the decrease in aromaticity does not afford a sufficiently high degree of energetic stabilization; in the iso-imidazole tautomer, on the other hand, electron-donating amines have the opportunity to participate extensively in resonance stabilization.

Figure 2:
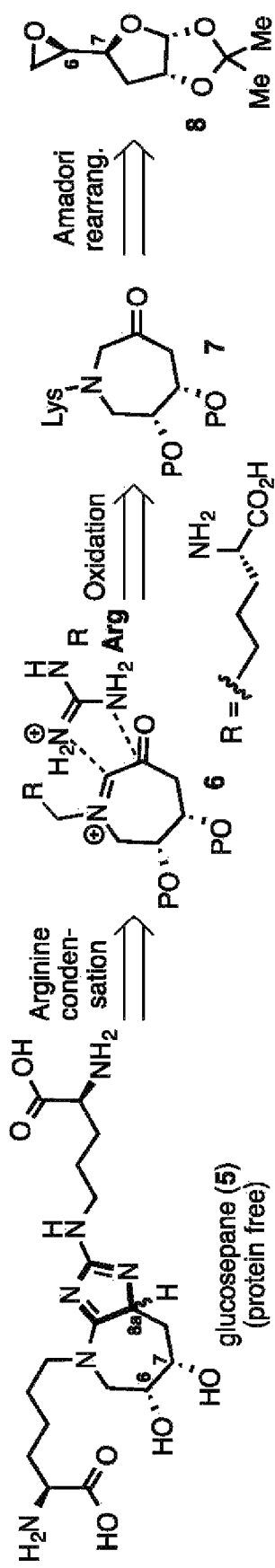
FIG. 2 shows a Retrosynthetic analysis of glucosepane to facilitate synthesis.

With this information in mind, the inventors constructed a retrosynthesis (FIG. 2). They reasoned that given the strong thermodynamics driving the core heterocycle's tautomerization state, formation of the C—N bonds between the arginine guanidine and the lysine-derived azepane (6+Arg→5) would be accompanied by spontaneous isomerization to the correct structure. They therefore first chose to disconnect at the two C—N bonds endocyclic to the imidazole motif. This disconnection is identical to that suggested by Lederer and colleagues for the final step in the biosynthesis of glucosepane,[17] wherein arginine is proposed to condense directly with an alpha-keto iminium intermediate (6), formed from an adduct derived from lysine and glucose. They then reasoned that 6 could be generated through N-oxidation and regioselective elimination of azepane 7. In turn, azepane 7 could be deconstructed via an Amadori rearrangement sequence to a suitably protected lysine derivative and known epoxide 8.[21] In this sense, 8 would serve as the source of the chiral diol encountered in glucosepane diastereomer 5. As it is unknown which stereoisomer(s) of glucosepane are most prevalent in vivo, 8 was chosen as it reflects the stereochemistry of glucose, which is the most common precursor in vivo. In future studies, simply inverting the C-6 and C-7 stereocenters of the starting epoxide 8 would then permit access to other reported diastereomers.

Figure 3:
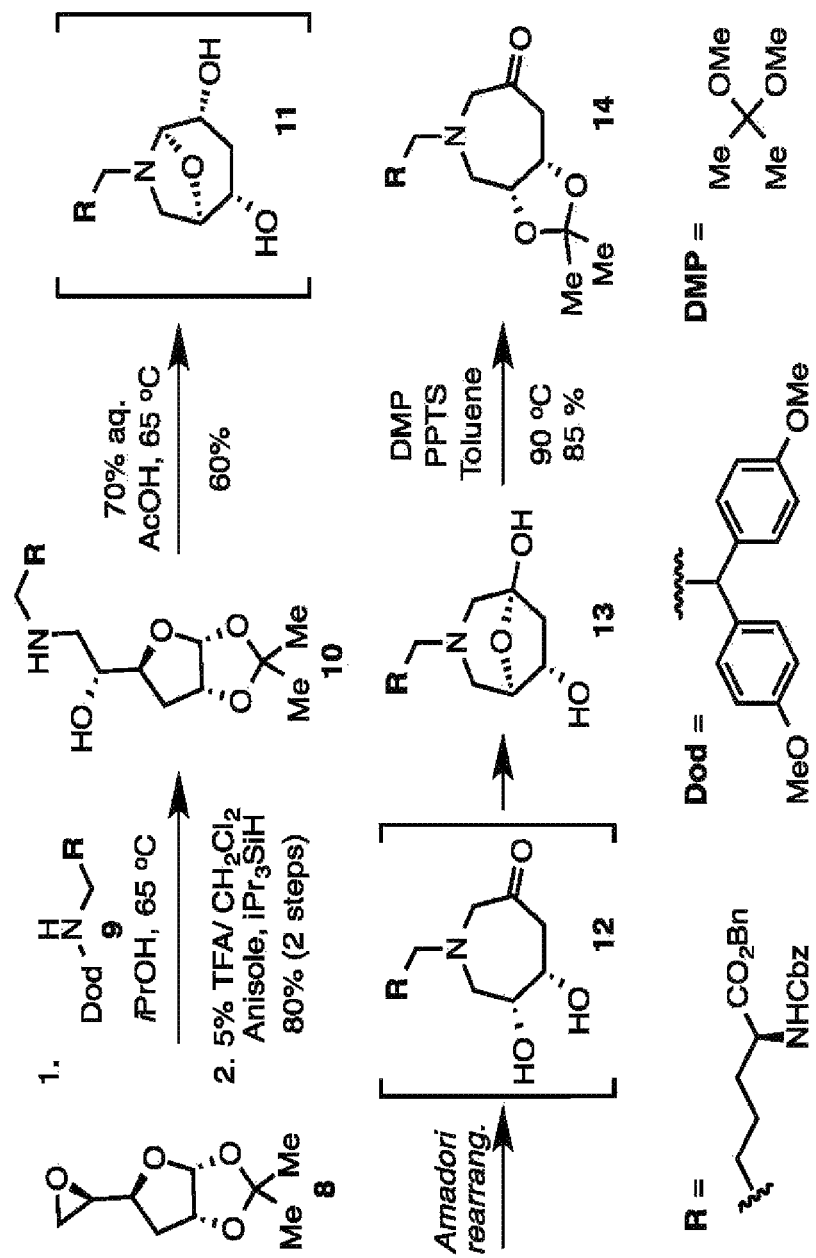
FIG. 3 shows scheme 1 which shows the exemplary chemical synthetic steps which provide the protected ketone intermediate 14 from the protected epoxide 8.

In the present invention (scheme 1, FIG. 3), the synthesis began with epoxide 8, prepared from diacetone-D-glucose as previously described.[22] A scheme showing the synthesis of epoxide 8 is presented at the beginning of the experimental section. Nucleophilic addition of Dod-protected lysine derivative 9 to the less substituted side of the epoxide in 8, followed by acidic deprotection of the resulting tertiary amine, provides amino alcohol 10 in 80% yield over two steps. Acetonide removal in the presence of aqueous acetic acid then affords azepane acetal 13. The conversion of 10 to 13 proceeds by way of intramolecular attack of the lysine amino group onto the anomeric carbon of the carbohydrate with accompanying acetonide loss to give intermediate azepane hemiaminal 11.[23] This material spontaneously undergoes Amadori rearrangement[24, 25] to give an intermediate ketone 12, which is then trapped intramolecularly by the C-6 hydroxyl to yield bridged bicyclic acetal 13 in 60% yield. Reinstallation of the acetonide group proceeds with reformation of the ketone functionality to afford the desired protected ketone (14).

Access to 14 set the stage for oxidation-trapping attempts, outlined in the retrosynthesis. Although the inventors were able to achieve the desired α-keto iminium intermediate (16) by way of oxidation with Selectfluor®, this material rapidly undergoes ring contraction to give aldehyde 17 (Scheme 2A). All attempts to condense 17 with guanidine derivatives, including various protected forms of arginine, were met only by complete decomposition of 17, and recovery of the guanidine nucleophile. Furthermore, attempts to perform oxidation and guanidine trapping in "one pot" were also unsuccessful, providing similar results to the two-step process.

In light of these observations, the inventors decided to re-engineer the retrosynthesis. While the inventors were encouraged by their ability to access α-keto iminium 16, the refractoriness of this species to intermolecular trapping suggested that perhaps condensation with the arginine guanidine functionality succeeds in vivo because of proximity effects. In other words, crosslinking is only likely to occur for proteins wherein an appropriately modified lysine residue is directly adjacent to the attacking arginine, rendering the process functionally intramolecular (even for proteins such as collagen wherein intermolecular crosslinking is accelerated due to the high local concentration of reactive side-chains).[3, 26] In this light, it occurred to the inventors that for the reaction to be successful, they must tether the nucleophilic (guanidine) and electrophilic (iminium) components together at the time of oxidation.

Figure 4:
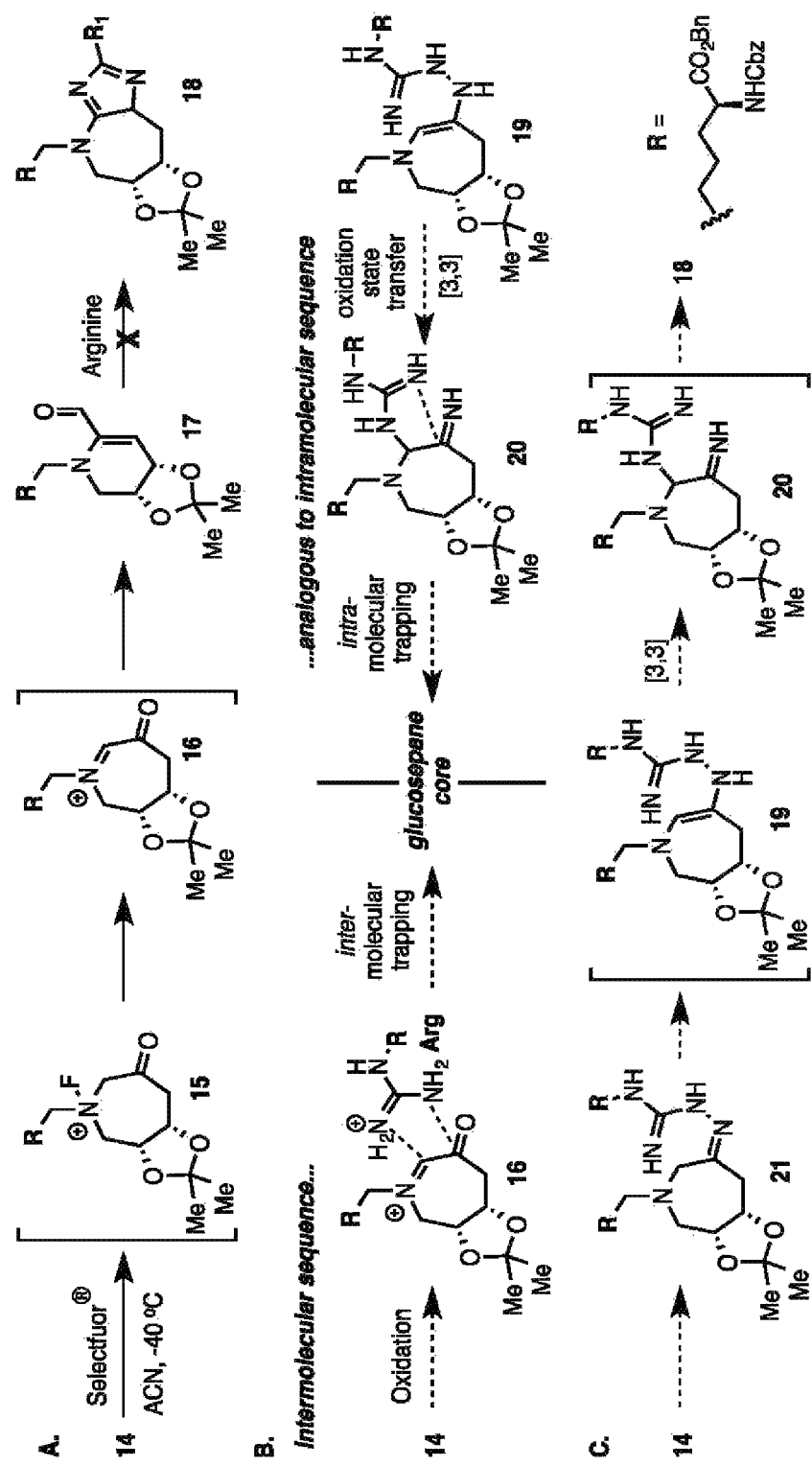
FIG. 4, scheme 2A, B and C show further analysis and chemical steps from ketone intermediate 14 to refine the chemical synthetic procedure of the present invention.

In this light, they recognized that an intramolecular oxidation transfer process—by way of a [3,3]-sigmatropic rearrangement from semicarbazone tautomer 19—would afford an intermediate (20) with the same core oxidation state to α-keto iminium 16 (FIG. 4, Scheme 2B). Furthermore, 20 also contains a tethered guanidine function perfectly poised for subsequent intramolecular cyclization and tautomerization to afford the glucosepane core. Furthermore, we reasoned that simple condensation of lysine-derived ketone 14 with semicarbazide derivatives (Scheme 2C) would permit rapid access to semicarbazone 19, capable of tautomerizing to the desired [3.3] rearrangement substrate (20). In this sense, 20 would function as a masked version of α-keto iminium 16, possessing the correct oxidation state and functional group disposition to afford the desired iso-imidazole 18. Although such an imidazole-formation sequence has never before been reported to the knowledge of the inventors, they were encouraged by previous reports of analogous hetero-Claisen rearrangements.[27-30] Taken together, the inventors envisioned that this sequence would accomplish the goal of directly coupling oxidation and condensation steps, solving the problems associated with our intermolecular trapping sequence.

Figure 5:
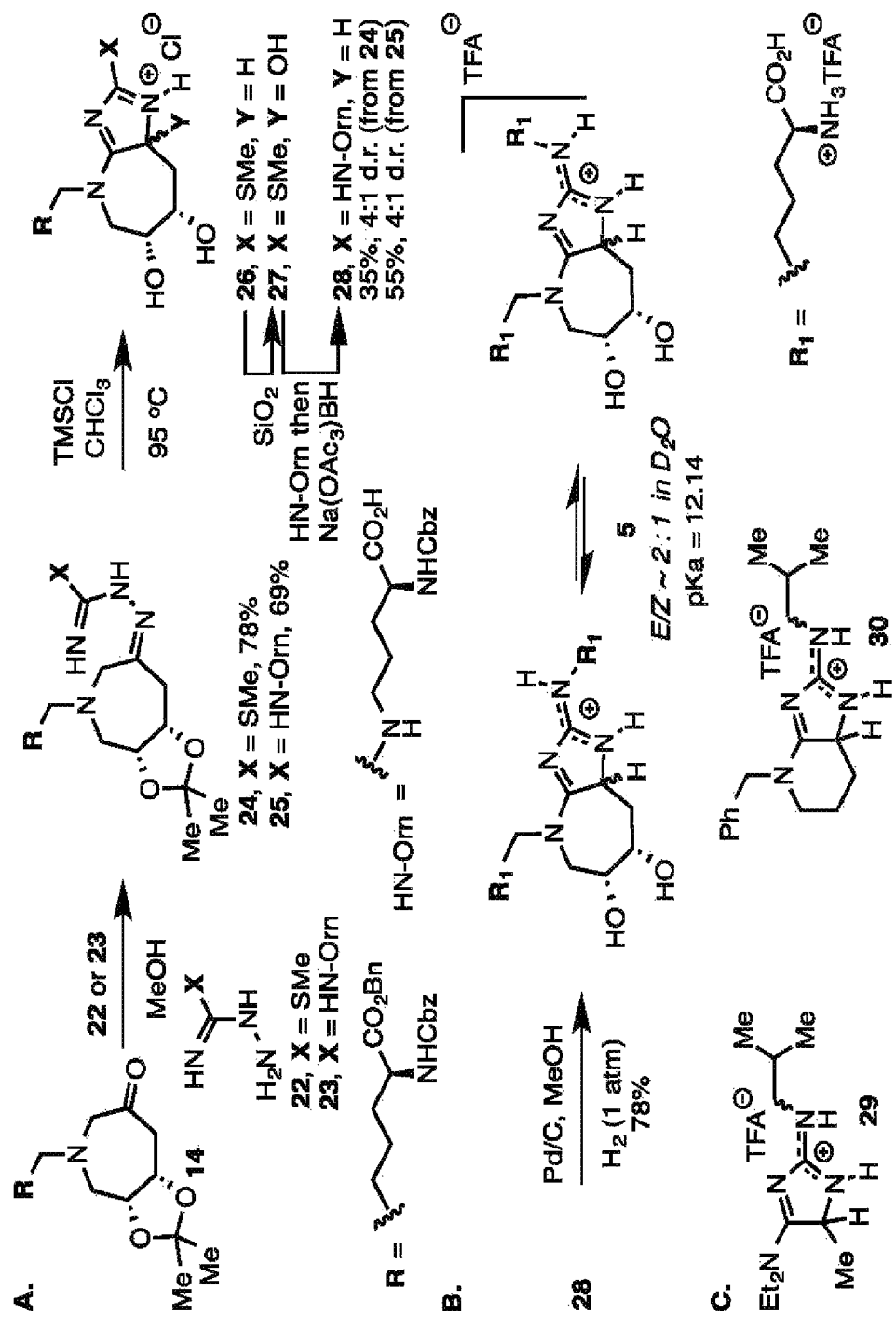
FIG. 5, scheme 3, shows the chemical steps to provide the fully protected glucosepane derivative 28 which can be deprotected as presented to provide glucosepane derivative 5 as the formate or TFA salt.
Figure 6:
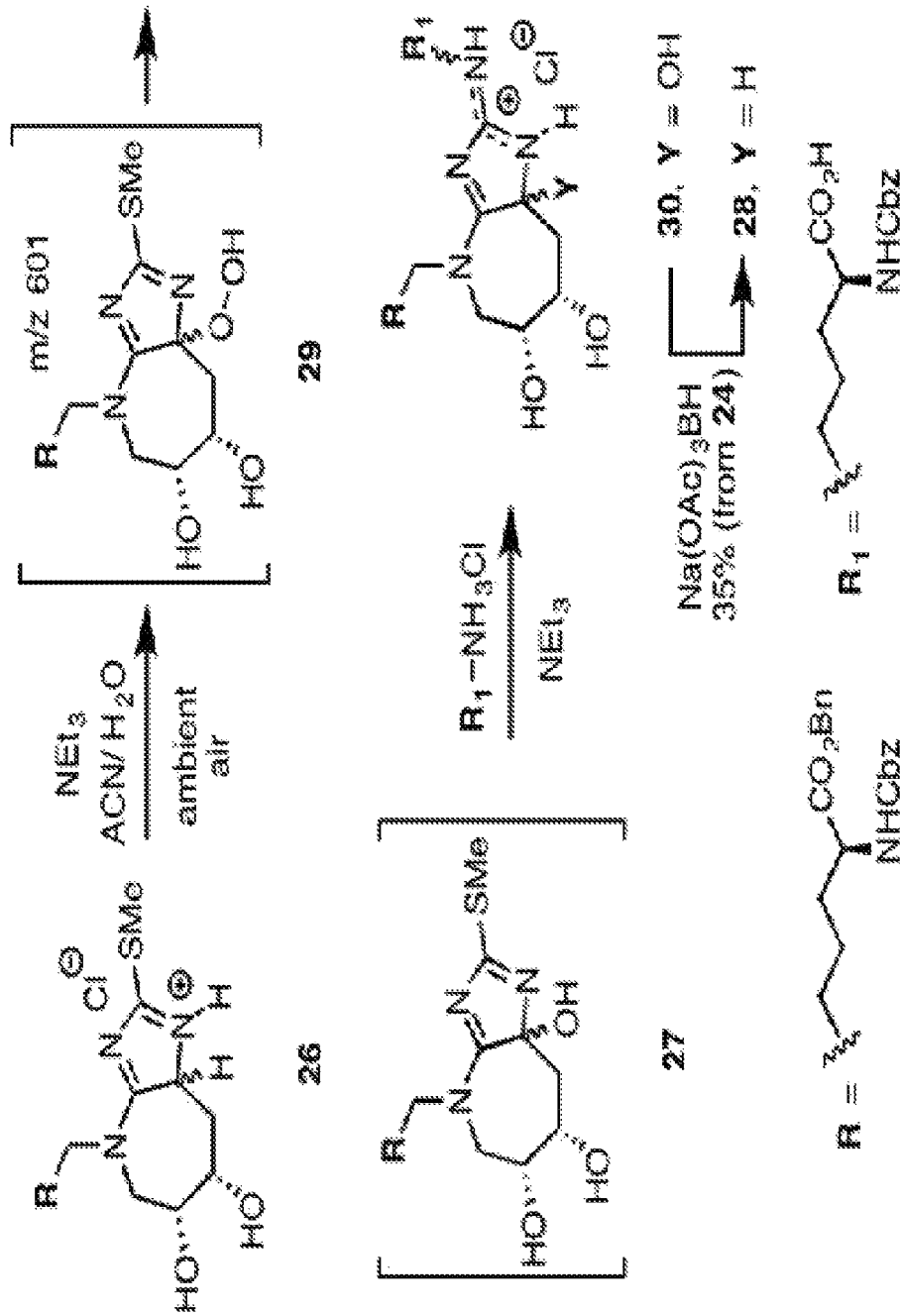
FIG. 6, scheme 3B, shows the synthesis of two additional 2,4-diaminoimidazoles (29 and 30) from intermediates 26 and 27.

In the event (FIG. 5. Scheme 3A.), condensation of thiomethyl semicarbazide 22 with ketone 14 proceeded smoothly to afford semicarbazone 24 (as a mixture of E/Z isomers) in 78% yield. After several failed attempts, the inventors were encouraged to discover that upon treating semicarbazone 24 with excess chlorotrimethylsilane (TMSCl) in dry, refluxing chloroform induced the formation of iso-thioimidazole 26. The inventors believe that this material forms by way of the pathway predicted in Scheme 2B, by way of tantomerization, [3,3]-sigmatropic rearrangement and cyclodeamination, and is accompanied by acetonide removal, likely resulting from HCl generated by aqueous quenching of excess TMSCl. Notably, 26 is isolated as an epimeric mixture at C-8a, as confirmed by NMR analysis.[31] Interestingly, attempts to purify iso-thioimidazole 26 under open atmosphere led to only to the isolation of C-8a-oxidized product 27.[32] By displacing the thiomethyl group with an ornithine derivative followed by C-8a reduction using $Na(OAc)_3BH$, the inventors were able to access protected glucosepane 28 (see Supporting Information for details).

Despite this result, the inventors sought a more concise route to intermediate 28. Replacement of 22 in this sequence with a fully elaborated amino-arginine derivative (23) readily afforded 25 in good yield (69%), and gratifyingly, this intermediate also underwent the desired rearrangement, cyclization and acetonide removal sequence. This sequence therefore furnished fully protected glucosepane derivative 28 in 4:1 diasteromeric ratio in only a single synthetic step.

With backbone-protected glucosepane in hand, completion of the synthetic sequence proved straightforward (FIG. 5, Scheme 3B.). Global hydrogenolytic deprotection of Cbz and benzyl ester protecting groups was achieved using Pd/C under an atmosphere of hydrogen gas and either TFA or formic acid (FIG. 5, Scheme 3B.), enabling rapid access to 5 as either the formate or TFA salt. Although two C-8a epimers are produced in a 4:1 ratio through this route, these can be separated by preparative HPLC. Spectral data obtained from $^1$H- and $^{13}$C-NMR experiments using synthetic 5 proved identical to that reported by Lederer and colleagues for material isolated from model reactions.[16] This confirms that the synthetic glucosepane exists as the iso-imidazole tautomer. Overall, this synthetic route proceeds in a total of 8 steps and 12% overall yield and is the first to provide access to two of the eight possible glucosepane diastereomers in enantiomerically pure form.

To provide further experimental evidence for 2,4-diaminoimidazoles to adopt the iso-imidazole tautomer, the inventors utilized our newly developed rearrangement reaction to synthesize two additional 2,4-diaminoimidazoles (29 and 30, FIG. 5, Scheme 3C.).[33] These were prepared in two steps from commercially available starting materials, and as expected, were found to adopt the iso-imidazole tautomer exclusively. These results support our computational data, and confirm that imidazoles with electron-rich substituents at the 2- and 4-positions prefer the iso-imidazole tautomer.

With synthetic glucosepane (5) in hand, we next investigated its structural features using multidimensional NMR techniques. Interestingly, 2D $^1$H-NMR NOESY experiments of compound 5 revealed the presence of "conformational exchange" peaks,[34] which we attribute to E/Z isomerization about the exocyclic C2-N bond in glucosepane. Indeed, although the original glucosepane isolation report did note the possibility of E/Z isomerism in acyclic 2-amino imidazoles, the presence of these exchange peaks in the case of glucosepane have previously been incorrectly attributed to stereoisomerism at the C-8a stereocenter.[35] Using an EXSY (EXchange SpectroscopY) NOESY sequence,[34] the inventors were able to calculate an approximate rate for this conformational exchange process on the order of 3 $s^{-1}$ in $D_2O$.[28]

The inventors next took advantage of glucospane's intrinsic spectral properties to measure the $pK_a$ of the iso-imidazole core. These experiments revealed compound 5 to possess only one basic site under aqueous conditions with a $pK_a$ of approximately 12, which the inventors believe to reflect protonation at the iso-imidazole NI atom, consistent with both NMR data and DFT calculations.[16] Exposure of either epimer of 5 to $D_2O$ leads to quantitative hydrogen/deuterium exchange at the C-8a H-atom, which occurs rapidly (<60 min) under basic conditions (aqueous NaOD). Taken together, these studies suggest that glucosepane contains both acidic and basic sites, the latter of which possesses a $pK_a$ quite close to that of native arginine ($pK_a$=12.5). The relevance of these structural features to glucosepanes biological properties is currently being investigated in our laboratories.

Herein the inventors report the first total synthesis of glucosepane, which is rapid, high-yielding, and stereoselective. This contribution was enabled by our development of a simple, one-pot protocol for synthesizing several heavily substituted imidazoles via a sigmatropic rearrangement-cyclization sequence. This novel chemical process provides an entry point into other complex iso-imidazole-containing PTMs (e.g., pentosinane), as well as various polyguanidine-containing natural products. Furthermore, given that imidazoles are quite difficult to prepare in general, our one-pot synthetic route may prove useful as a general strategy for imidazole synthesis. The have performed detailed computational studies to explore the surprising tendency of substituted imidazoles to adopt non-aromatic tautomerization states. These studies suggest that imidazoles possessing electron-donating groups at the 2- and 4-positions possess a strong energetic preference for the iso-imidazole tautomer driven by effects of electron delocalization. Overall, the inventors believe that this data has significant implications for understanding the molecular physiology of glucosepane-protein adducts. Given that these are found in all human beings, and believed to be directly involved in the pathophysiology underlying various disease states, these results have the potential to provide new directions for developing improved treatments for patients. More broadly, the inventors believe that the brevity and modularity of the disclosed synthesis will render it compatible with the site-specific incorporation of glucosepane into synthetic oligopeptides, preparation of affinity reagents to identify molecular targets of glucosepane, the development of immunogens for raising antibodies against glucosepane, and also, perhaps, the identification of novel therapeutic strategies for glucosepane "crosslink-breaking." Unlike prior investigations, which have been constrained to study glucosepane-modified proteins as highly heterogeneous mixtures, the strategies reported herein have the potential to open up entirely new opportunities for studying AGEs at an unprecedented level of resolution.

Experimental Details

General Information for Chemical Synthesis

Starting materials were used as received unless otherwise noted. All moisture sensitive reactions were performed in an inert, dry atmosphere of nitrogen in oven dried glassware. Reagent grade solvents were used for extractions and flash chromatography. Reaction progress was checked by analytical thin-layer chromatography (TLC, Merck silica gel 60 F-254 plates). The plates were then monitored with UV illumination followed by visualization with appropriate staining reagents such as anisaldehyde, ninhydrin, or KMnO$_4$. Flash column chromatography was performed using silica gel (230-400 mesh) using Teledyne Isco CombiFlash Rf 200 unless otherwise specified. The solvent compositions reported for all chromatographic separations are on a volume/volume (v/v) basis. Infrared (IR) spectra were recorded on a Thermo Nicolet 6700 FT-IR Spectrometer. $^1$H-NMR spectra were recorded on Agilent DD2 400 MHz, 500 MHz, 600 MHz and 800 MHz spectrometer and are reported in parts per million (ppm) on the δ scale relative to CDCl$_3$ (δ 7.26), Methanol-d4 (δ 3.31), ACN-d3 (δ 1.94), D$_2$O (δ 4.79) as an internal standard. Data are reported as follows: chemical shift, multiplicity (s=singlet, d=doublet, t=triplet, q=quartet, br=broad, m=multiplet), coupling constants (Hz), and integration. $^{13}$C-NMR spectra were recorded on Agilent DD2 125 MHz, and 150 MHz spectrometers and are reported in parts per million (ppm) on the δ scale relative to CDCl$_3$ (δ 77.00), Methanol-d4 (δ 49.00), ACN-d3 (δ 1.32). LC-MS analyses were performed on a Waters UPLC/MS instrument equipped with a RP-C18 column (1.7 μm particle size, 2.1×50 mm), dual atmospheric pressure chemical ionization (API)/electrospray (ESI) mass spectrometry detector, and photodiode array detector. Optical rotations were measured at 20° C.; concentrations are in g/100 mL.

Epoxide 8 Synthesis

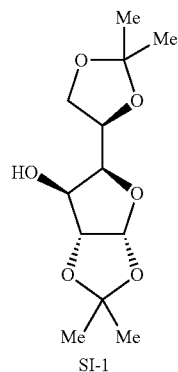

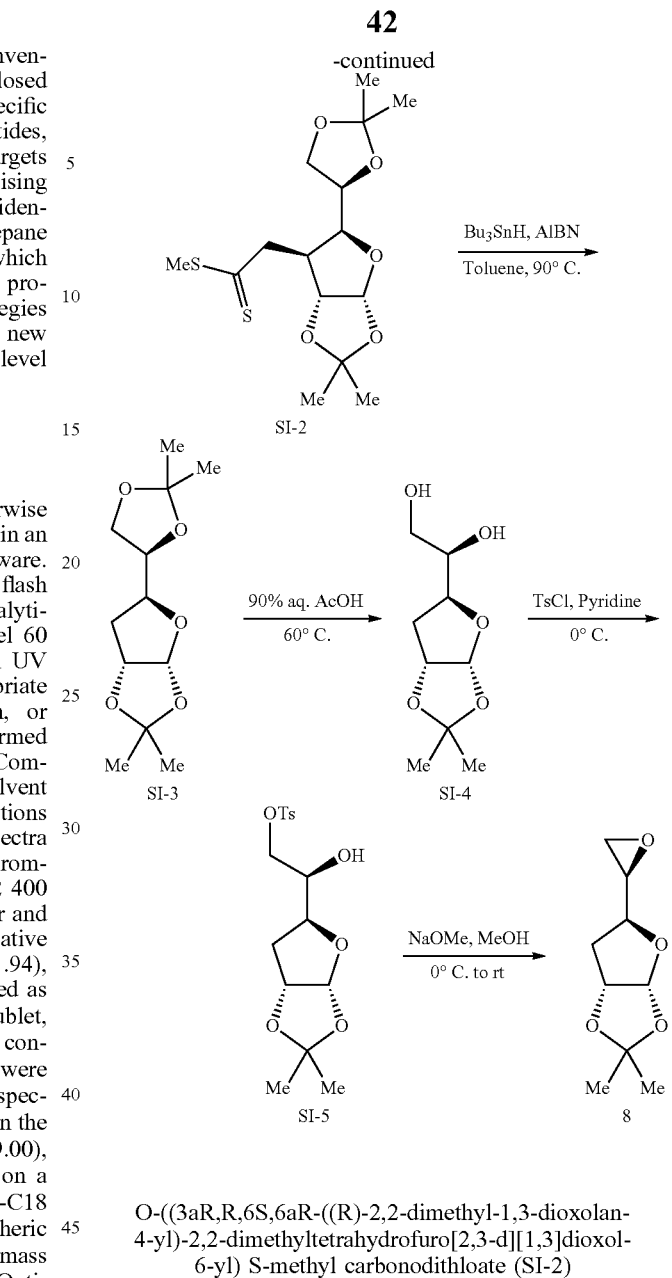

O-((3aR,R,6S,6aR-((R)-2,2-dimethyl-1,3-dioxolan-4-yl)-2,2-dimethyltetrahydrofuro[2,3-d][1,3]dioxol-6-yl) S-methyl carbonodithioate (SI-2)

Diacetone-D-glucose (20 g, 76.8 mmol) was dissolved in dry THF (320 ml) at room temperature and 95% NaH (2.77 g, 115.3 mmol) was added in two portions within 15 minutes with vigorous stirring and gas evolution observed. The reaction mixture was then stirred at room temp for 30 minutes and to the resulting cloudy yellow solution was added CS$_2$ (9.28 mL, 153.7 mmol) dropwise via syringe. This mixture was stirred for 30 minutes and then MeI (8.13 mL, 130.6 mmol) was added dropwise via syringe. Stirring was continued for another 30 minutes, at which point TLC (1:1 Hexanes/EtOAc—KMnO$_4$ stain) indicated complete conversion. The resulting brown solution, containing a white precipitate, was evaporated in vacuo to a thick brown syrup, dissolved in EtOAc (300 mL) and washed with water (300 mL). The aqueous layer was then back extracted twice with EtOAc (200 mL) and the combined organic layers dried over MgSO$_4$, filtered and concentrated in vacuo to a thick dark orange oil. Purification was performed in 2 batches using Teledyne Isco with a normal phase 120 g RediSep column as the stationary phase. Hexanes and EtOAc were used as the mobile phase. Column conditions: 100% hexanes for 2 column volumes (CVs) followed by 0→35% EtOAc over 14 CVs. The title compound was isolated in 99% yield (26.8 g, 76.75 mmol) as a thick yellow oil with spectra matching previously reported values.[1]

(3aR,5S,6aR)-5-((R)-2,2-dimethyl-1,3-dioxolan-4-yl)-2,2-dimethyltetrahydrofuro[2,3-d][1,3]dioxole (SI-3)

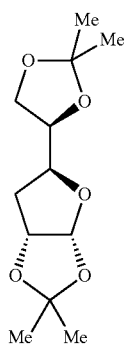

Xanthante SI-2 (14.85 g, 42.4 mmol) was dissolved in dry toluene (210 mL) and then n-Bu$_3$SnH (14.8 mL, 55.1 mmol) and freshly recrystallized AIBN (1.4 g, 8.48 mmol) were added to the solution at room temperature. The reaction vessel was then fitted with a condenser and placed in an oil bath preheated to 90° C. Upon heating, gas evolution was observed. The reaction was stirred at 90° C. for 2 hours, at which point TLC (2:1 Hexanes/EtOAc—KMnO$_4$ stain) indicated complete consumption of starting material. The reaction was then cooled and concentrated in vacuo to give a pale yellow oil. Purification was performed using Teledyne Isco with a normal phase 120 g RediSep column as the stationary phase. Hexanes and EtOAc were used as the mobile phase. Column conditions: 100% hexanes for 1 column volume (CV) followed by 0→5% EtOAc over 1 CV, then hold at 5% EtOAc for 2 CVs, followed by 5%→25% over 10 CVs, and finally hold at 25% EtOAc for 3 CVs. The title compound was isolated in 76% yield (8 g, 32.7 mmol) as a thick yellow oil with spectra matching previously reported values.[1]

(R)-1-((3aR,5S,6aR)-2,2-dimethyltetrahydrofuro[2,3-d][1,3]dioxol-5-yl)ethane-1,2-diol (SI-4)

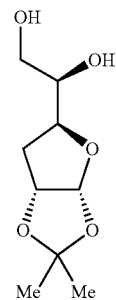 [SMILES: CC1(C)O[C@H]2O[C@H]([C@H](O)CO)C[C@H]2O1]

Acetal SI-3 (2.06 g, 8.46 mmol) was dissolved in 90% aqueous AcOH (6 mL H$_2$O in 54 mL glacial AcOH) and the reaction vessel was then placed in an oil bath preheated to 60° C. The reaction was stirred at this temperature for 45 min (longer reaction times lead to second acetonide deprotection), at which point TLC indicated complete consumption of starting material. The reaction mixture was then cooled to room temperature and concentrated in vacuo. Residual AcOH and water removed by azeotropic evaporation with toluene, and the resulting crude material was placed under high vacuum overnight to give a white solid. Purification was performed using Teledyne Isco with a normal phase 24 g RediSep column as the stationary phase. CH$_2$Cl$_2$ and MeOH were used as the mobile phase. Column conditions: 100% CH$_2$Cl$_2$ for 1 column volume (CV) followed by 0→15% MeOH over 20 CVs. The title compound was isolated in 93% yield (1.60 g, 7.83 mmol) as a white solid with spectra matching previously reported values.[1]

(R)-2(3aR,5S,6aR)-2,2-dimethyltetrahydrofuro[2,3-d][1,3]dioxol-5-yl)-2-hydroxyethyl 4-methylbenzenesulfonate (SI-5)

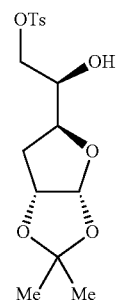 [SMILES: Cc1ccc(S(=O)(=O)OC[C@@H](O)[C@@H]2C[C@H]3OC(C)(C)O[C@H]3O2)cc1]

Diol SI-4 (1.08 g, 5.29 mmol) was dissolved in anhydrous pyridine (26 mL) and cooled to 0° C. before freshly recrystallized tosyl chloride (1.16 g, 6.08 mmol) was added in one portion. The reaction mixture was then stirred at 0° C. while monitoring by TLC (1:1 Hex/EtOAc—KMnO$_4$ stain). Generally, after 8 hrs the reaction showed complete consumption of starting diol and formation of desired monotosylate as the major products as well as the bis tosylate (ratio~5:1—determined by $^1$H NMR of the crude reaction mixture). Upon completion, the solvent was evaporated in vacuo and the resulting crude residue purified by chromatography. Purification was performed using Teledyne Isco with a normal phase 40 g RediSep column as the stationary phase. Hexanes and EtOAc were used as the mobile phase. Column conditions: 95% hexanes for 1 column volume (CV) followed by 5→50% EtOAc over 15 CVs, then 50% EtOAc for 2 CVs followed by 50→75% EtOAc over 2 CVs. The pure tosylate was isolated in 84% yield (1.60 g, 4.46 mmol) as a colorless viscous oil with spectra matching previously reported values.[2]

(3aR,5S,6aR)-2,2-dimethyl-5-((R)-oxiran-2-yl)tetrahydrofuro[2,3-d][1,3]dioxole (8)

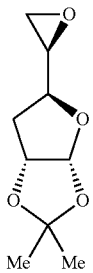

Tosylate SI-5 (1.55 g, 4.32 mmol) was dissolved in anhydrous MeOH (30 mL) and the reaction mixture cooled to 0° C. NaOMe (1.16 g, 21.6 mmol) was then added in one portion. The reaction was stirred at 0° C. for 30 min and then allowed to warm to room temperature, at which point TLC (2:1 Hex/EtOAc—KMnO$_4$ stain) showed complete conversion of starting material to desired product. Approximately 80% of the solvent volume was then removed in vacuo and the resulting mixture was partitioned between equal volumes (30 mL) of water and Et$_2$O. The organic layer was collected and the aqueous layer re-extracted with Et$_2$O (50 mL). The combined Et$_2$O layers were dried over Mg$_2$SO$_4$, filtered, and concentrated in vacuo to afford a pale yellow oil (0.662 g, 3.58 mmol, 83% yield), which was used without further purification. Spectra matched previously reported values.[3]

Ketoazepane 14 Synthesis:
Scheme 1 (Also Presented in FIG. 3, Hereof)

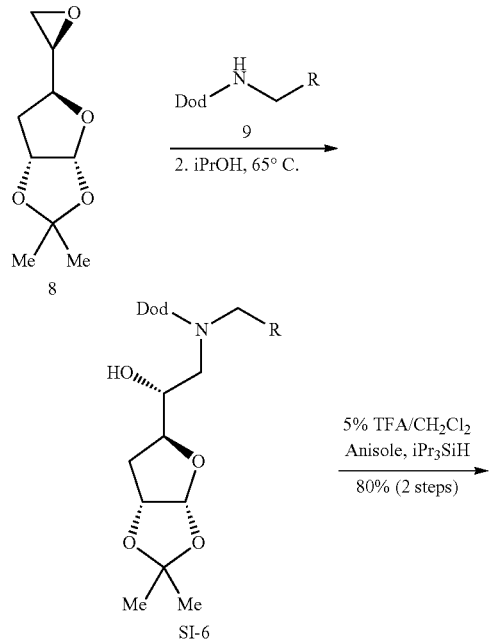

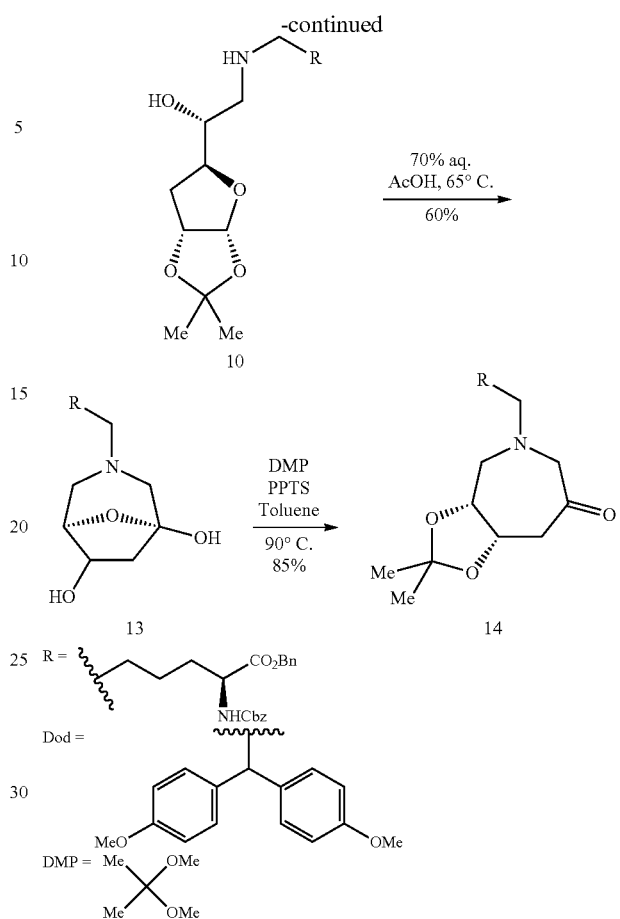

Benzyl N$^2$-((benzyloxy)carbonyl)-N$^6$-(bis(4-methoxyphenyl)methyl)-L-lysine (9)

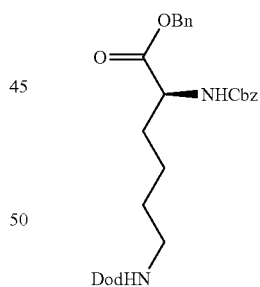

Bis(4-methoxyphenyl)methanol (DodOH) (8.00 g, 32.7 mmol) was added to a flask containing Et$_2$O (200 mL), and the solution was cooled to 0° C. 12M aqueous HCl (16.3 mL, 196 mmol) was then added dropwise, which caused the solution to turn slightly pink. The heterogeneous reaction mixture was warmed to room temperature, stirred vigorously for 30 minutes, and then poured into a separatory funnel. After separation of layers, the organic layer was dried with a 1:1 mixture of MgSO$_4$ and NaHCO$_3$. The solid particles were filtered to give DodCl in Et$_2$O solution, which was immediately used in the next step without further purification.

Finely powdered Lysine-derived benzenesulfonte salt (13.3 g, 25.16 mmol) was added into a flask containing CH$_2$Cl$_2$ (500 mL). After cooling the suspension to 0° C., Et$_3$N (17.5 mL, 125.7 mmol) was added. DodCl solution, freshly prepared as described above, was then added drop-wise over 30 minutes, which caused the solution to turn clear. The reaction mixture was warmed to room temperature, stirred for an additional 2 hours, and then concentrated under vacuum to give crude material as yellow oil. Purification was performed in 2 batches using Teledyne Isco with a normal phase 120 g RediSep column as the stationary phase. CH$_2$Cl$_2$ and EtOAc were used as the mobile phase. Column conditions: 100% CH$_2$Cl$_2$ for 1 column volume (CV) followed by 0→50% EtOAc over 15 CVs. Fully protected lysine derivative 9 was isolated in 88% yield (13.2 g, 22.14 mmol) as thick oil. $^1$H NMR (400 MHz, Chloroform-d) δ 7.37-7.29 (m, 10H), 7.26 (d, J=8.6 Hz, 4H), 6.82 (d, J=8.5 Hz, 4H), 5.28 (d, J=8.3 Hz, 1H), 5.16 (dd, J=19.0, 12.3 Hz, 2H), 5.09 (s, 2H), 4.68 (s, 1H), 4.41 (td, J=7.8, 5.1 Hz, 1H), 3.76 (s, 6H), 2.48 (t, J=6.9 Hz, 2H), 1.82 (dq, J=15.6, 5.3 Hz, 1H), 1.65 (ddt, J=18.4, 13.4, 5.9 Hz, 1H), 1.54-1.22 (m, 4H). $^{13}$C NMR (101 MHz, cdcl$_3$) δ 172.25, 158.32, 155.76, 136.61, 136.11, 135.19, 128.48, 128.40, 128.32, 128.14, 128.03, 127.98, 113.66, 66.94, 66.85, 66.13, 55.09, 53.77, 47.65, 32.39, 29.61, 22.81. HR-MS: (M+1)$^+$= 597.2967 (experimental); exact mass=597.2965 (theoretical)

[α]$_D$=−0.013° (c=5.1, CHCl$_3$)

Benzyl N$^2$-((benzyloxy)carbonyl)-N$^6$-(bis(4-methoxyphenyl)methyl)-N$^6$—((R)-2-((3aR,5S,6aR)-2,2-dimethyltetrahydrofuro[2,3-d][1,3]dioxol-5-yl)-2-hydroxyethyl)-L-lysine (SI-6)

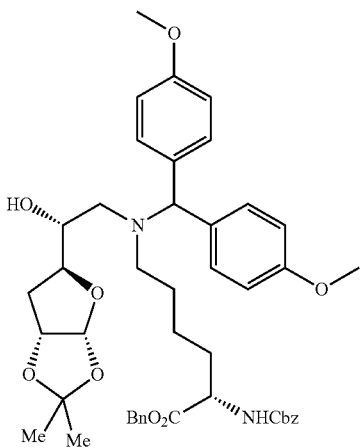

Epoxide 8 (0.662 g, 3.56 mmol) and Dod lysine 9 (2.02 g, 3.39 mmol) were dissolved in iPrOH (17 mL), and the mixture was heated to reflux for 48 hours, at which point TLC (1:1 Hex/EtOAc—CAM stain) indicated complete conversion. The solvent was removed in vacuo and the resulting crude residue purified by chromatography. Purification was performed using Teledyne Isco with a normal phase 80 g RediSep column as the stationary phase. Hexanes and EtOAc were used as the mobile phase. Column conditions: 35% EtOAc for 1 column volume (V) followed by 35→55% EtOAc over 11 CVs. Pure SI-6 was isolated in 88% yield (2.45 g, 3.13 mmol) as a white foam. $^1$H NMR (400 MHz, CDCl$_3$) δ 7.36-7.29 (m, 7H), 7.28-7.14 (m, 4H), 6.82 (dd, J=10.8, 8.6 Hz, 3H), 5.77 (d, J=3.7 Hz, 1H), 5.26 (d, J=8.4 Hz, 1H), 5.18-5.07 (m, 2H), 4.81 (s, 1H), 4.67 (t, J=4.2 Hz, 2H), 4.37 (td, J=8.0, 5.2 Hz, 1H), 3.97 (dt, J=10.0, 4.7 Hz, 1H), 3.78 (s, 7H), 3.76 (s, 3H), 3.70 (dt, J=9.2, 4.8 Hz, 1H), 3.32 (s, 1H), 2.59 (dd, J=13.1, 4.0 Hz, 1H), 2.54-2.33 (m, 3H), 1.91 (dd, J=13.5, 4.5 Hz, 1H), 1.75 (ddd, J=13.4, 10.4, 4.8 Hz, 2H), 1.65-1.53 (m, 2H), 1.47 (s, 3H), 1.46-1.35 (m, 1H), 1.29 (s, 3H), 1.14 (dtd, J=15.7, 10.3, 5.4 Hz, 2H). $^{13}$C NMR (151 MHz, CDCl$_3$) δ 172.32, 158.68, 158.60, 155.92, 136.29, 135.35, 133.90, 132.99, 129.87, 129.54, 128.68, 128.59, 128.54, 128.36, 128.24, 128.22, 128.17, 113.85, 113.77, 111.08, 105.46, 80.46, 80.07, 69.15, 68.28, 67.17, 67.05, 55.27, 55.26, 53.85, 53.47, 50.81, 33.71, 32.57, 26.82, 26.45, 26.19, 22.97.

HR-MS: (M+1)$^+$=783.3834 (experimental); exact mass=783.3857 (theoretical)

IR f (cm$^{-1}$): 1718, 1609, 1508, 1455, 1242, 1165, 1019, 822, 736, 697.

[α]$_D$=+0.028° (c=4.3, CHCl$_3$)

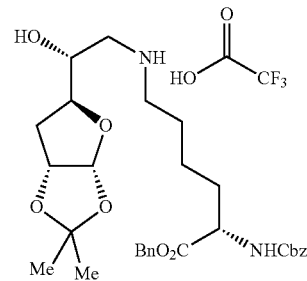

Benzyl N$^2$-((benzyloxy)carbonyl)-N$^6$—((R)-2-((3aR,5S,6aR)-2,2-dimethyltetrahydrofuro[2,3-d][1,3]dioxol-5-yl)-2-hydroxyethyl)-L-lysinate 2,2,2-trifluoroacetate (10)

Dod lysine derivative SI-6 (1.00 g, 1.28 mmol) was dissolved in anhydrous CH$_2$Cl$_2$ (12.35 mL) and cooled to 0° C. before TIPS (1.3 mL, 6.39 mmol), anisole (0.208 mL, 1.92 mmol) and TFA (0.650 mL) were sequentially added to the cooled reaction and allowed to stir at 0° C. while monitoring by TLC (1:2 Hex/EtOAc, CAM stain—a 10 □l aliquot was quenched with aqueous NaHCO$_3$ before spotting on the TLC plate.) Upon completion (approx. 6 h) the reaction was quenched at 0° C. with aqueous NaHCO$_3$ (20 mL) and the mixture transferred to a separatory funnel with the aid of CH$_2$Cl$_2$ (20 mL). The organic layer was drawn off and the aqueous layer was then re-extracted with two portions of CH$_2$Cl$_2$ (20 mL). The combined organic extracts were dried over anhydrous Mg$_2$SO$_4$, filtered, and evaporated to dryness. The resulting crude residue was purified by chromatography. Purification was performed using Teledyne Isco with a normal phase 12 g RediSep column as the stationary phase. CH$_2$Cl$_2$ and MeOH were used as the mobile phase. Column conditions: 100% CH$_2$Cl$_2$ for 3 column volumes (CVs) followed by 0→15% MeOH over 20 CVs, then 15% MeOH for 7 CVs. Pure secondary amine-TFA salt 10 was isolated in 91% yield (0.781 g, 1.16 mmol) as a pale yellow viscous oil.

$^1$H NMR (600 MHz, CDCl$_3$) δ 7.38-7.26 (m, 10H), 5.75 (d, J=3.6 Hz, 1H), 5.56 (d, J=8.2 Hz, 1H), 5.16 (q, J=12.2 Hz, 2H), 5.07 (t, J=10.8 Hz, 2H), 4.69 (t, J=4.1 Hz, 1H), 4.37 (tt, J=8.8, 3.5 Hz, 1H), 4.07 (ddd, J=10.7, 6.4, 4.5 Hz, 1H), 3.96 (ddd, J=9.8, 6.3, 2.9 Hz, 1H), 3.10 (dd, J=12.6, 2.9 Hz, 1H), 2.91 (dd, J=12.7, 9.9 Hz, 1H), 2.86 (t, J=7.8 Hz, 2H), 2.18 (dd, J=13.5, 4.5 Hz, 1H), 1.84 (qd, J=10.8, 8.6, 3.2 Hz, 1H), 1.74-1.61 (m, 4H), 1.47 (s, 3H), 1.35 (qd, J=10.9, 9.5, 4.9 Hz, 2H), 1.29 (s, 3H). $^{13}$C NMR (151 MHz, CDCl$_3$) δ 172.12, 156.19, 136.31, 135.34, 128.77, 128.67, 128.65, 128.51, 128.33, 128.26, 111.71, 105.73, 80.44, 79.23, 68.69, 67.41, 67.20, 53.73, 50.95, 48.16, 35.42, 32.04, 26.84, 26.21, 25.40, 22.35.

HR-MS: (M+1)$^+$=557.2898 (experimental); exact mass=557.2863 (theoretical)

IR f (cm$^{-1}$) $\lambda_{max}$: 1672, 1528, 1455, 1375, 1200, 1132, 1055, 1019, 835, 799, 736, 721, 697.

[α]$_D$=−0.038° (c=5.4, CHCl$_3$)

Benzyl (S)-2-(((benzyloxy)carbonyl)amino)-6-((1R,5R,6S)-1,6-dihydroxy-8-oxa-3-azabicyclo[3.2.1]octan-3-yl)hexanoate (13)

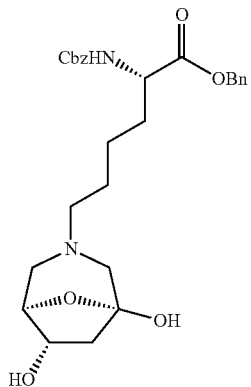 [SMILES: O=C(N[C@@H](CCCCN1C[C@H]2O[C@](O)(C[C@@H]2O)C1)C(=O)OCc1ccccc1)OCc1ccccc1]

Lysine derivative 10 (1.60 g, 2.39 mmol) was dissolved in 70% aqueous AcOH (24 mL) and the reaction mixture heated to 65° C. Upon complete consumption of starting material (~36 h), as determined by LCMS analysis of the crude reaction mixture, the solvent was removed in vacuo and the resulting brown residue dissolved in ACN (24 mL) and heated at 65° C. for 2 hrs. The reaction was then cooled and evaporated to dryness, and the resulting residue was purified by chromatography. Purification was performed using Teledyne Isco with a normal phase 40 g RediSep column as the stationary phase. Hexanes and EtOAc were used as the mobile phase. Column conditions: 70% EtOAc for 4 column volumes (CVs) followed by 70→90% EtOAc over 16 CVs, 90% EtOAc for 6 CVs, 90→100% EtOAc over 1 CV, and finally 100% EtOAc over 7 CVs. Pure azepane acetal 13 was isolated in 60% yield (0.715 g, 1.43 mmol) as a pale yellow viscous oil.

$^1$H NMR (500 MHz, MeOH-d4) δ 7.32 (dtt, J=19.0, 6.6, 3.1 Hz, 10H), 5.17 (dd, J=31.6, 12.2 Hz, 2H), 5.09 (dd, J=20.5, 12.4 Hz, 2H), 4.23 (ddd, J=14.4, 8.3, 4.1 Hz, 2H), 4.01-3.96 (m, 2H), 2.64 (dd, J=11.0, 5.5 Hz, 2H), 2.43 (dd, J=12.7, 7.4 Hz, 1H), 2.27 (t, J=6.9 Hz, 2H), 2.00 (dd, J=10.6, 7.4 Hz, 2H), 1.82 (dq. J=13.2, 7.1, 6.4 Hz, 1H), 1.68 (dq, J=14.2, 7.6, 6.9 Hz, 1H), 1.56 (ddt, J=12.4, 2.5, 1.0 Hz, 1H), 1.41 (dh, J=29.2, 7.8 Hz, 4H). $^{13}$C NMR (126 MHz, MeOH-d4) δ 174.00, 158.66, 138.16, 137.27, 129.56, 129.45, 129.30, 129.24, 128.97, 128.77, 104.65, 83.27, 74.93, 67.79, 67.64, 62.38, 58.04, 55.48, 46.59, 32.29, 26.78, 24.38.

HR-MS: (M+1)$^+$=499.2444 (experimental); exact mass=499.2423 (theoretical)

IR f (cm$^{-1}$) $\lambda_{max}$: 3324.5, 2947, 1717, 1527, 1454, 1393, 1341, 1260, 1185, 1057, 954, 738, 698.

[α]$_D$=−0.83° (c=6.5, CHCl$_3$)

Benzyl (S)-2-(((benzyloxy)carbonyl)amino)-6-((3aR,8aS)-2,2-dimethyl-7-oxohexahydro-5H-[1,3]dioxolo[4,5-c]azepin-5-yl)hexanoate (14)

Acetal 13 (0.650 g, 1.30 mmol) was dissolved in anhydrous toluene (13 mL), and PPTS (0.066 g, 0.26 mmol) and 2,2-dimethoxy propane (1.6 mL, 13.0 mmol) were sequentially added. The resulting reaction mixture was heated to 95° C. and monitored by TLC (2:1 Hex/EtOAc) and LCMS. Upon complete consumption of starting material (~18 h) the reaction mixture was cooled to room temperature and partitioned between equal volumes (20 mL) of CH$_2$Cl$_2$ and saturated aqueous NaHCO$_3$. The bottom organic layer was drawn off and the aqueous layer was then washed twice with CH$_2$Cl$_2$ (20 mL). The combined organic layers were dried over anhydrous Na$_2$SO$_4$, filtered, and evaporated to dryness. The resulting dark brown residue was purified by column chromatography using SiO$_2$ as stationary phase and 3:2 Hexanes/EtOAc containing 2% NEt$_3$ as the mobile phase. The title compound was isolated in 85% yield (0.595 g, 1.11 mmol) as pale yellow viscous oil.

$^1$H NMR (600 MHz, CDCl$_3$) δ 7.39-7.30 (m, 10H), 5.30 (d, J=8.4 Hz, 1H), 1.33-1.23 (m, 2H), 5.17 (dd, J=34.2, 12.0 Hz, 2H), 5.10 (s, 2H), 4.43 (td, J=8.0, 5.2 Hz, 1H), 4.24 (ddd, J=6.5, 5.2, 3.8 Hz, 1H), 3.14 (dd, J=21.5, 17.0 Hz, 2H), 1.49-1.36 (m, 1), 4.09 (dt, J=7.5, 5.0 Hz, 1H), 3.00 (dd, J=11.4, 6.9 Hz, 1H), 2.97 (dd, J=11.3, 3.8 Hz, 1H), 2.70 (dd, J=14.9, 4.8 Hz, 1H), 2.60 (dd, J=14.7, 7.7 Hz, 2H), 2.47 (t, J=6.6 Hz, 2H), 1.87 (ddt, J=14.7, 10.1, 5.0 Hz, 1H), 1.68 (dddd, J=13.7, 9.5, 7.2, 5.8 Hz, 1H), 1.41 (s, 3H), 1.31 (s, 3H). $^{13}$C NMR (151 MHz, CDCl$_3$) δ 208.97, 172.33, 155.93, 136.25, 135.33, 128.72, 128.62, 128.39, 128.31, 128.22, 108.16, 76.06, 73.98, 68.28, 67.21, 67.09, 57.42, 55.44, 53.90, 43.27, 32.53, 28.36, 27.29, 25.87, 22.63.

HR-MS: (M+1)$^+$=539.2757 (experimental); exact mass=539.2744 (theoretical)

IR f (cm$^{-1}$) $\square_{max}$: 2936, 1714, 1523, 1454, 1380, 1341, 1240, 1213, 1046, 909, 861, 735, 697.

[α]$_D$=+0.021° (c=4.9, CHCl$_3$)

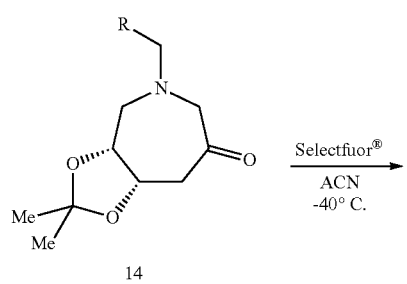

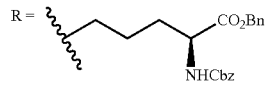

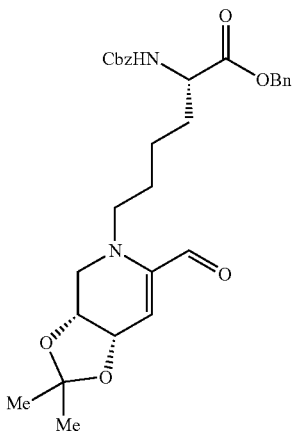 [SMILES: CC1(C)O[C@H]2C=C(C=O)N(CCCC[C@H](NC(=O)OCc3ccccc3)C(=O)OCc3ccccc3)C[C@H]2O1]

Benzyl (S)-2-((benzyloxy)carbonyl)amino)-6-((3aR,7aS)-6-formyl-2,2-dimethyl-3,7a-dihydro-[1,3]dioxolo[4,5-c]pyridin-(4H)-yl)hexanoate (17)

Ketone 14 (0.040 g, 0.0745 mmol) was dissolved in anhydrous ACN (0.750 mL) under N$_2$, and the resulting solution was cooled to −40° C. Selectfluor® (0.032 g, 0.0892 mmol) was added in one portion and the resulting reaction mixture was stirred at −40° C. for 2 hours. The reaction was then quenched by addition of saturated aqueous NaHCO$_3$ (0.300 mL) and resulting biphasic mixture was allowed to warm to room temp with vigorous stirring. Mixture was then partitioned between equal volumes (5 mL) of saturated aqueous NaHCO$_3$ and CH$_2$Cl$_2$, bottom organic layer drawn off and remaining aqueous layer extracted with CH$_2$Cl$_2$ (2×). The combined organic layers were dried over anhydrous Na$_2$SO$_4$, filtered, and evaporated to dryness. The resulting dark brown residue was purified by column chromatography using SiO$_2$ as stationary phase and 3:1 Hexanes/EtOAc containing 1% NEt$_3$ as the mobile phase. The title compound was isolated in 80% yield (0.032 g, 0.596 mmol) as pale yellow viscous oil.

$^1$H NMR (600 MHz, CDCl$_3$) δ 9.11 (s, 1H), 7.34 (tt, J=10.8, 5.4 Hz, 10H), 5.49 (d, J=4.1 Hz, 1H), 5.34 (d, J=8.4 Hz, 1H), 5.16 (q, J=12.3 Hz, 2H), 5.10 (s, 2H), 4.63 (t, J=5.0 Hz, 1H), 4.40 (td, J=7.9, 5.2 Hz, 1H), 4.14 (dt, J=8.9, 4.9 Hz, 1H), 3.33 (t, J=7.6 Hz, 2H), 3.12 (dd, J=12.9, 4.1 Hz, 1H), 2.85 (dd, J=12.9, 8.0 Hz, 1H), 1.84 (ddt, J=15.8, 10.8, 5.3 Hz, 1H), 1.73-1.61 (m, 1H), 1.50-1.19 (m, 4H), 1.44 (s, 3H), 1.39 (s, 3H). $^{13}$C NMR (126 MHz, CDCl$_3$) δ 189.60, 172.19, 155.85, 145.98, 136.31, 135.36, 128.63, 128.60, 128.49, 128.43, 128.34, 128.27, 128.16, 128.12, 128.05, 127.91, 118.32, 108.72, 71.54, 69.63, 67.09, 66.98, 53.91, 50.18, 50.12, 32.45, 28.52, 28.40, 26.00, 22.27.

HR-MS: (M+1)$^+$=536.2530 (experimental); exact mass=536.2523 (theoretical)

IR f (cm$^{-1}$) □$_{max}$: 2950, 1695, 1499, 1451, 1240, 1213, 1046, 909, 861, 801, 693.

[α]$_D$=+0.017° (c=1.3, CHCl$_3$)

Iso-Imidazole Synthesis
(Oxidation/Addition/Reduction Sequence)

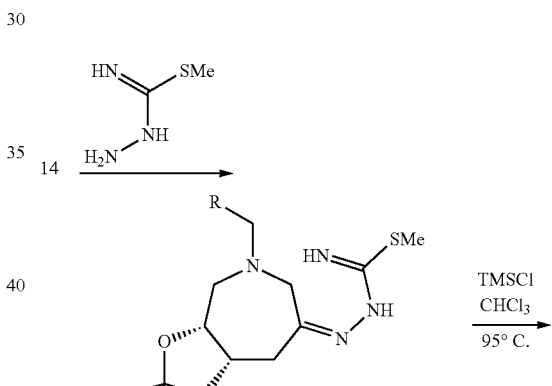

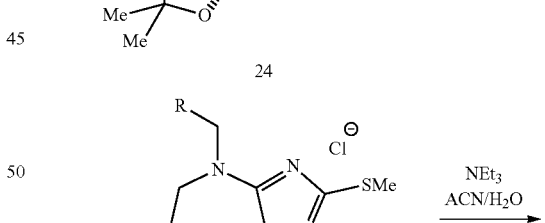

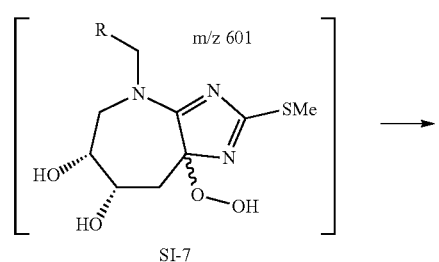

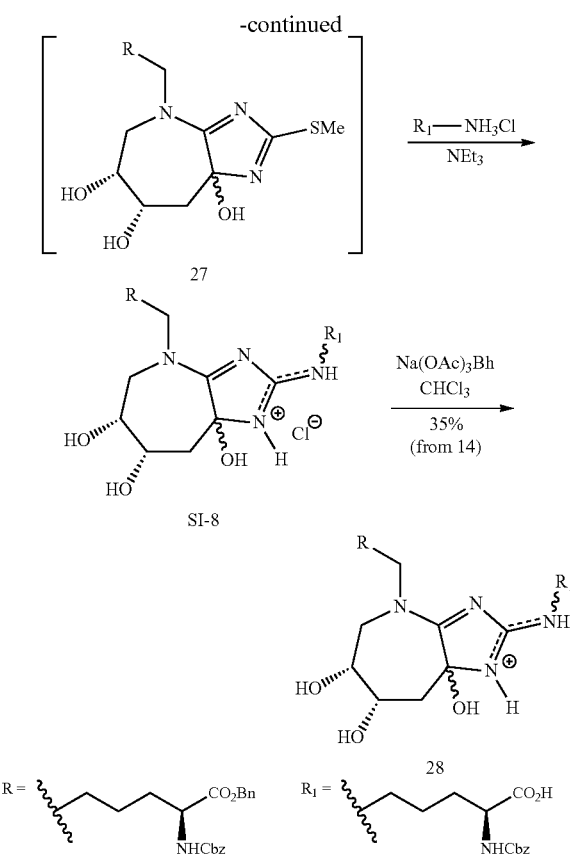

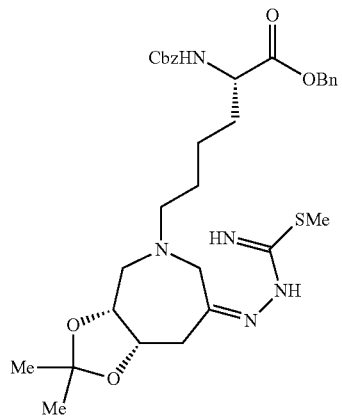 [SMILES: CSC(=N)N/N=C1/C[C@@H]2OC(C)(C)O[C@@H]2CN(CCCC[C@H](NC(=O)OCc2ccccc2)C(=O)OCc2ccccc2)C1]

Benzyl (S)-2-(((benzyloxy)carbonyl)amino)-6-((3aR,8aS,Z)-7-(2-(imino(methylthio)methyl)hydrazono)-2,2-dimethylhexahydro-5H-[1,3]dioxolo[4,5-c]azepin-5-yl)hexanoate (24)

Ketone 24 (0.560 g, 1.04 mmol) was dissolved in anhydrous MeOH (10 mL) and SMe-semicarbazide hydroiodide (0.267 g, 1.14 mmol) was added in one portion at room temperature. The resulting reaction mixture was stirred and monitored by LCMS. Upon complete consumption of starting material (~3 h), the mixture was evaporated to dryness to afford a orange-yellow foam. This material was then portioned between equal volumes (10 mL) of $CH_2Cl_2$ and 1 M NaOH and the resulting biphasic mixture stirred vigorously for 5 min. After separation of layers, the organic phase was drawn off and the aqueous layer re-extracted twice with $CH_2Cl_2$ (10 mL). The combined organic layers were dried over anhydrous $Na_2SO_4$, filtered, and concentrated to dryness. The resulting crude pale orange viscous oil was purified by column chromatography using $SiO_2$ as stationary phase and 2:3 Hexanes/EtOAc containing 3% $NEt_3$ as the mobile phase. The desired semicarbazone was isolated in 74% yield (0.482 g, 0.771 mmol) as a pale yellow viscous oil (1.5:1 mixture of E/Z isomers).

Minor Isomer:
$^1$H NMR (600 MHz, Acetonitrile-d$_3$) δ 7.40-7.29 (m, 10H), 6.01 (s, 1H), 5.64 (s, 1H), 5.13 (q, J=12.4 Hz, 2H), 5.06 (dd, J=14.4, 12.5 Hz, 2H), 4.22-4.17 (m, 1H), 4.16-4.11 (m, 1H), 4.06 (q, J=5.9 Hz, 1H), 3.66 (d, J=16.6 Hz, 1H), 3.40 (d, J=16.5 Hz, 1H), 2.82 (dd. J=12.5, 8.4 Hz, 1H), 2.63 (dd, J=12.5, 3.8 Hz, 1H), 2.61 (d, J=1.5 Hz, 2H), 2.43 (q, J=6.2 Hz, 2H), 2.34 (s, 3H), 1.80 (dt, J=15.5, 7.1 Hz, 1H), 1.70-1.62 (m, 1H), 1.43-1.37 (m, 2H), 1.35 (s, 3H), 1.34-1.26 (m, 2H), 1.26 (s, 3H).

Major Isomer:
$^1$H NMR (600 MHz, Acetonitrile-d3) δ 7.40-7.29 (m, 10H), 6.01 (d. J=8.2 Hz, 1H), 5.66 (s, 1H), 5.13 (q, J=12.5 Hz, 2H), 5.06 (s, 2H), 4.21-4.18 (m, 1H), 4.19-4.16 (m, 1H), 4.13 (q, J=6.2 Hz, 1H), 3.43 (dd, J=11.4, 4.8 Hz, 1H), 3.24 (dd, J=29.8, 13.2 Hz, 2H), 2.78-2.75 (m, 2H), 2.49-2.40 (m, 2H), 2.38 (s, 3H), 1.83-1.75 (m, 1H), 1.69-1.63 (m, 1H), 1.49-1.39 (m, 2H), 1.36 (s, 3H), 1.31-1.25 (m, 2H), 1.24 (s, 3H).

Mixture of E/Z Isomers
$^{13}$C NMR (151 MHz, Acetonitrile-d$_3$) δ 173.39, 161.90, 161.19, 159.85, 159.68, 157.16, 138.10, 137.11, 129.50, 129.44, 129.17, 129.02, 128.91, 128.90, 128.69, 108.57, 108.29, 76.95, 76.78, 74.32, 67.40, 67.10, 63.50, 58.15, 58.11, 56.78, 56.63, 55.29, 55.26, 54.71, 38.14, 32.75, 32.13, 32.10, 28.60, 28.12, 28.08, 27.99, 27.65, 25.90, 25.26, 25.19, 23.94, 23.88, 12.73.

HR-MS: (M+1)$^+$=626.3012 (experimental); exact mass=626.3016 (theoretical)

IR f (cm$^{-1}$): 2931, 1716, 1592, 1533, 1454, 1380, 1244, 1211, 1154, 1040, 908, 734, 697.

[α]$_D$=+0.046° (c=1.2, CHCl$_3$)

Benzyl (2S)-2-(((benzyloxy)carbonyl)amino)-6-((5aR,8aS)-7,7-dimethyl-2-(methylthio)-5a,8a,9,9a-tetrahydro-[1,3]dioxolo[4,5-e]imidazo[4,5-b]azepin-4(5B)-yl)hexanoate (26)

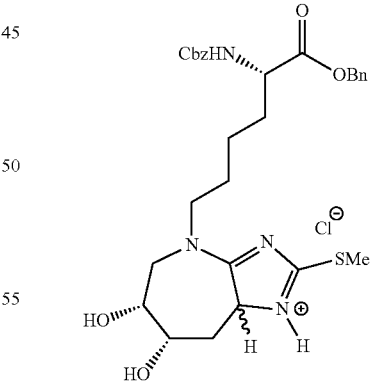

Semicarbazone 24 (0.050 g, 0.0799 mmol) was dissolved in anhydrous and degassed (freeze/pump/thaw) CHCl$_3$ (0.800 mL) before freshly distilled and degassed TMSCl (0.029 mL, 0.239 mmol) was added to the solution at room temperature. The reaction vessel was sealed under argon and placed in an oil bath preheated to 95° C. The reaction was stirred at this temperature for 24 h, at which point LCMS analysis of the resulting dark reddish-brown mixture indicated complete consumption of starting material and formation of desired thioisoimidazole ([M+H]⁺ 609). The reaction mixture was then treated with water (0.020 mL) and stirred at room temperature for 1 hour. LCMS analysis indicated full deprotection of the acetonide group ([M+H]⁺ 596). The reaction mixture was cooled in an ice bath and diluted with 1 M aqueous HCl (1.00 mL) and $CH_2Cl_2$ (0.300 mL). The resulting biphasic mixture was stirred vigorously for 5 min, then layers were allowed to separate, the bottom organic layer drown off, and the aqueous layer re-extracted twice with $CH_2Cl_2$ (1.00 mL). The combined organic layers were dried over anhydrous $Na_2SO_4$, filtered, and concentrated to dryness. The title compound (0.052 g, crude mass) was isolated as a HCl salt and carried on without further purification.

For characterization purposes the title compound was purified by preparatory HPLC with a SunFire Prep C18 OBD 5 μm 10×150 mm reversed-phase column as the stationary phase. $H_2O$ and MeCN both buffered with 0.1% trifluoroacetic acid were used as the mobile phase. HPLC conditions: UV collection 254 nm, flow rate 5 mL % min, 25%→60% MeCN linear gradient over 32 minutes. The HPLC fractions were combined and lyophilized and title compound was isolated as a pale red fluffy solid.

Prep HPLC Retention Time: 12.72 min (minor isomer) & 13.18 min (major isomer).

Due to rapid epimerization of the two isolated isomers, the title compound was characterized as a mixture of epimers.

¹H NMR (600 MHz, Acetonitrile-d₃) δ 7.37 (dq, J=11.8, 8.0 Hz, 20H), 6.03 (d, J=8.4 Hz, 1H), 6.00 (d, J=8.3 Hz, 1H), 5.30 (dd, J=12.1, 2.4 Hz, 1H), 5.18-5.12 (m, 4H), 5.11-5.05 (m, 4H), 4.86 (dd, J=12.3, 3.2 Hz, 1H), 4.22 (qd, J=9.0, 4.9 Hz, 3H), 4.12-4.04 (m, 2H), 3.89 (dt, J=14.0, 7.3 Hz, 1H), 3.82 (d, J=11.2 Hz, 1H), 3.77-3.63 (m, 4H), 3.56-3.41 (m, 2H), 3.17 (d, J=14.5 Hz, 1H), 2.63 (s, 6H), 2.39 (dt, J=14.2, 3.9 Hz, 1H), 2.20 (td, J=12.8, 3.9 Hz, 1H), 1.90-1.60 (m, 10H), 1.37 (pd, J=7.6, 2.1 Hz, 4H). ¹³C NMR (151 MHz, Acetonitrile-d₃) δ 185.48, 185.45, 184.65, 183.32, 173.24, 173.18, 157.23, 138.08, 137.10, 129.54, 129.48, 129.22, 129.03, 128.96, 128.70, 72.18, 70.82, 70.29, 69.24, 67.50, 67.48, 67.18, 67.16, 63.45, 61.80, 55.03, 54.99, 54.75, 53.55, 53.47, 51.75, 34.55, 31.76, 31.72, 30.22, 26.96, 26.77, 23.16, 23.12, 14.70, 14.67.

HR-MS: (M+1)⁺=569.2440 (experimental); exact mass=569.2428 (theoretical)

IR f (cm⁻¹): 3209, 2938, 1677, 1642, 1521, 1431, 1365, 1202, 1136, 800, 722, 699.

(6R,7S)-4-((S)-6-(benzyloxy)-5-(((benzyloxy)carbonyl)amino)-6-oxohexyl)-6,7,8a-trihydroxy-2-(methylthio)-4,5,6,7,8,8a-hexahydromidazo[4,5-b]azepin-1-ium trifluoroacetate (27)

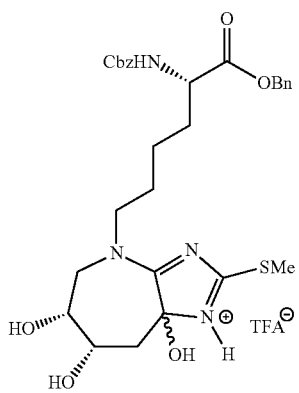 [SMILES: CSC1=[NH+]C2(O)C[C@H](O)[C@H](O)CN(CCCC[C@H](NC(=O)OCc3ccccc3)C(=O)OCc3ccccc3)C2=N1]

Crude isothioimdazole 26 was dissolved in a 4:1 mixture of acetonitrile (0.640 mL) and DI water (0.160 mL) before $NEt_3$ (0.011 mL, 0.0799 mmol) was added. The resulting dark brown reaction mixture was stirred at room temperature under ambient air. LCMS analysis of the dark reddish-brown mixture indicated complete consumption of starting material (~10 h) and formation of desired oxothioisoimidazole. This reaction mixture was carried on to the subsequent addition step.

For characterization purposes the title compound was purified by preparatory HPLC with a SunFire Prep C18 OBD 10 □m 19×150 mm reversed-phase column as the stationary phase. $H_2O$ and MeCN both buffered with 0.1% trifluoroacetic acid were used as the mobile phase. HPLC conditions: UV collection 254 nm, flow rate 20 mL/min, 34%→45% MeCN linear gradient over 30 minutes. The HPLC fractions were combined and lyophilized. The title compound isolated as a white solid.

Prep HPLC Retention Time: 6.92 min

¹H NMR (500 MHz, Acetonitrile-d₃) δ 7.35 (dd, J=9.7, 6.9 Hz, 10H), 6.03 (d, J=8.2 Hz, 1H), 5.12 (dd. J=16.1, 12.6 Hz, 2H), 5.06 (dd, J=16.3, 12.9 Hz, 2H), 4.23 (d, J=14.8 Hz, 1H), 4.19 (dd. J=8.5, 5.1 Hz, 1H), 4.08-4.04 (m, 1H), 4.01 (dd, J=11.4, 3.7 Hz, 1H), 3.92 (dt, J=14.1, 7.4 Hz, 1H), 3.52 (dd, J=14.8, 6.6 Hz, 1H), 3.41 (dt, J=13.5, 6.6 Hz, 1H), 2.58 (s, 3H), 2.32 (dd, J=13.8, 4.1 Hz, 1H), 2.08-1.99 (m, 1H), 1.83 (ddd, J=13.3, 8.2, 3.8 Hz, 1H), 1.67 (dtt, J=21.2, 14.0, 6.7 Hz, 3H), 1.35 (p, J=7.6 Hz, 2H). ¹³C NMR (126 MHz, cd₃cn) δ 185.87, 180.20, 173.22, 157.24, 138.09, 137.11, 129.54, 129.48, 129.21, 129.04, 128.95, 128.70, 92.87, 70.52, 70.50, 67.49, 67.18, 55.65, 55.06, 52.34, 35.06, 31.74, 26.72, 23.14, 14.55.

HR-MS: (M+1)⁺=585.2363 (experimental); exact mass=585.2377 (theoretical)

[α]_D=−0.018° (c=2.3, ACN-d4)

(6R,7S)-4-((S)-6-(benzyloxy)-5-(((benzyloxy)carbonyl)amino)-6-oxohexyl)-2-(((S)-4-(((benzyloxy)carbonyl)amino)-4-carboxyl)amino)-6,7,8a-trihydroxy-4,5,6,7,8,8a-hexahydroimidazo[4,5-b]azepin-1-ium (SI-8)

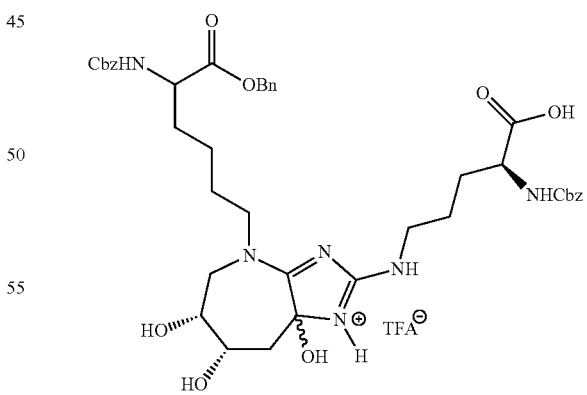

To the reaction mixture obtained in the previous step, Z-Orn-OH—HCl (0.029 g, 0.0959 mmol) was added to the reaction flask, followed by $NEt_3$ (0.011 mL, 0.0799 mmol). The resulting reaction mixture was heated to 50° C. and stirred until LCMS analysis of the reaction mixture indicated complete consumption of starting material and formation of oxidized adduct SI-8 (M+H−803.4). The reaction mixture was then cooled in an ice bath and diluted with 1M aqueous HCl (1.0 mL) and CH$_2$Cl$_2$ (0.300 mL). The resulting biphasic mixture was stirred vigorously for 5 min, then layers were allowed to separate, the bottom organic layer drown off, and the aqueous re-extracted twice with CH$_2$Cl$_2$ (1.0 mL). The combined organic layers were dried over anhydrous Na$_2$SO$_4$, filtered, and concentrated to dryness. The title compound (0.080 g, crude mass) was isolated as an HCl salt in an undetermined mixture of epimers and carried on to the next step without further purification.

For characterization purposes the title compound was purified by preparative HPLC. Preparatory HPLC was performed with a Macherey-Nagel Nucleosil Prep C18, 7 □m, 21×250 mm reversed-phase column as the stationary phase. H$_2$O and MeCN both buffered with 0.1% trifluoroacetic acid were used as the mobile phase. HPLC conditions: UV collection 254 nm, flow rate 20 mL % min. 25%→45% MeCN linear gradient over 35 minutes and then isocratic elution with 45% McCN over 5 min. The HPLC fractions were combined and lyophilized.

Prep HPLC Retention Time: 39.57 min $^1$H NMR (600 MHz, 15% D$_2$O, Acetonitrile-d$_3$) δ 7.39-7.26 (m, 15H), 5.13-4.98 (m, 6H), 4.16 (dtd. J=26.4, 9.2, 5.3 Hz, 2H), 4.08-4.01 (m, 1H), 3.99 (dt, J=6.8, 3.3 Hz, 1H), 3.93-3.73 (m, 3H), 3.45-3.36 (m, 2H), 3.29-3.14 (m, 2H), 2.22 (ddd, J=18.9, 13.8, 4.4 Hz, 1H), 1.99-1.95 (m, 1H), 1.88-1.76 (m, 2H), 1.71-1.54 (m, 6H), 1.32 (dtd, J=14.6, 7.9, 6.9, 4.3 Hz, 2H). $^{13}$C NMR (151 MHz, 15% D$_2$O, Acetonitrile-d$_3$) δ 179.82, 179.16, 178.82, 175.20, 174.98, 173.76, 173.73, 166.53, 165.97, 165.66, 161.73, 161.61, 157.91, 157.82, 157.73, 157.71, 137.81, 137.78, 136.88, 129.59, 129.57, 129.52, 129.50, 129.30, 129.27, 129.03, 129.00, 128.73, 128.71, 128.69, 92.71, 92.44, 90.27, 89.49, 72.12, 71.80, 70.59, 70.34, 70.31, 70.13, 70.11, 69.79, 67.73, 67.69, 67.48, 67.44, 67.38, 55.68, 55.07, 54.99, 54.81, 54.73, 54.37, 54.29, 51.89, 51.83, 51.72, 42.77, 42.55, 42.33, 40.10, 39.95, 35.70, 33.79, 31.56, 29.49, 29.33, 29.03, 26.66, 26.52, 26.38, 25.62, 25.46, 23.17, 23.13.

HR-MS: (M+1)$^+$=803.3595 (experimental); exact mass=803.3610 (theoretical)

IR f (cm$^{-1}$): 3294, 1681, 1610, 1533, 1426, 1345, 1203, 1139, 1055, 840, 740, 723, 698.

[α]$_D$=−0.055° (c=2.7, ACN-d4)

2,2,2-trifluoro-1λ$^3$-ethan-1-one, (6R,7S,Z)-4S)-4-((S)-6-(benzyloxy)-5-(((benzyloxy)carbonyl)amino-6-oxohexyl)-2-(((S)-4-(((benzyloxy)carbonyl)amino)-4-carboxybutyl)-λ$^4$-azanylidene)-6,7-dihydroxy-1,2,4,5,6,7,8,a-octahydroimidazo[4,5-b]azepin-1-ium salt (28)

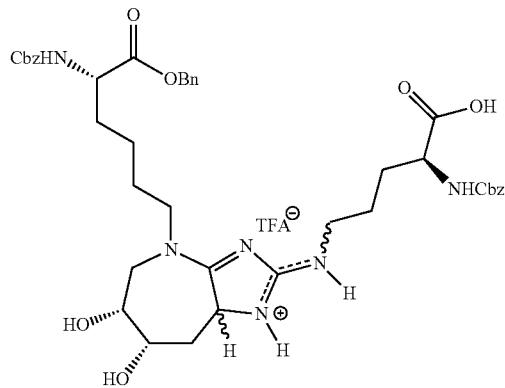

Crude SI-8 was dissolved in anhydrous CHCl$_3$ (0.800 mL) and Na(AcO)$_3$BH (0.084 g, 0.400 mmol) was added in one portion. The resulting reaction mixture was stirred at room temperature for 15 hours. LCMS analysis of the dark reddish-brown mixture indicated complete consumption of starting material and formation of tittle compound ([M+H]$^+$ 877). The reaction was quenched by drop wise addition of 10% aqueous TFA (1 mL). The resulting biphasic mixture was stirred vigorously for 5 min, then layers were allowed to separate, the bottom layer drawn off, and the aqueous layer re-extracted twice with CH$_2$Cl$_2$ (1.0 mL). The combined organic layers were dried over anhydrous Na$_2$SO$_4$, filtered, and concentrated to a dark brown residue containing a 4:1 mixture of epimers (0.078 g, crude mass) which was separated by preparative scale HPLC. Preparatory HPLC was performed with a Macherey-Nagel Nucleosil Prep C18, 7 □m, 21×250 mm reversed-phase column as the stationary phase. H$_2$O and MeCN both buffered with 0.1% trifluoroacetic acid were used as the mobile phase. HPLC conditions: UV collection 254 nm, flow rate 20 mL/min, 25%→47% MeCN linear gradient over 50 minutes and then isocratic elution with 47% MeCN over 9 minutes. The HPLC fractions were combined and lyophilized. Title compound was isolated in 35% yield (0.025 g, 0.280 mmol, >95% pure) as a white fluffy solid.

Major 8a(S) Epimer:

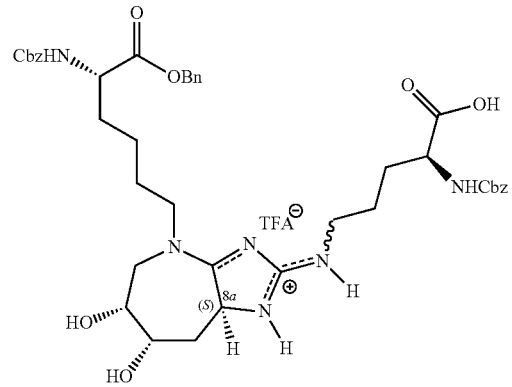

Prep HPLC retention time: 50.40 minutes $^1$H NMR (600 MHz, Methanol-d$_4$) δ 7.35-7.24 (m, 15H), 5.18-5.00 (m, 7H), 4.32-4.14 (m, 1H), 4.23 (dd, J=9.2, 5.3 Hz, 1H), 4.12 (d, J=5.7 Hz, 1H), 4.08 (dd, J=14.9, 10.1 Hz, 1H), 3.78-3.52 (m, 2H), 3.61 (d, J=10.0 Hz, 1H), 3.40-3.16 (m, 2H), 3.04 (dd, J=14.7, 7.6 Hz, 1H), 2.21 (dq. J=13.4, 4.6 Hz, 1H), 1.88 (ddd, J=21.9, 16.2, 8.7 Hz, 2H), 1.75-1.61 (m, 7H), 1.44-1.26 (m, 2H). $^{13}$C NMR (151 MHz, Methanol-d$_4$) δ 184.18, 183.51, 173.85, 169.04, 168.45, 158.71, 158.70, 138.12, 137.27, 137.24, 129.59, 129.48, 129.44, 129.35, 129.32, 129.21, 129.04, 128.98, 128.83, 128.78, 71.53, 71.45, 70.92, 70.85, 67.88, 67.70, 58.68, 58.03, 55.34, 53.15, 52.89, 51.34, 42.94, 42.85, 36.53, 36.46, 32.00, 31.91, 29.95, 29.25, 27.34, 27.31, 27.02, 26.28, 23.75, 23.72

HR-MS: (M+1)$^+$=787.3675 (experimental); exact mass=787.3661 (theoretical)

IR f (cm$^{-1}$): 3294, 1679, 1607, 1427, 1344, 1206, 1138, 844, 802, 725, 698.

[α]$_D$=+0.015° (c=1.8, MeOH)

Minor 8a(R) Epimer:

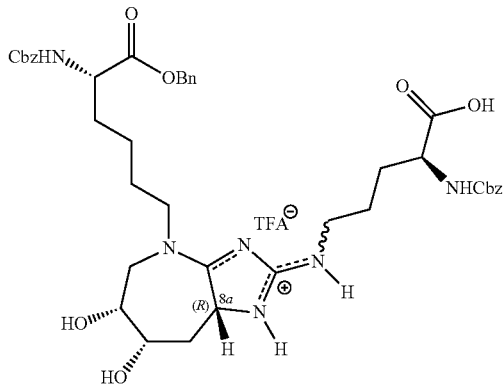

Prep HPLC retention time: 49.25 minutes
$^1$H NMR (800 MHz, Methanol-$d_4$) δ 7.36-7.27 (m, 15H), 5.19-5.01 (m, 6H), 4.67 (ddd, J=12.3, 10.1, 2.8 Hz, 1H), 4.25-4.15 (m, 2H), 4.02-3.99 (m, 1H), 3.85 (ddt, J=78.5, 14.1, 7.4 Hz, 1H), 3.73 (dq, J=11.5, 3.9 Hz, 1H), 3.62-3.49 (m, 2H), 3.46-3.34 (m, 2H), 3.23 (qd, J=11.9, 10.1, 7.3 Hz, 1H), 2.06-2.03 (m, 1H), 1.95-1.78 (m, 3H), 1.74-1.62 (m, 6H), 1.45-1.33 (m, 2H), $^{13}$C NMR (201 MHz, Methanol-$d_4$) δ 182.96, 182.21, 173.97, 168.49, 158.75, 158.69, 138.14, 137.25, 129.58, 129.48, 129.44, 129.33, 129.30, 129.21, 129.02, 128.99, 128.85, 128.81, 128.74, 72.70, 69.91, 69.85, 67.86, 67.67, 60.47, 59.92, 55.42, 55.31, 54.63, 54.37, 53.09, 43.19, 42.90, 32.45, 32.38, 31.96, 31.86, 29.97, 29.53, 27.10, 27.03, 26.93, 26.32, 23.75, 23.71.

HR-MS: $(M+1)^+$=787.3669 (experimental); exact mass=787.3661 (theoretical)

IR f (cm$^{-1}$): 3295, 1680, 1609, 434, 1345, 1206, 1140, 845, 802, 25, 698.

$[α]_D$=−0.013° (c=0.48, MeOH)

Iso-Imidazole Synthesis: One Step Rearrangement

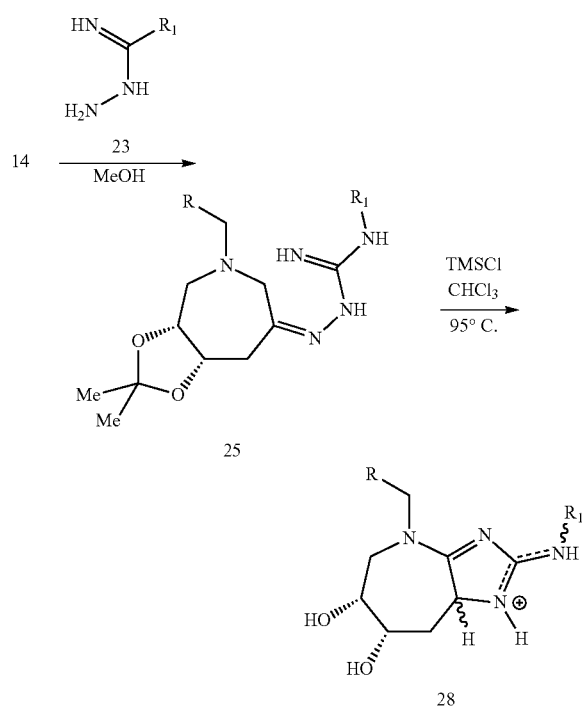

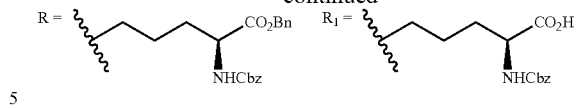

(S)-5-(2-(3aR,8aS,Z)-5-((S)-6-(benzyloxy)-5-((benzyloxy)carbonyl)amino)-6-oxohexyl-2,2-dimethyl-hexahydro-7H-[1,3]dioxolo[4,5-c]azepin-7-ylidene)hydrazine-1-carboximidamido)-2-(((benzyloxy)carbonyl)amino)pentanoic acid (24)

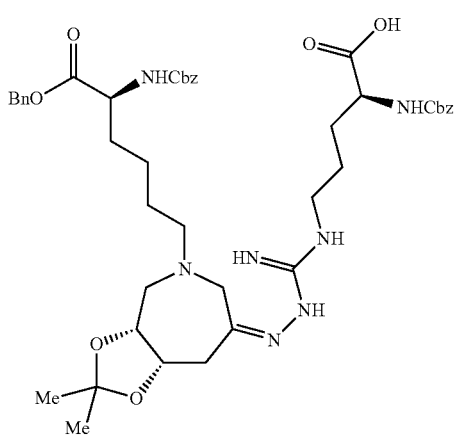 [SMILES: CC1(C)O[C@H]2C/C(=N/NC(=N)NCCC[C@H](NC(=O)OCc3ccccc3)C(=O)O)CN(CCCC[C@H](NC(=O)OCc3ccccc3)C(=O)OCc3ccccc3)C[C@H]2O1]

Ketone 14 (0.120 g, 0.223 mmol) was dissolved in anhydrous MeOH (2.2 mL), then N amino arginine 23 (0.072 g, 0.223 mmol) was added in one portion at room temperature. The resulting reaction mixture was stirred and monitored by LCMS. Upon complete consumption of starting material (~2 h), the mixture was evaporated to dryness to afford an orange yellow foam as a ~1:1 mixture of E/Z isomers. Purification was performed using Teledyne Isco with a reverse phase 15.5 g RediSep C18 column as the stationary phase. Water and ACN with 0.1% formic acid were used as the mobile phase. Column conditions: 10% ACN for 2 column volumes (CVs), 10→45% ACN over 27 CVs, 45% ACN for 5 CVs, 45→100% ACN over 2 CVs, and finally 100% ACN over 7 CVs. Pure E and Z isomers can be isolated but isomerize upon evaporation of solvents. Thus, pure condensed product was isolated as a monoformate salt and mixture of E/Z isomers in 69% yield (0.136 g, 0.154 mmol).

$^1$H NMR (400 MHz, Methanol-$d_4$) δ 7.38-7.26 (m, 15H), 5.17 (dd, J=19.6, 12.1 Hz, 2H), 5.09 (d, J=2.0 Hz, 4H), 4.71-4.61 (m, 2H), 4.27 (dd, J=9.6, 4.9 Hz, 1H), 4.21 (dd, J=8.2, 4.7 Hz, 1H), 4.14 (d, J=13.5 Hz, 1H), 3.93 (d, J=12.9 Hz, 1H), 3.78 (d, J=14.6 Hz, 1H), 3.53 (d, J=14.5 Hz, 1H), 3.39-3.34 (m, 2H), 3.24-3.14 (m, 2H), 3.10 (dd, J=16.2, 4.2 Hz, 1H), 2.78 (d, J=16.4 Hz, 1H), 1.99-1.86 (m, 2H), 1.81-1.70 (m, 6H), 1.49-1.43 (m, 2H), 1.43 (s, 3H), 1.37 (s, 3H). $^{13}$C NMR (151 MHz, Methanol-d) δ 175.27, 173.59, 158.75, 156.11, 146.70, 138.15, 137.22, 129.61, 129.49, 129.39, 129.30, 129.06, 128.77, 110.30, 74.32, 73.62, 68.00, 67.72, 60.12, 58.50, 54.99, 54.75, 52.89, 42.17, 32.42, 31.89, 29.94, 26.18, 25.94, 24.41, 23.81, 23.54.

HR-MS: $(M+1)^+$=844.4245 (experimental); exact mass=844.4245 (theoretical)

IR f (cm$^{-1}$): 2362, 2336, 1674, 1456, 1343, 1201, 1138, 1065, 838, 800, 22, 698, 668.

2,2,2-trifluoro-1λ³-ethan-1-one, (6R,7S,Z)-4-((S)-6-(benzyloxy)-5-(((benzyloxy)carbonyl)amino)-6-oxohexyl)-2-(((S)-4-(((benzyloxy)carbonyl)amino)-4-carboxybutyl)-λ⁴-azanylidene)-6,7-dihydroxy-1,2,4,5,6,7,8,8a-octahydroimidazo[4,5-b]azepin-1-ium salt (28)

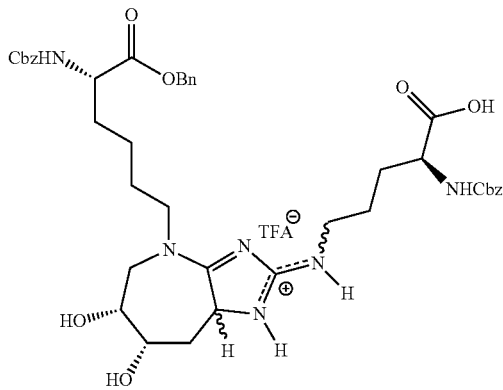

Carbazone 25 (0.040 mg, 0.0473 mmol) was added to a dry microwave vial charged with a stir bar and then dissolved in dry and degassed CHCl₃ (0.470 mL). Then, TMSCl (0.020 mL, 0.142 mmol) was added dropwise via syringe under argon. The vial was placed in an oil bath preheated to 95° C. The reaction was stirred at this temperature for 20 h, at which point LCMS analysis of the resulting dark reddish-brown mixture indicated complete consumption of starting material and formation of desired iso-imidazole ([M+H]⁺ 827). The reaction mixture was then treated with water (0.010 mL) and stirred at room temperature for 1 hour. LCMS analysis indicated full deprotection of the acetonide group ([M+H]⁺ 787). The reaction mixture was cooled in an ice bath and diluted with 1 M aqueous TFA (1.00 mL) and CH₂Cl₂ (0.500 mL). The resulting biphasic mixture was stirred vigorously for 5 min, then layers were allowed to separate, the bottom organic layer drown off, and the aqueous layer re-extracted twice with CH₂Cl₂ (1.00 mL). The combined organic layers were dried over anhydrous Na₂SO₄, filtered, and concentrated to a dark brown residue containing a 4:1 mixture of epimers, which was separated by preparative scale HPLC according to the procedure described above. The title compound was isolated as a TFA salt in 55% yield (0.020 g, 0.0260 mmol) as a white fluffy solid.

Glucosepane Tris-Trifluoroacetate (5)

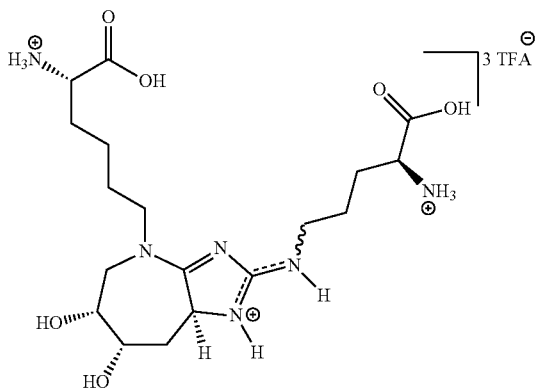

Protected glucosepane 28 (0.020 g, 0.0205 mmol) was dissolved in anhydrous MeOH (0.200 mL) and the solution was purged with nitrogen for 5 min. 10% Pd/C (0.021 mg, 0.0205 mmol) was added to the vial and the resulting slurry was further purged with nitrogen (1 min) before H₂ gas was added via a double walled balloon. Upon completion as indicated by LCMS analysis (~6 h), the reaction mixture was purged with nitrogen (5 min) and TFA (0.010 mL) was added. The crude reaction was filtered through a pad of celite with the aid of MeOH containing 0.1% TFA (20 mL) and the filtrate was evaporated to dryness in vacuo. The crude mixture was purified by preparative scale HPLC.

Preparatory HPLC was performed with a SunFire Prep Cl 8 OBD 5 □m 10×150 mm reversed-phase column as the stationary phase. H₂O and MeOH both buffered with 0.1% trifluoroacetic acid were used as the mobile phase. HPLC conditions: UV collection 254 nm, flow rate 5 mL/min, 0% MeOH linear gradient over 5 minutes, 0%→5% MeOH over 10 min, and 5% MeOH linear gradient over 5 min. The run was finished with a 100% MeOH wash. The HPLC fractions were combined and lyophilized, and the title compound was isolated in 78% yield (0.012 g, 0.0160 mmol, >95% pure) as a white fluffy solid.

Major Diastereomer: 8a(S)

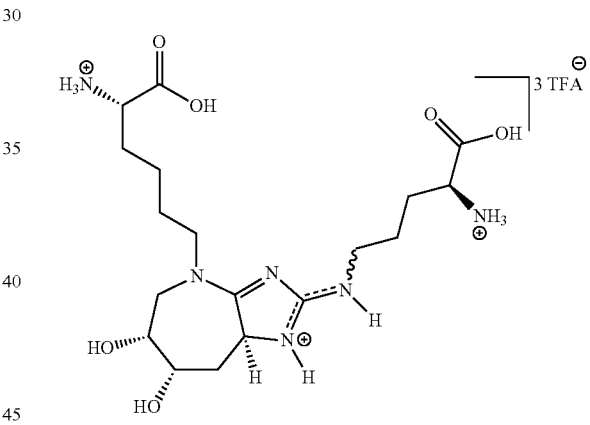

Prep HPLC Retention Time:—13.18 min

¹H NMR (800 MHz, D₂O) δ 5.14 (dd, J=12.1, 3.2 Hz, 1H), 4.24 (s, 1H), 4.09 (dd, J=15.0, 10.5 Hz, 1H), 3.90-3.83 (m, 2H), 3.80 (d, J=10.8 Hz, 1H), 3.72-3.64 (m, 1H), 3.57 (dt, J=13.9, 7.1 Hz, 1H), 3.49 (td, J=6.8, 2.2 Hz, minor E/Z isomer), 3.31 (t, J=6.9 Hz, 2H), 3.19-3.14 (m, 1H), 2.25 (ddd, J=14.9, 7.6, 3.8 Hz, 1H), 1.99-1.81 (m, 5H), 1.79-1.62 (m, 4H), 1.51-1.34 (m, 2H). ¹³C NMR (201 MHz, d₂o) δ 183.37, 182.33, 173.80, 167.68, 166.83, 70.00, 69.91, 57.60, 56.89, 54.10, 52.14, 52.07, 50.28, 50.13, 47.11, 42.31, 42.01, 34.79, 34.69, 30.13, 27.75, 27.66, 26.37, 26.33, 25.22, 24.18, 21.77.

HR-MS: (M+1)=429.2450 (experimental); exact mass=429.2456 (theoretical)

IR f (cm⁻¹): 3234, 1669, 1613, 1529, 1432, 1187, 1132, 841, 800, 723.

[α]_D=+0.038° (c=1.5, MeOD)

Minor Diastereomer: 8a(R)

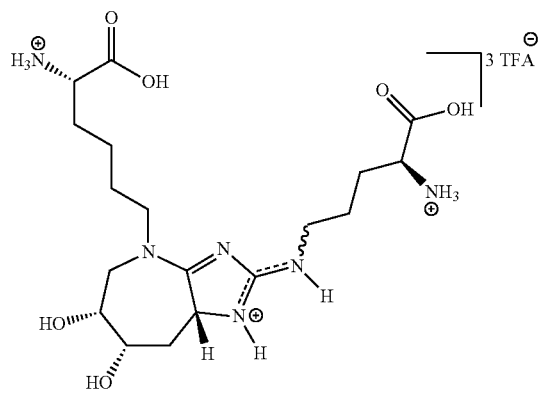

Prep HPLC Retention Time: 6.21 min $^1$H NMR (600 MHz, Deuterium Oxide) δ 4.84 (dd, J=12.2, 3.1 Hz, 1H), 4.75 (dd, J=12.0, 3.1 Hz, 0H), 4.16 (dd, J=6.8, 2.6 Hz, 1H), 3.92 (dt, J=11.9, 3.7 Hz, 1H), 3.90-3.80 (m, 3H), 3.71 (dd, J=15.6, 6.9 Hz, 1H), 3.63 (d, J=15.6 Hz, 1H), 3.52 (t, J=6.8 Hz, 0H), 3.39 (dt, J=13.8, 7.1 Hz, 1H), 3.33 (t, J=6.7 Hz, 2H), 2.15 (dt, J=12.6, 3.6 Hz, 1H), 1.94 (tdt, J=21.8, 11.2, 4.8 Hz, 4H), 1.85-1.62 (m, 5H), 1.52-1.34 (m, 2H).

$^{13}$C NMR (151 MHz, D$_2$O) δ 182.43, 181.39, 174.46, 174.29, 167.93, 167.09, 71.41, 68.97, 59.61, 58.97, 54.68, 54.49, 53.72, 52.22, 45.17, 42.54, 42.23, 31.03, 30.45, 28.03, 27.97, 26.32, 25.43, 24.42, 22.84, 22.11, 22.05, 22.01.

HR-MS: (M+1)$^+$=429.2459 (experimental); exact mass=429.2456 (theoretical)

IR f (cm$^{-1}$): 2941, 1674.5, 1616, 1530, 1430, 1349, 1202, 1134, 840, 801, 723.

[α]$_D$=−0.022° (c=1.23, D$_2$O)

Glucosepane Tris-Formate

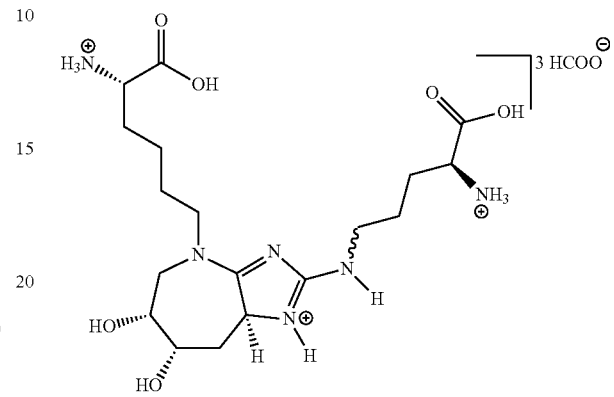

Glucosepane tris-trifluoroacetate 5 (0.010 g, 0.0139 mmol) was dissolved in 10% aqueous formic acid (0.300 mL) and stirred at room temperature for 30 min. The mixture was then frozen (−78° C.) and lyophilized. The title compound was isolated as a white fluffy solid in 89% yield (0.007 g, 0.124 mmol).

TABLE 2

Comparison to previously published $^1$H and $^{13}$C NMR δ(ppm) values for glucosepane formate salt in D$_2$O$^4$

| | δ (ppm) | | | δ (ppm) | | | J (Hz) | |
|---|---|---|---|---|---|---|---|---|
| $^1$H NMR | Lederer Assignment | Our Assignment | $^{13}$C NMR | Lederer Assignment | Our Assignment | | Lederer Assignment | Our Assignment |
| Major diastereomer: 8a(S) | | | | | | | | |
| H$_A$-5 | 3.16 | 3.16 | C-2 | 167.2 | 166.88 | $^2J_{5A, 5B}$ | 14.9 | 15.0 |
| H$_B$-5 | 4.09 | 4.09 | C-3a | 183.0 | 182.34 | $^2J_{8A, 8B}$ | 14.5 | 14.9 |
| H-6 | 3.80 | 3.80 | C-5 | 50.4 | 50.32 | $^2J_{1'A, 1'B}$ | 13.5 | 13.9 |
| H-7 | 4.24 | 4.24 | C-6 | 70.1 | 70.00 | $^3J_{5A, 6}$ | 2.4 | — |
| H$_A$-8 | 1.88 | 1.89 | C-7 | 69.9 | 69.95 | $^3J_{5B, 6}$ | 10.4 | 10.5 |
| H$_B$-8 | 2.25 | 2.25 | C-8 | 34.8 | 34.79 | $^3J_{6,7}$ | 2.4 | — |
| H-8$_a$ | 5.14 | 5.14 | C-8$_a$ | 57.6 | 57.60 | $^3J_{7, 8A}$ | 1 | — |
| H$_A$-1' | 3.59 | 3.57 | C-1' | 52.4 | 52.27 | $^3J_{7, 8B}$ | 4.9 | 3.8 |
| H$_B$-1' | 3.65 | 3.68 | C-2' | 26.4 | 26.46 | $^3J_{8A, 8a}$ | 12.2 | 12.1 |
| H$_2$-2' | 1.73 | 1.71 | C-3' | 22.0 | 21.93 | $^3J_{8B, 8a}$ | 2.8 | 3.2 |
| H$_2$-3' | 1.41 | 1.39 | C-4' | 30.3 | 30.49 | $^3J_{1'A, 2'}$ | 7.1 | 7.1 |
| H$_2$-4' | 1.88 | 1.87 | C-5' | 55.0 | 55.01 | $^3J_{1'', 2''}$ | 6.8 | 6.9 |
| H-5' | 3.69 | 3.70 | C-6' | 175.2 | 175.07 | | | |
| H$_2$-1'' | 3.30 | 3.30 | C-1'' | 42.2 | 42.11 | | | |
| H$_2$-2'' | 1.73 | 1.70 | C-2'' | 24.3 | 24.26 | | | |
| H$_2$-3'' | 1.89 | 1.89 | C-3'' | 28.1 | 28.02 | | | |
| H$_2$-4'' | 3.72 | 3.74 | C-4'' | 54.8 | 54.81 | | | |
| | | | C-5'' | 175.4 | 174.83 | | | |
| Minor diastereomer: 8a(R) | | | | | | | | |
| H$_A$-5 | 3.63 | 3.63 | C-2 | 167.1 | 167.06 | $^2J_{5A, 5B}$ | 15.4 | 15.6 |
| H$_B$-5 | 3.72 | 3.72 | C-3a | 182.0 | 181.35 | $^2J_{8A, 8B}$ | 12.6 | 12.6 |
| H-6 | 4.16 | 4.16 | C-5 | 52.2 | 52.20 | $^2J_{1'A, 1'B}$ | 14.0 | 13.8 |
| H-7 | 3.92 | 3.92 | C-6 | 69.0 | 68.99 | $^3J_{5A, 6}$ | <1 | — |
| H$_A$-8 | 1.82 | 1.82 | C-7 | 71.4 | 71.42 | $^3J_{5B, 6}$ | 6.6 | 6.8 |
| H$_B$-8 | 2.15 | 2.15 | C-8 | 31.0 | 31.00 | $^3J_{6,7}$ | 3.0 | 2.6 |
| H-8$_a$ | 4.84 | 4.84 | C-8$_a$ | 59.6 | 59.61 | $^3J_{7, 8A}$ | 11.9 | 11.9 |
| H$_A$-1' | 3.39 | 3.38 | C-1' | 53.8 | 53.81 | $^3J_{7, 8B}$ | 3-4 | 3.7 |
| H$_B$-1' | 3.87 | 3.87 | C-2' | 26.3 | 26.36 | $^3J_{8A, 8a}$ | 11.9 | 12.2 |
| H$_2$-2' | 1.72 | 1.71 | C-3' | 22.0 | 22.06 | $^3J_{8B, 8a}$ | 3-4 | 3.1 |

TABLE 2-continued

Comparison to previously published $^1$H and $^{13}$C NMR δ(ppm) values for glucosepane formate salt in $D_2O^4$

| $^1$H NMR | δ (ppm) Lederer Assignment | δ (ppm) Our Assignment | $^{13}$C NMR | δ (ppm) Lederer Assignment | δ (ppm) Our Assignment | | J (Hz) Lederer Assignment | J (Hz) Our Assignment |
|---|---|---|---|---|---|---|---|---|
| $H_2$-3' | 1.41 | 1.40 | C-4' | 30.6 | 30.63 | $^3J_{1'4, 2'}$ | 7.2 | 7.1 |
| $H_2$-4' | 1.88 | 1.88 | C-5' | 55.2 | 55.23 | $^3J_{1'', 2''}$ | 6.8 | 6.7 |
| H-5' | 3.72 | 3.71 | C-6' | 175.2 | 175.32 | | | |
| $H_2$-1'' | 3.33 | 3.33 | C-1'' | 42.2 | 42.26 | | | |
| $H_2$-2'' | 1.73 | 1.73 | C-2'' | 24.4 | 24.42 | | | |
| $H_2$-3'' | 1.91 | 1.91 | C-3'' | 28.2 | 28.16 | | | |
| $H_2$-4'' | 3.76 | 3.76 | C-4'' | 54.9 | 54.96 | | | |
| | | | C-5'' | 175.0 | 174.96 | | | |

Synthesis of Model Iso-Imidazoles 30

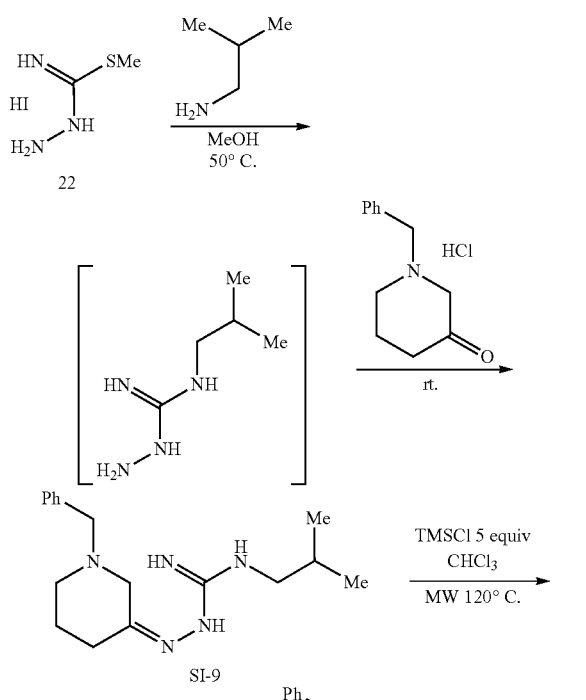

(Z)-2-(1-benzylpiperdin-3-ylidene-N-isobutylhydrazine-1-carboximidamide (SI-9)

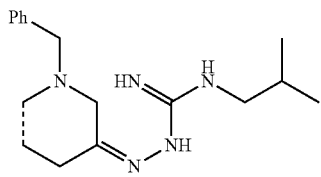

SMe-semicarbazide-HI 22 (0.233 g, 1.00 mmol) was dissolved in MeOH (1 mL) and iBu-NH$_2$ (0.100 mL, 1.00 mmol) was added drop wise via syringe. The resulting mixture was heated to 50° C. and monitored by LCMS. After 1 h, LCMS indicated complete conversion to iBu-N-aminoguanidine ([M+H]$^+$ 131.2), and to this orange solution was added commercial N-Bn-3-piperidone (0.226 g, 1.0 mmol). The resulting mixture was stirred at room temperature and monitored by LCMS. Upon full consumption of starting materials (~2 h), the solvent was evaporated in vacuo to an orange residue.

Purification by column chromatography using SiO$_2$ as the stationary phase and 1:1 MeCN:MeOH as the eluent yielded the title compound (SI-9) in 70% yield (0.210 g, 0.700 mmol) as orange foam.

$^1$H NMR (600 MHz, Methanol-d$_4$) δ 7.38-7.28 (m, 5H), 3.69 (s, 2H), 3.20 (s, 2H), 3.10 (d, J=7.1 Hz, 2H), 2.75-2.59 (m, 2H), 2.53-2.40 (m, 2H), 1.97-1.82 (m, 3H), 0.97 (d, J=6.7 Hz, 6H), $^{13}$C NMR (151 MHz, Methanol-d$_4$) δ 155.31, 155.18, 129.42, 129.04, 129.01, 128.09, 128.08, 127.42, 127.27, 62.12, 62.01, 58.41, 52.40, 51.52, 51.44, 31.78, 27.95, 27.93, 24.67, 24.61, 24.12, 23.04, 18.64, 18.61.

HR-MS: (M+1)$^+$=302.3200 (experimental); exact mass=302.3205 (theoretical)

IR f (cm$^{-1}$): 3155, 2957, 1633, 1494, 1454, 1390, 1341, 1241, 1117, 747, 700

4-benzyl-2-(isobutylamino)-5,6,7,7a-tetrahydro-4H-imidazo[4,5-b]pyridin-1-ium TFA salt (30)

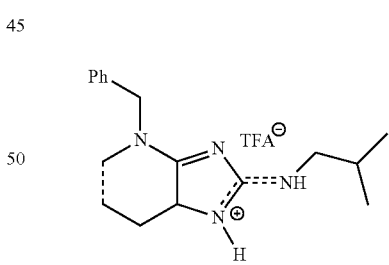

iBu-carbazone SI-9 (0.040 mg, 0.132 mmol) was added to a dry microwave vial charged with a stir bar and then dissolved in dry and degassed CHCl$_3$ (1.3 mL). Then, TMSCl (0.090 mL, 0.660 mmol) was added dropwise via syringe under argon. The vial was capped under argon and the resulting mixture was heated in a microwave reactor to 130° C. for 15 hours. The reaction mixture was then cooled to room temperature and the solvent removed in vacuo to yield a reddish brown residue. This residue was then taken up in CH$_2$Cl$_2$ (1 mL) and 10% aqueous TFA (1 mL). The aqueous layer was extracted three times with CH$_2$Cl$_2$ (1 mL), and the combined organic layers were then dried over Na$_2$SO$_4$. After filtration and evaporation of solvent in vacuo, the resulting crude residue was submitted to purification.

Purification was performed on preparatory HPLC with a SunFire Prep C18 OBD 10 μm 19×150 mm reversed-phase column as the stationary phase. H$_2$O and MeCN both buffered with 0.1% trifluoroacetic acid were used as the mobile phase. HPLC conditions: UV collection 254 nm, flow rate 20 mL/min, 10%→45% McCN linear gradient over 40 minutes. The HPLC fractions were combined and lyophilized to give a yellow oil in 33% yield (0.017 g, 0.0436 mmol)

Prep HPLC Retention Time: 24.52 min $^1$H NMR (600 MHz. Methanol-d$_4$) δ 7.41-7.32 (m, 5H), 4.91-4.80 (m, 3H), 4.76 (d. J=14.6 Hz, 1H), 4.69 (dd, J=11.6, 7.4 Hz, 1H), 4.63 (dd, J=11.6, 7.3 Hz, E/Z minor isomer), 3.52-3.38 (m, 2H), 3.37 (d, J=6.9 Hz, E/Z minor isomer), 3.10 (d, J=7.1 Hz, 2H), 2.47 (ttd, J=15.3, 7.6, 4.0 Hz, 1H), 1.98-1.84 (m, 2H), 1.84-1.76 (m, 1H), 1.58-1.43 (m, 2H), 1.00 (d J=6.7 Hz, 3H), 0.97 (dd, J=6.7, 1.1 Hz, E/Z minor isomer).

$^{13}$C NMR (151 MHz, Methanol-d$_4$) δ 181.51, 180.85, 170.53, 169.93, 136.36, 130.01, 129.46, 129.38, 129.36, 60.37, 59.99, 54.44, 54.19, 51.51, 51.15, 47.09, 46.89, 30.13, 29.48, 25.23, 25.18, 20.21, 20.18, 18.86, 18.83.

$^1$H NMR (600 MHz, Chloroform-d) δ 10.34 (s, 1H), 9.50 (s, 1H), 7.38 (d, J=7.0 Hz, 3H), 7.30-7.27 (m, 2H), 4.79 (s, 2H), 4.42 (d, J=9.7 Hz, 1H), 3.35 (t, J=6.3 Hz, 4H), 2.54 (s, 1H), 1.92 (dp, J=13.2, 6.5 Hz, 1H), 1.88-1.78 (m, 2H), 1.52 (q, J=10.2 Hz, 1H), 0.96 (d, J=7.0 Hz, 6H). $^{13}$C NMR (151 MHz, Chloroform-d) δ 179.82, 169.53, 134.40, 129.31, 128.88, 128.47, 59.07, 53.80, 50.78, 45.94, 29.05, 24.51, 20.12, 18.47.

HR-MS: (M+1)$^+$=285.2065 (experimental): exact mass=285.2074 (theoretical)

IR f (cm$^{-1}$): 2962, 1685, 1611, 1510, 1350, 1201, 1131, 801, 720, 702.

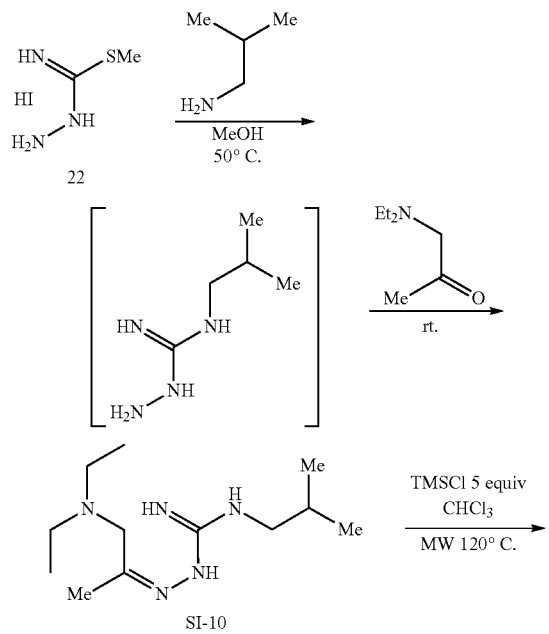

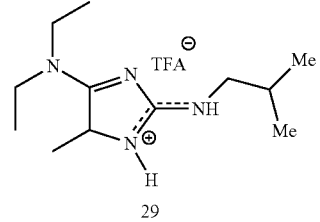

(Z)-2-(1-(diethylamino)propan-2-ylidene)-N-Isobutylhydrazine-1-carboximidamide (SI-10)

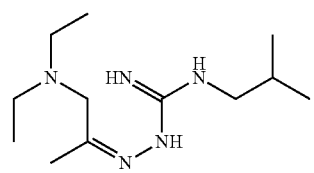 [SMILES: CCN(CC)C/C(C)=N\NC(=N)NCC(C)C]

SMe-semicarbazide HI 22 (0.233 mg, 1.00 mmol) was dissolved in MeOH (1 mL) and iBu-NH2 (0.100 mL, 1.00 mmol) was added drop wise via syringe. The resulting mixture was heated to 50° C. and monitored by LCMS. After 1 h, LCMS indicated complete conversion to iBu-N-aminoguanidine ([M+H]$^+$ 131.2), and to this orange solution was added 1-(diethylamino)propan-2-one (0.129 mg, 1.0 mmol). The resulting mixture was stirred at room temperature and monitored by LCMS. Upon completion and full consumption of starting materials (~2 h), the solvent was evaporated in vacuo to a brown viscous oil. Purification was performed using Teledyne Isco with a reverse phase 15.5 g RediSep C18 column as the stationary phase. Water and ACN buffered with 0.1% FA were used as the mobile phase. Column conditions: 0% ACN for 4 column volumes (CV) followed by 0→20% ACN over 25 CVs, 20% ACN for 5 CVs, 20→100% ACN over 2 CVs, and finally 100% ACN over 5 CVs. Pure condensed product was isolated as a monoformate salt and mixture of E/Z isomers in 58% yield (0.167 g, 0.583 mmol).

$^1$H NMR (600 MHz, Methanol-d$_4$) δ 8.44 (s, 1H), 4.06-4.00 (m, 2H), 3.26 (dddd, J=17.2, 10.4, 6.9, 2.7 Hz, 4H), 3.15 (d, J=7.1 Hz, 2H), 2.05 (d, J=2.4 Hz, 3H), 1.94 (hept, J=6.7 Hz, 1H), 1.32 (qd, J=7.4, 5.9, 2.6 Hz, 6H), 0.99 (d, J=6.6 Hz, 6H). $^{13}$C NMR (151 MHz, Methanol-d$_4$) δ 168.93, 156.71, 50.13, 50.09, 49.77, 29.29, 20.14, 15.71, 15.66, 9.52, 9.44.

HR-MS: (M+1)$^+$=242.2340 (experimental): exact mass=242.2345 (theoretical)

IR f (cm$^{-1}$): 2966, 1670, 1613, 1470, 1372, 1345, 1201, 1176, 1131, 830, 801, 720.

5-(diethylamino)-2-(isobutylamino)-4-methyl-4H-imidazol-3-ium TFA salt (29)

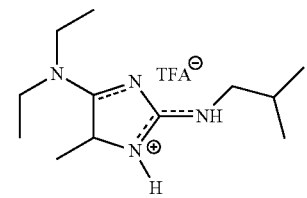

iBu-carbazone SI-10 formate salt (0.038 mg, 0.132 mmol) was added to a dry microwave vial charged with a stir bar and then dissolved in dry and degassed CHCl$_3$ (1.3 mL). Then TMSCl (0.090 mL, 0.660 mmol) was added drop wise via syringe under argon. The vial was capped under argon and the resulting mixture was heated in a microwave reactor to 130° C. for 15 hours. The reaction mixture was then cooled to room temperature and solvent removed in vacuo to yield a reddish brown residue which was submitted directly to purification.

Purification was performed on preparatory HPLC with a SunFire Prep C18 OBD 10 μm 19×150 mm reversed-phase column as the stationary phase. $H_2O$ and MeCN both buffered with 0.1% trifluoroacetic acid were used as the mobile phase. HPLC conditions: UV collection 254 nm, flow rate 20 mL/min, 20%→60% MeCN linear gradient over 25 minutes. The HPLC fractions were combined and lyophilized to a pale yellow residue in 12% yield (0.004 g, 0.0158 mmol).

$^1$H NMR (600 MHz, $CDCl_3$) δ 10.73 (s, 1H), 9.58 (d, J=5.7 Hz, 1H), 4.62 (q, J=6.7 Hz, 1H), 3.63 (dp, J=24.9, 6.8 Hz, 2H), 3.39 (ddt, J=38.5, 14.4, 7.2 Hz, 2H), 3.27 (h, J=6.7 Hz, 2H), 1.88 (hept, J=6.7 Hz, 1H), 1.50 (d, J=6.7 Hz, 3H), 1.33 (t, J=7.1 Hz, 3H), 1.26 (t, J=7.1 Hz, 3H), 0.93 (d. J=6.7 Hz, 6H). $^{13}$C NMR (151 MHz, $CDCl_3$) δ 180.56, 168.07, 57.25, 50.51, 44.71, 43.71, 29.16, 20.09, 18.75, 14.10, 12.05.

HR-MS: $(M+1)^+$=225.2066 (experimental); exact mass=225.2074 (theoretical)

IR f $(cm^{-1})$: 1682, 1602, 1210, 1137, 726.

Evidence for Conformational Exchange (E/Z isomerization)

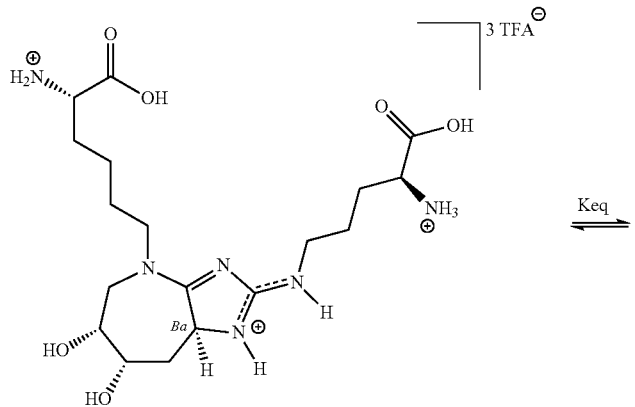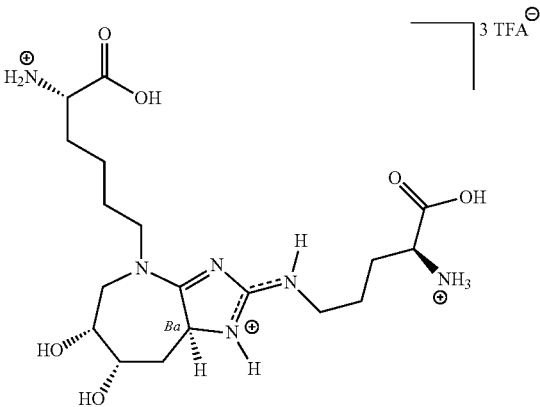

The integral ratios and $t_m$ were used to calculate an approximate rate by the following formula:[5]

$$k = \frac{1}{t_m}\ln\frac{p+1}{p-1}, \text{ where } r = \left(\frac{4X_aX_b(I_{aa}+I_{bb})}{I_{ab}+I_{ba}}\right) - (X_a - X_b)^2$$

$X_a$=mole fraction of conformer A
$X_b$=mole fraction of conformer B
$I_{aa}$=integral intensity for diagonal peak (conformer A)
$I_{bb}$=integral intensity for diagonal peak (conformer B)
$I_{ab}$ and $I_{ba}$=integral intensity for cross-peak
Sample calculation with the data provided above:

| $I_{aa}$ | $I_{bb}$ | $I_{ab}$ | $I_{ba}$ | $X_a$ | $X_b$ | r | $t_m$ (sec) | $k(s^{-1})$ |
|---|---|---|---|---|---|---|---|---|
| 0.16 | 0.33 | 0.33 | 0.741 | 0.259 | 1.12 | 1.00 | 2.89 | |

Figure 7:
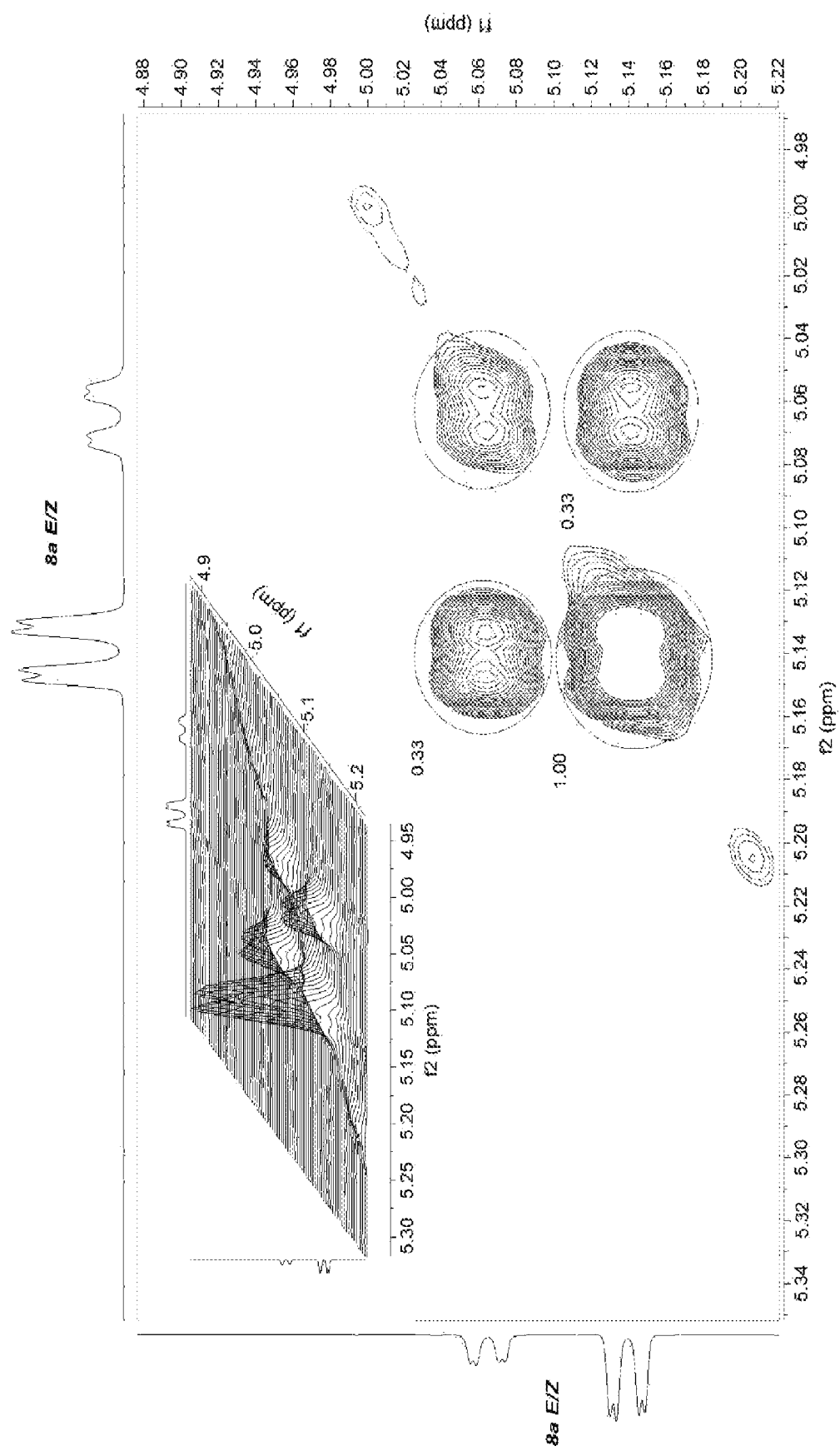
FIG. 7 shows 2D NOESY with $t_m$=1000 ms.

FIG. 7 shows 2D NOESY with $t_m$=1000 ms.

Glucosepane $pK_a$ Study

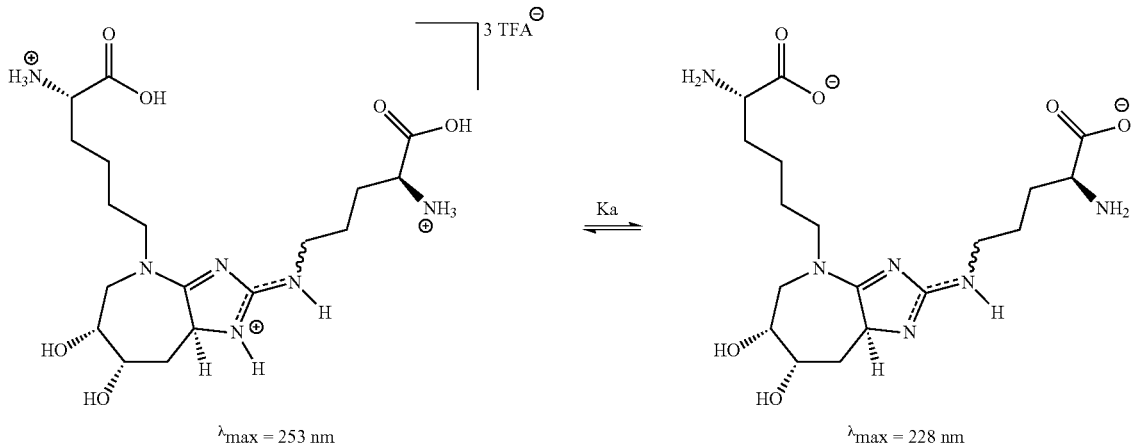

$\lambda_{max}$ = 253 nm $\lambda_{max}$ = 228 nm

Desired pH buffers were prepared starting with commercial pH 13 buffer (containing glycine/sodium hydroxide/sodium chloride—Fluka) and titrating freshly prepared 6 M aqueous HCl until the desired pH was obtained.

A stock solution (1.73 µM) of glucosepane tris-TFA salt was prepared with MilliQ water.

Figure 8:
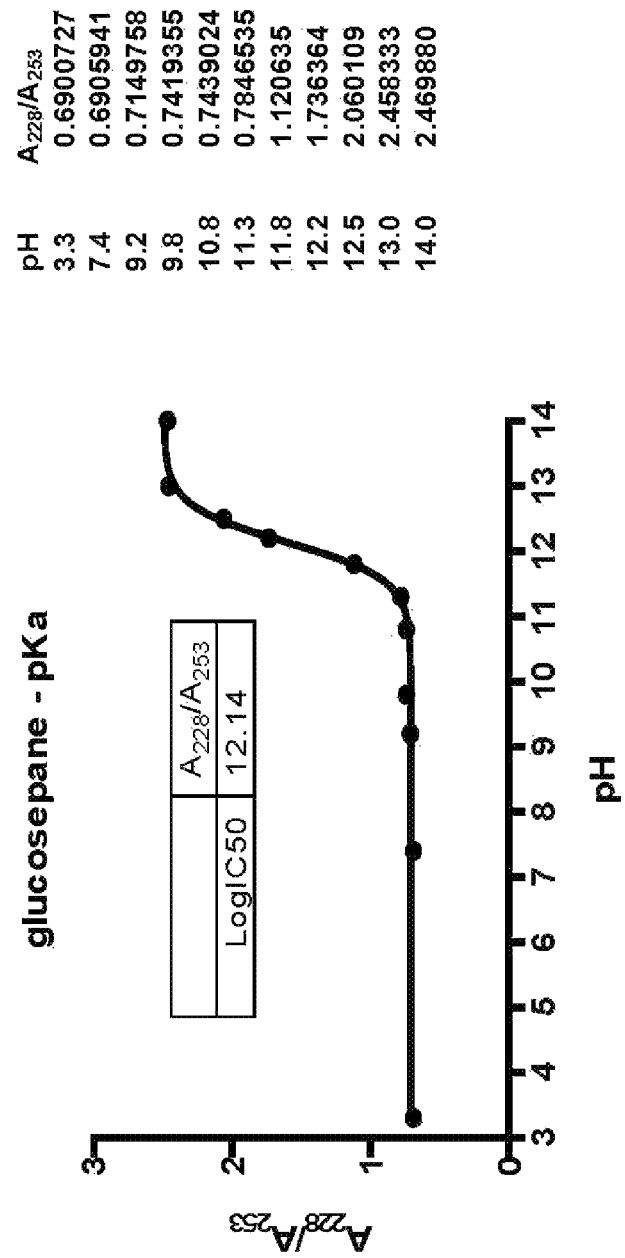
FIG. 8 shows a pH titration of glucosepane.

20 µl of stock solution were dispensed into micro-centrifuge vials and then 60 µl of appropriate pH buffer were added. The resulting mixture was centrifuged for 1 min and then UV spectra was acquired on 2 µl aliquots using a NanoDrop 1000 spectrophotometer (Thermo), monitoring absorbance at 253 and 228 nm. The results are set forth in attached FIG. 8.

REFERENCES—FIRST SET

1. C. T. Walsh, S. Gameau-Tsodikova, G. J. Gatto, Jr., Protein posttranslational modifications: the chemistry of proteome diversifications. *Angew. Chem. Int. Ed. Engl.* 44, 7342-7372 (2005).
2. R. Singh. A. Barden. T. Mori, L. Beilin. Advanced glycation end-products: a review. *Diabetologia* 44, 129-146 (2001).
3. V. M. Monnier et al., Glucosepane: a poorly understood advanced glycation end product of growing importance for diabetes and its complications. *Clin. Chem. Lab. Med.* 52, 21-32 (2014).
4. M. Hellwig, T. Henle, Baking, ageing, diabetes: a short history of the Maillard reaction. *Angew. Chem. Int. Ed. Engl.* 53, 10316-10329 (2014).
5. K. M. Biemel, D. A. Friedl, M. O. Lederer, Identification and quantification of major maillard cross-links in human serum albumin and lens protein. Evidence for glucosepane as the dominant compound. *J. Biol. Chem.* 277, 24907-24915 (2002).
6. K. Biemel, H. Bihler. O. Reihl, M. Lederer, Identification and quantitative evaluation of the lysine-arginine cross-links GODIC, MODIC, DODIC, and glucosepan in foods. *Nahrung/Food* 45, 210-214 (2001).
7. V. M. Monnier et al., The association between skin collagen glucosepane and past progression of microvascular and neuropathic complications in type I diabetes. *J. Diabetes Complicat.* 27, 141-149 (2013).
8. J. S. Sjoberg, S. Bulterijs, Characteristics, formation, and pathophysiology of glucosepane: a major protein cross-link. *Rejuvenation Res* 12, 137-148 (2009).
9. X. Fan et al., Anaerobic vs aerobic pathways of carbonyl and oxidant stress in human lens and skin during aging and in diabetes: A comparative analysis. *Free. Radic. Biol. Med.* 49, 847-856 (2010).
10. D. Sell et al., Glucosepane is a major protein cross-link of the senescent human extracellular matrix—Relationship with diabetes. *J. Biol. Chem.* 280, 12310-12315 (2005).
11. S. L. Schnider, R. R. Kohn, Effects of age and diabetes mellitus on the solubility and nonenzymatic glucosylation of human skin collagen. *J. Clin. Invest.* 67, 1630-1635 (1981).
12. S. L. Schnider, R. R. Kohn, Effects of age and diabetes mellitus on the solubility of collagen from human skin, tracheal cartilage and dura mater. *Exp. Gerontol.* 17, 185-194 (1982).
13. C. A. Vater, E. D. Hams, Jr., R. C. Siegel, Native cross-links in collagen fibrils induce resistance to human synovial collagenase. *Biochem. J.* 181, 639-645 (1979).
14. S. Genuth et al., in *Diabetes*. (2014), vol. 64, pp. 2668-278.
15. M. B. Manigrasso, J. Juranek, R. Ramasamy. A. M. Schmidt, Unlocking the biology of RAGE in diabetic microvascular complications. *Trends. Endocrin. Met.* 25, 15-22 (2014).
16. T. Henle, in *Kidney Int.* (2003), vol. 63, pp. S145-S147.
17. K. M. Biemel. J. Conrad, M. O. Lederer, Unexpected carbonyl mobility in aminoketoses: the key to major Maillard crosslinks. *Angew. Chem. Int. Ed. Engl.* 41, 801-804 (2002).
18. K. Biemel, D. Friedl, M. Lederer, in *J Biol Chem.* (2002), vol. 277, pp. 24907-24915.
19. A. N. Chermahini, B. Hosseinzadeh, A. S. Beni, A. Teimouri, Relation between the substituent effect and aromaticity in imidazole derivatives: A comparative study. *Comput. Theor. Chem.* 994, 97-104 (2012).
20. See Supporting Info for a full account of the computational studies
21. A. P. Rauter et al., Efficient synthesis of alpha,beta-unsaturated gamma-lactones linked to sugars. *Tetrahedron Asymmetry* 12, 1131-1146 (2001).
22. Full synthetic sequence from diacetone-D-glucose to epoxide 8 is presented in detail in the Supporting Information
23. Analysis of the crude reactions always showed 15-20% of hemiaminal present even after prolonged exposure to reaction conditions.
24. J. E. Hodge, C. E. Rist, The Amadori Rearrangement under New Conditions and its Significance for Non-enzymatic Browning Reactions2. *J. Am. Chem. Soc.* 75, 316-322 (1953).
25. E. M. Sánchez-Fernández, E. Alvarez, C. Ortiz Mellet, J. M. Garcia Feminidez, Synthesis of Multibranched Australine Derivatives from Reducing Castanospermine Analogues through the Amadori Rearrangement of gem-Diamine Intermediates: Selective Inhibitors of β-Glucosidase. *J. Org. Chem.* 79, 11722-11728 (2014).
26. Z. Dai et al., Identification of glucose-derived cross-linking sites in ribonuclease A. *J. Proteome. Res.* 7, 2756-2768 (2008).
27. M. J. Martin, L. J. Dorn, J. M. Cook, Novel pyridodiindoles, azadiindoles, and indolopyridoimidazoles via the Fischer-indole cyclization. *Heterocycles* 36, 157-189 (1993).
28. *The chemistry of hydroxylamines, oximes and hydroxamic acids.* Z. Rappaport, J. F. Liebman, Eds., (John Wiley & Sons, 2008), vol. 175.
29. A. J. Lawson, Hetero-cope rearrangement via an isolable intermediate. *J. Chem. Soc. Chem. Comm.*, 456 (1979).
30. L. E. Overman, Mercury (II)—and Palladium (II)—Catalyzed [3, 3]—Sigmatropic Rearrangements [New Synthetic Methods (46)]. *Angew. Chem. Int. Ed. Engl.* 23, 579-586 (1984).
31. See Supporting info
32. After much experimentation, oxo-iso-thioimidazole 27 proved synthetically useful and rendered the coveted diamino-iso-imidazole, core via an addition/reduction sequence, the details of which are described in the Supporting Information section.
33. Full synthetic sequence to iso-imidazoles 29 and 30 is presented in detail in the Supporting Information
34. C. L. Perrin, T. J. Dwyer, Application of 2-Dimensional Nmr to Kinetics of Chemical-Exchange. *Chem. Rev.* 90, 935-967 (1990).
35. M. O. Lederer, F. Gerum, T. Severin, Cross-linking of proteins by maillard processes—Model reactions of d-glucose or methylglyoxal with butylamine and guanidine derivatives. *Bioorg. Med. Chem.* 6, 993-1002 (1998).

REFERENCES—SECOND SET FOR EXPERIMENTAL SECTION (1) Mereyala, H. B.; Pathuri, G.; Nagarapu, L. *Synthetic Commun* 2012, 42, 1278.
(2) Kurhade, S. E.; Salunkhe. V. T.; Siddaiah, V.; Bhuniya, D.; Reddy. D. S. *Synthesis-Stuttgart* 2011, 3523.
(3) Rauter. A. P.; Figueiredo, J.; Ismael, M.; Canda, T.; Font, J.; Figueredo, M. *Tetrahedron-Asymmetr* 2001, 12, 1131.
(4) Biemel, K. M.; Conrad. J.; Lederer, M. O. *Angew Chem Int Ed Engl* 2002, 41, 801.
(5) Perrin, C. L.; Dwyer. T. J. *Chem Rev* 1990, 90, 935.

The invention claimed is:
1. A compound according to the chemical structure:

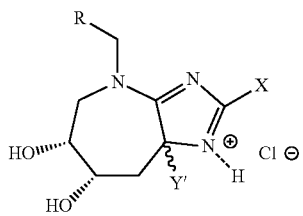

or a free amine or pharmaceutically acceptable salt thereof, wherein:
R is $C_1$-$C_{12}$ alkyl, $C_2$-$C_{12}$ alkenyl, $C_2$-$C_{12}$ alkynyl, phenyl, pyrrolyl, furanyl, thiophenyl, imidazolyl, oxazolyl, thiazolyl, pyrazolyl, pyridinyl, pyrazinyl, pyridazinyl or pyrimidinyl; or
R is:

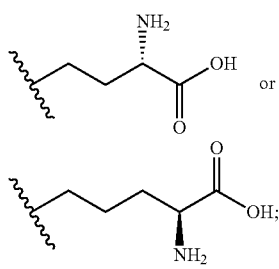

X is $NR^1R^2$, O—($C_1$-$C_{12}$) alkyl or S-alkyl, where the alkyl of S-alkyl is optionally substituted with halogen, hydroxy, alkoxy, cyano, azido or nitro; or
X is:

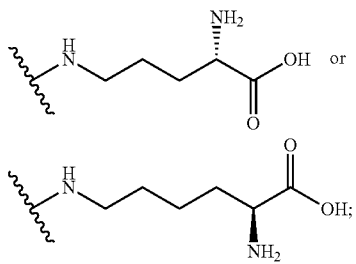

or
X is an amino acid group according to the chemical structure:

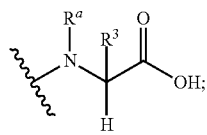

$R^1$ is H, alkyl, phenyl, pyrrolyl, furanyl, thiophenyl, imidazolyl, oxazolyl, thiazolyl, pyrazolyl, pyridinyl, pyrazinyl, pyridazinyl or pyrimidinyl, where the alkyl is optionally substituted with halogen, hydroxy, alkoxy, cyano, azido or nitro;
$R^2$ is H, alkyl, phenyl, pyrrolyl, furanyl, thiophenyl, imidazolyl, oxazolyl, thiazolyl, pyrazolyl, pyridinyl, pyrazinyl, pyridazinyl or pyrimidinyl, where the alkyl is optionally substituted with halogen, hydroxy, alkoxy, cyano, azido or nitro;
$R^a$ is H, $C_1$-$C_6$ alkyl or alkanol;
$R^3$ is $CH_3$, $CH(CH_3)_2$, $CH(CH_3)CH_2CH_3$, $CH_2CH(CH_3)_2$, $CH_2OH$, $CH(OH)CH_3$, $CH_2CONH_2$, $(CH_2)_2CONH_2$, $CH_2CO_2H$, $(CH_2)_2CO_2H$, $CH_2SH$, $(CH_2)_2SCH_3$, $(CH_2)_4NH_3^+$, $(CH_2)_3NH(C=NH_2^+)NH_2$,

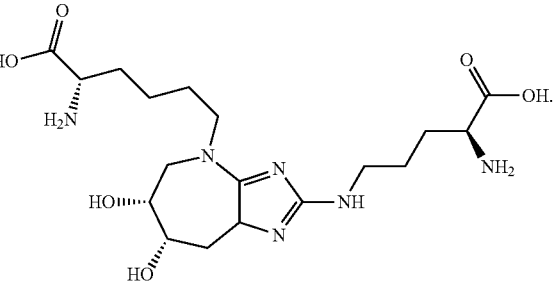

and
Y' is H or OH;
with the proviso that the compound is not according to the chemical structure below:

2. The compound according to claim 1, or a free amine or pharmaceutically acceptable salt thereof, wherein:
X is $NHR^1$, O—($C_1$-$C_{12}$) alkyl or S—($C_1$-$C_{12}$) alkyl; and $R^1$ is $C_1$-$C_{10}$ alkyl.
3. The compound according to claim 1, or a free amine or pharmaceutically acceptable salt thereof, wherein:
X is $NHR^1$, O—($C_1$-$C_3$) alkyl or S—($C_1$-$C_3$) alkyl; and $R^1$ is $C_1$-$C_3$ alkyl.
4. The compound according to claim 1, or a free amine or pharmaceutically acceptable salt thereof, wherein X is $NHCH_3$, $OCH_3$ or $SCH_3$.
5. The compound according to claim 1, or a free amine or pharmaceutically acceptable salt thereof, wherein X is $SCH_3$.
6. A pharmaceutical composition comprising a therapeutically effective amount of a compound according to claim 1, or a free amine or pharmaceutically acceptable salt thereof, in combination with a pharmaceutically acceptable carrier, additive or excipient.
7. The pharmaceutical composition according to claim 6, wherein the pharmaceutical composition further comprises an additional bioactive agent selected from the group consisting of a biguanide, a glucosidase inhibitor, an insulin, a meglitinide, a sulfonylurea, a biguanide/glyburide combination, a thiazolidinedione, a peroxisome proliferator-activated receptor-alpha agonist, a peroxisome proliferator-activated receptor-gamma agonist, a peroxisome proliferator-activated receptor-alpha/gamma dual agonist, a sodium-glucose cotransporter 2 inhibitor, an inhibitor of fatty acid binding protein, a glucagon-like peptide 1 and a dipeptidyl peptidase IV inhibitor, or a mixture thereof.

8. A compound selected from the group consisting of:

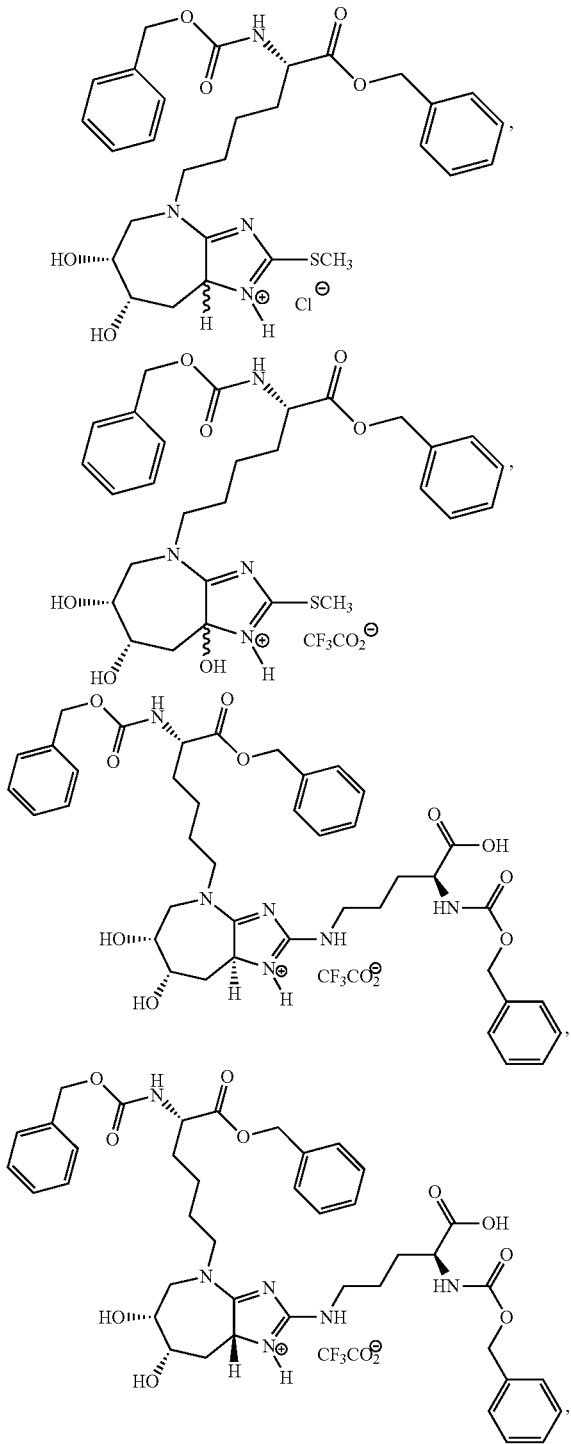

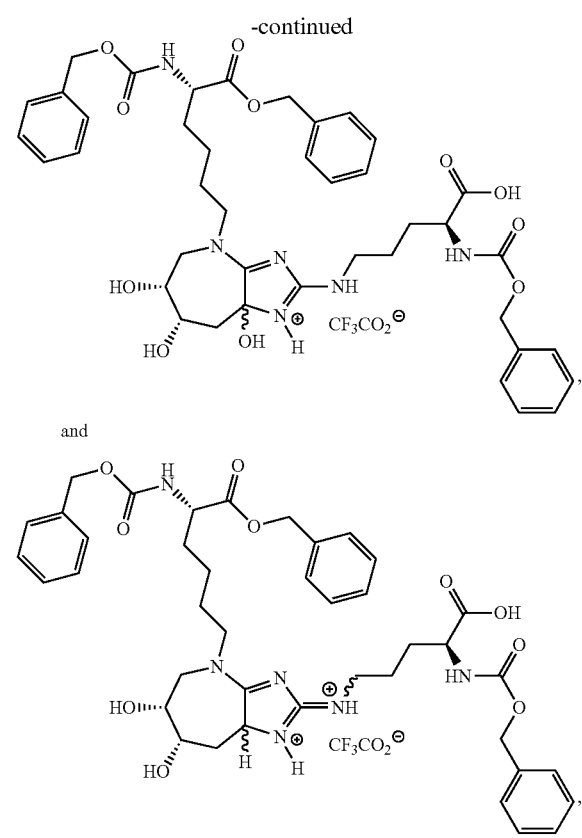

and or a free amine, pharmaceutically acceptable salt or tautomer thereof.

9. A compound selected from the group consisting of:

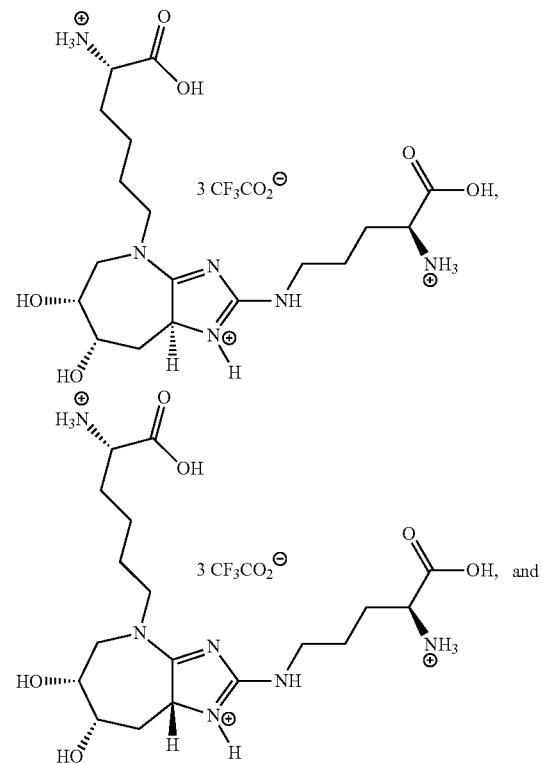

-continued

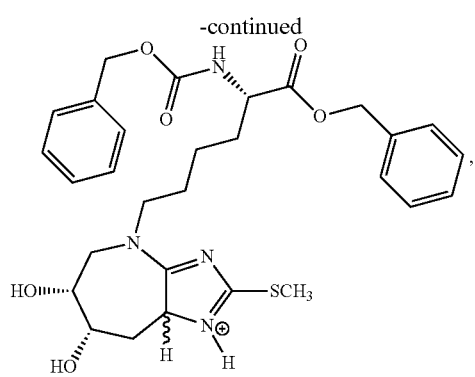

or a free amine, pharmaceutically acceptable salt or tautomer thereof.

10. The compound of claim 9, wherein the compound is selected from the group consisting of:

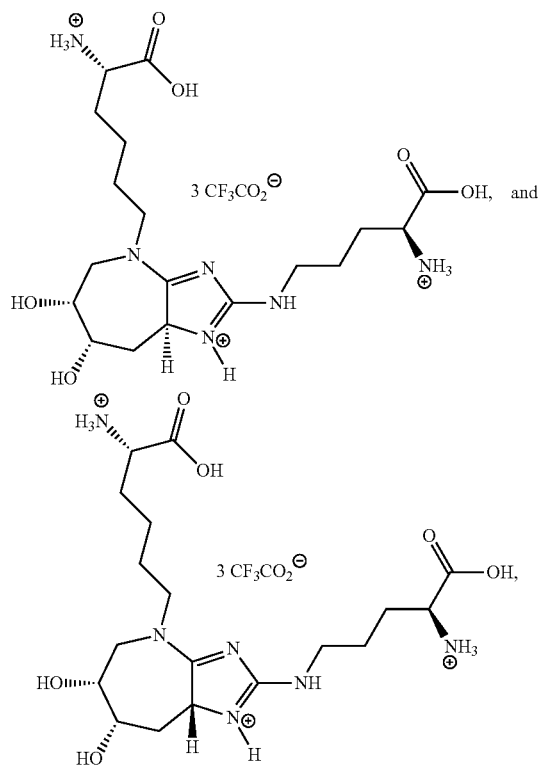

or a free amine, pharmaceutically acceptable salt or tautomer thereof.

11. A compound selected from the group consisting of:

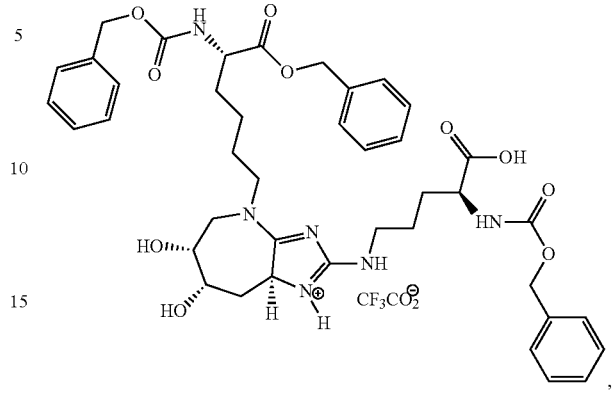

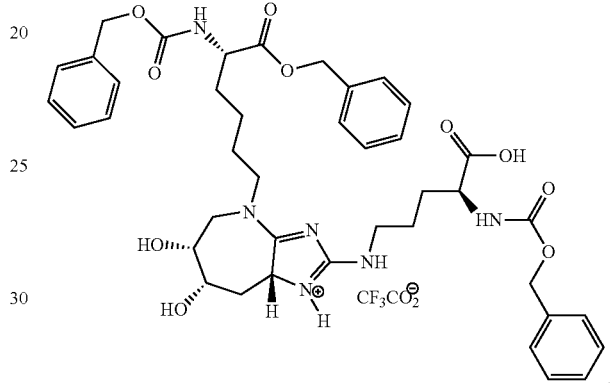

and

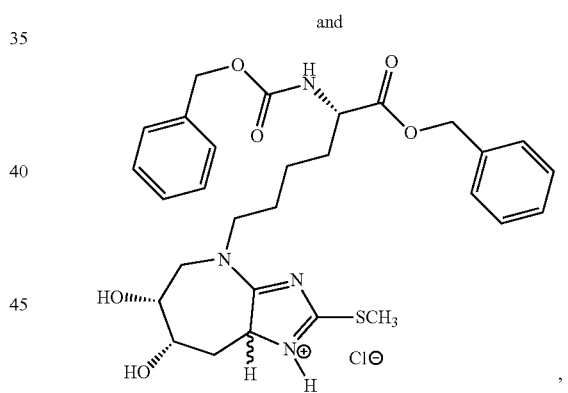

or a free amine, pharmaceutically acceptable salt or tautomer thereof.

* * * * *